(12) United States Patent
Weeks et al.

(10) Patent No.: US 9,713,572 B2
(45) Date of Patent: Jul. 25, 2017

(54) DELAMINATION RESISTANT PHARMACEUTICAL GLASS CONTAINERS CONTAINING ACTIVE PHARMACEUTICAL INGREDIENTS

(71) Applicant: Corning Incorporated, Corning, NY (US)

(72) Inventors: Wendell P. Weeks, Corning, NY (US); Robert Anthony Schaut, Painted Post, NY (US); Steven Edward DeMartino, Painted Post, NY (US); John Stephen Peanasky, Big Flats, NY (US)

(73) Assignee: Corning Incorporated, Corning, NY (US)

(*) Notice: Subject to any disclaimer, the term of this patent is extended or adjusted under 35 U.S.C. 154(b) by 180 days.

(21) Appl. No.: 14/259,255

(22) Filed: Apr. 23, 2014

(65) Prior Publication Data
US 2015/0071913 A1    Mar. 12, 2015

Related U.S. Application Data

(60) Provisional application No. 61/815,696, filed on Apr. 24, 2013.

(51) Int. Cl.
| | |
|---|---|
| A61K 39/395 | (2006.01) |
| A61J 1/00 | (2006.01) |
| C03C 3/087 | (2006.01) |
| C03C 3/091 | (2006.01) |
| C03C 4/20 | (2006.01) |
| C03C 21/00 | (2006.01) |
| C07K 16/24 | (2006.01) |
| C07K 16/28 | (2006.01) |
| C07K 16/32 | (2006.01) |
| A61K 47/48 | (2006.01) |

(52) U.S. Cl.
CPC ........... *A61J 1/00* (2013.01); *A61K 39/39591* (2013.01); *A61K 47/48384* (2013.01); *A61K 47/48561* (2013.01); *C03C 3/087* (2013.01); *C03C 3/091* (2013.01); *C03C 4/20* (2013.01); *C03C 21/002* (2013.01); *C07K 16/244* (2013.01); *C07K 16/2863* (2013.01); *C07K 16/2866* (2013.01); *C07K 16/2887* (2013.01); *C07K 16/32* (2013.01); *C07K 2317/94* (2013.01); *Y10T 428/131* (2015.01)

(58) Field of Classification Search
None
See application file for complete search history.

(56) References Cited

U.S. PATENT DOCUMENTS

| | | |
|---|---|---|
| 1,115,972 A | 11/1914 | Potter |
| 2,344,630 A | 3/1944 | Mylchreest |
| 3,054,686 A | 9/1962 | Hagedorn |
| RE25,456 E | 10/1963 | Bacon et al. |
| 3,351,474 A | 11/1967 | Hagedorn et al. |
| 3,490,885 A | 1/1970 | Hammer |
| 3,673,049 A | 6/1972 | Giffen et al. |
| 3,728,095 A | 4/1973 | Grubb et al. |
| 3,772,135 A | 11/1973 | Hara et al. |
| 3,844,754 A | 10/1974 | Grubb et al. |
| 3,844,758 A | 10/1974 | Wartenberg |
| 3,900,329 A | 8/1975 | Grubb et al. |
| 3,936,287 A | 2/1976 | Beall et al. |
| 4,021,218 A | 5/1977 | Watanabe |
| 4,065,317 A | 12/1977 | Baak et al. |
| 4,161,556 A | 7/1979 | Lenard et al. |
| 4,312,953 A | 1/1982 | Mills et al. |
| 4,689,085 A | 8/1987 | Plueddemann |
| 4,842,630 A | 6/1989 | Braithwaite et al. |
| 4,913,720 A | 4/1990 | Gardon et al. |
| 5,114,757 A | 5/1992 | Linde et al. |
| 5,286,527 A | 2/1994 | Blum et al. |
| 5,337,537 A | 8/1994 | Soughan |
| 5,547,929 A | 8/1996 | Anderson, Jr. et al. |
| 5,547,933 A | 8/1996 | Lin |
| 5,559,060 A | 9/1996 | Dumbaugh, Jr. et al. |
| 5,580,755 A | 12/1996 | Souza |

(Continued)

FOREIGN PATENT DOCUMENTS

| | | |
|---|---|---|
| CN | 101717189 A | 6/2010 |
| CN | 102123960 A | 7/2011 |

(Continued)

OTHER PUBLICATIONS

Adams RA. Formal discussion: the role of transplantation in the experimental investigation of human leukemia and lymphoma. Cancer Res. Dec. 1967;27(12):2479-81.
Barrowcliffe TW, et al., Anticoagulant activities of lung and mucous heparins. Thromb Res. Jan. 1978;12(1):27-36.
Beum PV et al., Three new assays for rituximab based on its immunological activity or antigenic properties: analyses of sera and plasmas of RTX-treated patients with chronic lymphocytic leukemia and other B cell; lymphomas. J Immunol Methods. Jun. 2004; 289: 97-109.
Brunner KT et al. Quantitative assay of the lytic action of immune lymphoid cells on 51-Cr-labelled allogeneic target cells in vitro; inhibition by isoantibody and by drugs. Immunology. Feb. 1968;14(2):181-96.
Casset et al., "A peptide mimetic of an anti-CD4 monoclonal antibody by rational design", Biochem Biophys Res Commun. Jul. 18, 2003; vol. 307, No. 1, pp. 198-205.
Corrected Notice of Allowance mailed Sep. 11, 2013, relating to U.S. Appl. No. 13/660,394, filed Oct. 25, 2012.

(Continued)

*Primary Examiner* — Yunsoo Kim
(74) *Attorney, Agent, or Firm* — Michael G. Panian

(57) ABSTRACT

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage of pharmaceutical compositions and, specifically, a pharmaceutical solution comprising a pharmaceutically active ingredient, for example, PERJETA (pertuzumab), ACTEMRA (tocilizumab), KADCYLA (trastuzumab emtansine), MetMAb (onartuzumab), obinutuzumab, ocrelizumab or lebrikizumab.

12 Claims, 4 Drawing Sheets

(56) References Cited

U.S. PATENT DOCUMENTS

| | | |
|---|---|---|
| 5,582,823 A | 12/1996 | Souza |
| 5,605,690 A | 2/1997 | Jacobs et al. |
| 5,656,722 A | 8/1997 | Dorschug |
| 5,721,181 A | 2/1998 | Sehgal et al. |
| 5,736,476 A | 4/1998 | Watzke et al. |
| 5,756,349 A | 5/1998 | Lin |
| 5,824,784 A | 10/1998 | Kinstler et al. |
| 5,854,153 A | 12/1998 | Kohli |
| 5,955,422 A | 9/1999 | Lin |
| RE36,755 E | 6/2000 | Smith et al. |
| 6,096,432 A | 8/2000 | Sakaguchi et al. |
| 6,156,399 A | 12/2000 | Spallek et al. |
| 6,214,429 B1 | 4/2001 | Zou et al. |
| 6,333,285 B1 | 12/2001 | Chopinet et al. |
| 6,472,068 B1 | 10/2002 | Glass et al. |
| 6,518,211 B1 | 2/2003 | Bradshaw et al. |
| 6,561,275 B2 | 5/2003 | Glass et al. |
| 6,599,594 B1 | 7/2003 | Walther et al. |
| 6,630,420 B1 | 10/2003 | Naumann et al. |
| 6,794,323 B2 * | 9/2004 | Peuchert ............... C03C 3/091 501/66 |
| 6,818,576 B2 | 11/2004 | Ikenishi et al. |
| RE38,743 E | 6/2005 | Debrie |
| 6,939,819 B2 | 9/2005 | Usui et al. |
| 7,087,307 B2 | 8/2006 | Nagashima et al. |
| 7,315,125 B2 | 1/2008 | Kass |
| 7,470,999 B2 | 12/2008 | Saito et al. |
| 7,476,652 B2 | 1/2009 | Brunner-Schwarz et al. |
| 7,915,225 B2 | 3/2011 | Finck |
| 8,367,208 B2 | 2/2013 | Glaesemann et al. |
| 8,415,337 B1 | 4/2013 | Krishna |
| 8,518,545 B2 | 8/2013 | Akiba et al. |
| 8,551,898 B2 | 10/2013 | Danielson et al. |
| 8,753,994 B2 | 6/2014 | Danielson et al. |
| 8,756,994 B2 | 6/2014 | Yoneda et al. |
| 8,778,820 B2 | 7/2014 | Gomez et al. |
| 8,980,777 B2 | 3/2015 | Danielson et al. |
| 9,012,343 B2 | 4/2015 | Yamamoto et al. |
| 9,145,329 B2 | 9/2015 | Drake et al. |
| 9,186,295 B2 | 11/2015 | Weeks et al. |
| 9,198,829 B2 | 12/2015 | Weeks et al. |
| 9,241,869 B2 | 1/2016 | Weeks et al. |
| 9,340,447 B2 | 5/2016 | Danielson et al. |
| 2004/0096588 A1 | 5/2004 | Brandt |
| 2006/0008466 A1 | 1/2006 | Elahi et al. |
| 2006/0014670 A1 | 1/2006 | Green et al. |
| 2006/0154891 A1 | 7/2006 | Schridde et al. |
| 2006/0189533 A1 | 8/2006 | Quay et al. |
| 2006/0246004 A1 * | 11/2006 | Adams ............... C07K 16/2887 424/1.49 |
| 2007/0004580 A1 | 1/2007 | Kass |
| 2007/0010700 A1 | 1/2007 | Bensmann et al. |
| 2007/0065366 A1 | 3/2007 | Soliani Raschini et al. |
| 2007/0123410 A1 | 5/2007 | Morena et al. |
| 2007/0157919 A1 | 7/2007 | Marandon |
| 2007/0191207 A1 | 8/2007 | Danielson et al. |
| 2007/0293388 A1 | 12/2007 | Zuyev et al. |
| 2008/0213282 A1 | 9/2008 | Jacob et al. |
| 2008/0281260 A1 | 11/2008 | William et al. |
| 2008/0308444 A1 | 12/2008 | McClain et al. |
| 2009/0131367 A1 | 5/2009 | Gore et al. |
| 2009/0163342 A1 | 6/2009 | Kolberg et al. |
| 2009/0197088 A1 | 8/2009 | Murata |
| 2009/0275462 A1 | 11/2009 | Murata |
| 2009/0291062 A1 | 11/2009 | Fraunhofer et al. |
| 2009/0325776 A1 | 12/2009 | Murata |
| 2010/0034850 A1 | 2/2010 | De Hemptinne et al. |
| 2010/0035038 A1 | 2/2010 | Barefoot et al. |
| 2010/0035745 A1 | 2/2010 | Murata |
| 2010/0047521 A1 | 2/2010 | Amin et al. |
| 2010/0074918 A1 | 3/2010 | Poolman |
| 2010/0120603 A1 | 5/2010 | Morena et al. |
| 2010/0226937 A1 | 9/2010 | Contorni |
| 2010/0255061 A1 | 10/2010 | de Juan, Jr. et al. |
| 2010/0304090 A1 | 12/2010 | Henn et al. |
| 2010/0317506 A1 | 12/2010 | Fechner et al. |
| 2011/0014475 A1 | 1/2011 | Murata |
| 2011/0017297 A1 | 1/2011 | Aitken et al. |
| 2011/0045960 A1 | 2/2011 | Fechner et al. |
| 2011/0045961 A1 | 2/2011 | Dejneka et al. |
| 2011/0062619 A1 | 3/2011 | Laine et al. |
| 2011/0066111 A1 | 3/2011 | Teschner et al. |
| 2011/0071012 A1 | 3/2011 | Kondo et al. |
| 2011/0091704 A1 | 4/2011 | Akiba et al. |
| 2011/0098172 A1 | 4/2011 | Brix |
| 2011/0123832 A1 | 5/2011 | Matsumoto et al. |
| 2011/0135938 A1 | 6/2011 | Kim et al. |
| 2011/0159318 A1 | 6/2011 | Endo et al. |
| 2011/0177987 A1 | 7/2011 | Lenting et al. |
| 2011/0226658 A1 | 9/2011 | Tata-Venkata et al. |
| 2011/0274916 A1 * | 11/2011 | Murata ............... C03C 3/11 428/332 |
| 2011/0281093 A1 | 11/2011 | Gulati et al. |
| 2011/0287046 A1 | 11/2011 | Oloo et al. |
| 2012/0052088 A1 | 3/2012 | Davis et al. |
| 2012/0100329 A1 | 4/2012 | Baratta |
| 2012/0135226 A1 | 5/2012 | Bookbinder et al. |
| 2012/0135853 A1 | 5/2012 | Amin et al. |
| 2012/0148770 A1 | 6/2012 | Rong et al. |
| 2012/0183812 A1 | 7/2012 | Kajita |
| 2012/0199203 A1 | 8/2012 | Nishizawa et al. |
| 2012/0208309 A1 | 8/2012 | Tsujimura et al. |
| 2012/0234368 A1 | 9/2012 | Cintora et al. |
| 2012/0277085 A1 | 11/2012 | Bookbinder et al. |
| 2012/0297829 A1 | 11/2012 | Endo et al. |
| 2013/0004758 A1 | 1/2013 | Dejneka et al. |
| 2013/0011650 A1 | 1/2013 | Akiba et al. |
| 2013/0045375 A1 | 2/2013 | Gross |
| 2013/0101596 A1 | 4/2013 | DeMartino et al. |
| 2013/0101764 A1 | 4/2013 | Schaut et al. |
| 2013/0101766 A1 | 4/2013 | Danielson et al. |
| 2013/0101853 A1 | 4/2013 | Drake et al. |
| 2013/0122284 A1 | 5/2013 | Gross |
| 2013/0196094 A1 | 8/2013 | Weeks et al. |
| 2013/0196095 A1 | 8/2013 | Weeks et al. |
| 2013/0196096 A1 | 8/2013 | Weeks et al. |
| 2013/0196097 A1 | 8/2013 | Weeks et al. |
| 2013/0202823 A1 | 8/2013 | Weeks et al. |
| 2013/0213848 A1 | 8/2013 | Weeks et al. |
| 2013/0216742 A1 | 8/2013 | DeMartino et al. |
| 2013/0344263 A1 | 12/2013 | Danielson et al. |
| 2014/0023865 A1 | 1/2014 | Comte et al. |
| 2014/0120279 A1 | 5/2014 | DeMartino et al. |
| 2014/0154440 A1 | 6/2014 | Iida et al. |
| 2014/0272215 A1 | 9/2014 | Danielson et al. |
| 2014/0339122 A1 | 11/2014 | Weeks et al. |
| 2014/0339125 A1 | 11/2014 | Weeks et al. |
| 2014/0339126 A1 | 11/2014 | Weeks et al. |
| 2014/0341883 A1 | 11/2014 | Weeks et al. |
| 2014/0341888 A1 | 11/2014 | Weeks et al. |
| 2014/0341889 A1 | 11/2014 | Weeks et al. |
| 2014/0341890 A1 | 11/2014 | Weeks et al. |
| 2014/0341891 A1 | 11/2014 | Weeks et al. |
| 2014/0341945 A1 | 11/2014 | Weeks et al. |
| 2014/0342979 A1 | 11/2014 | Weeks et al. |
| 2015/0037571 A1 | 2/2015 | Danielson et al. |
| 2015/0079318 A1 | 3/2015 | Danielson et al. |
| 2015/0157533 A1 | 6/2015 | DeMartino et al. |
| 2015/0232374 A1 | 8/2015 | Danielson et al. |
| 2015/0366756 A1 | 12/2015 | Weeks et al. |
| 2015/0374582 A1 | 12/2015 | Weeks et al. |
| 2016/0095795 A1 | 4/2016 | Weeks et al. |
| 2016/0095796 A1 | 4/2016 | Weeks et al. |

FOREIGN PATENT DOCUMENTS

| | | |
|---|---|---|
| DE | 29702816 U1 | 4/1997 |
| DE | 102004011009 A1 | 9/2005 |
| EP | 0515801 A1 | 12/1992 |
| EP | 1074521 A2 | 2/2001 |
| EP | 2031124 A1 | 3/2009 |
| EP | 2540682 A1 | 1/2013 |
| EP | 2771295 A1 | 9/2014 |
| GB | 966731 A | 8/1964 |

(56) References Cited

FOREIGN PATENT DOCUMENTS

| | | |
|---|---|---|
| GB | 1115972 A | 6/1968 |
| GB | 1334828 A | 10/1973 |
| GB | 2335423 A | 9/1999 |
| IN | 231117 | 3/2009 |
| JP | 7223845 | 8/1995 |
| JP | H09-124338 A | 5/1997 |
| JP | H09-124339 A | 5/1997 |
| JP | H09-241033 A | 9/1997 |
| JP | 11314931 | 11/1999 |
| JP | 2000007372 A | 1/2000 |
| JP | 2001180969 A | 7/2001 |
| JP | 2001192239 A | 7/2001 |
| JP | 2001229526 A | 8/2001 |
| JP | 2001236634 A | 8/2001 |
| JP | 2002003241 A | 1/2002 |
| JP | 2002025762 A | 1/2002 |
| JP | 2002249340 A | 9/202 |
| JP | 2004067443 A | 3/2004 |
| JP | 2004131314 A | 4/2004 |
| JP | 2008195602 A | 8/2008 |
| JP | 2010059038 A | 3/2010 |
| JP | 2010202413 A | 9/2010 |
| JP | 2011093728 A | 5/2011 |
| JP | 2011136895 A | 7/2011 |
| JP | 2012184118 A | 9/2012 |
| KR | 630309 | 5/2006 |
| RO | 83460 A2 | 3/1984 |
| SU | 990700 A1 | 1/1983 |
| WO | WO-9624559 A1 | 8/1996 |
| WO | WO-9725932 A1 | 7/1997 |
| WO | WO-9905070 A1 | 2/1999 |
| WO | WO-2007025932 A2 | 3/2007 |
| WO | WO-2008050500 A1 | 5/2008 |
| WO | WO-2008143999 A1 | 11/2008 |
| WO | WO-2009002660 A2 | 12/2008 |
| WO | WO-2009053947 A2 | 4/2009 |
| WO | WO-2009097123 A1 | 8/2009 |
| WO | WO-2010084670 A1 | 7/2010 |
| WO | WO-2011007785 A1 | 1/2011 |
| WO | WO-2011049146 A1 | 4/2011 |
| WO | WO-2011069338 A1 | 6/2011 |
| WO | WO-2011103798 A1 | 9/2011 |
| WO | WO-2011103799 A1 | 9/2011 |
| WO | WO-2011145661 A1 | 11/2011 |
| WO | WO-2011151760 A2 | 12/2011 |
| WO | WO-2012026290 A1 | 3/2012 |
| WO | WO-2012124757 A1 | 9/2012 |
| WO | WO-2013021975 A1 | 2/2013 |
| WO | WO-2013063275 A1 | 5/2013 |
| WO | WO-2013063277 A1 | 5/2013 |
| WO | WO-2013063280 A1 | 5/2013 |
| WO | WO-2013063283 A1 | 5/2013 |
| WO | WO-2013063287 A1 | 5/2013 |
| WO | WO-2013063290 A1 | 5/2013 |
| WO | WO-2013063292 A1 | 5/2013 |

OTHER PUBLICATIONS

Cortez-Retamozo et al., "Efficient cancer therapy with a nanobody-based conjugate", Cancer Research, Apr. 15, 2004, vol. 64, No. 8, pp. 2853-2857.
Cotes PM, et al., Bio-assay of erythropoietin in mice made polycythaemic by exposure to air at a reduced pressure. Nature. Sep. 9, 1961;191:1065-7.
Database WPI Week 198434 Thomsen Scientific, London, GB; AN 1984-211366 XP002690017.
Davis-Smyth T et al., The second immunoglobulin-like domain of the VEGF tyrosine kinase receptor Flt-1 determines ligand binding and may initiate a signal transduction cascade. EMBO J. Sep. 16, 1996;15(18):4919-27.
Drugs.com, Enbrel, May 28, 2010.
Drugs.com, Neulasta®, Sep. 13, 2010.
Fassina, G., "Complementary peptides as antibody mimetics for protein purification and assay", Immunomethods, Oct. 1994; vol. 5, No. 2, pp. 121-129.
Ferrara N, et al., Vascular endothelial growth factor is essential for corpus luteum angiogenesis. Nat Med. Mar. 1998;4(3):336-40.
Goldwasser E, et al., An assay for erythropoietin in vitro at the milliunit level. Endocrinology. Aug. 1975;97(2):315-23.
Hammond D, et al., Production, utilization and excretion of erythropoietin. I. Chronic anemias. II. Aplastic crisis. 3. Erythropoietic effects of normal plasma. Ann N Y Acad Sci. Mar. 29, 1968;149(1):516-27.
Holash J, et al., VEGF-Trap: a VEGF blocker with potent antitumor effects. Proc Natl Acad Sci U S A. Aug. 20, 2002;99(17):11393-8.
Horton RM et al., Engineering hybrid genes without the use of restriction enzymes: gene splicing by overlap extension. Gene. Apr. 15, 1989;77(1):61-8.
Humana Abbreviated Formulary List of Covered Drugs, 2010 Prescription Drug Guide.
International Search Report & Written Opinion relating to PCT/US2012/061940 filed Oct. 25, 2012; Mail Date: Jan. 30, 2013.
International Search Report & Written Opinion relating to PCT/US2012/061943 filed Oct. 25, 2012; Mail Date: Jan. 30, 2013.
International Search Report & Written Opinion relating to PCT/US2012/061946 filed Oct. 25, 2012; Mail Date: Jan. 30, 2013.
International Search Report & Written Opinion relating to PCT/US2012/061949 filed Oct. 25, 2012; Mail Date: Jan. 30, 2013.
International Search Report & Written Opinion relating to PCT/US2012/061953 filed Oct. 25, 2012; Mail Date: Jan. 30, 2013.
International Search Report & Written Opinion relating to PCT/US2012/061956 filed Oct. 25, 2012; Mail Date: Jan. 30, 2013.
International Search Report & Written Opinion relating to PCT/US2012/061958 filed Oct. 25, 2012; Mail Date: Jan. 30, 2013.
International Search Report relating to PCT/US2013/048589 filed Jun. 28, 2013; Mail Date: Oct. 28, 2013.
International Search Report relating to PCT/US2012/061867; Mail Date: Jan. 30, 2013.
International Search Report relating to PCT/US2012/061939; Mail Date: Jan. 30, 2013.
IPRP & Written Opinion relating to PCT/US2012/061867 filed Oct. 25, 2012; Mail Date: May 8, 2014.
IPRP & Written Opinion relating to PCT/US2012/061939 filed Oct. 25, 2012; Mail Date: May 8, 2014.
IPRP & Written Opinion relating to PCT/US2012/061940 filed Oct. 25, 2012; Mail Date: May 8, 2014.
IPRP & Written Opinion relating to PCT/US2012/061943 filed Oct. 25, 2012; Mail Date: May 8, 2014.
IPRP & Written Opinion relating to PCT/US2012/061946 filed Oct. 25, 2012; Mail Date: May 8, 2014.
IPRP & Written Opinion relating to PCT/US2012/061949 filed Oct. 25, 2012; Mail Date: May 8, 2014.
IPRP & Written Opinion relating to PCT/US2012/061953 filed Oct. 25, 2012; Mail Date: May 8, 2014.
IPRP & Written Opinion relating to PCT/US2012/061956, filed Oct. 25, 2012; Mail date: May 8, 2014.
IPRP & Written Opinion relating to PCT/US2012/061958 filed Oct. 25, 2012; Mail Date: May 8, 2014.
IPRP & Written Opinion relating to PCT/US2013/048589 filed Jun. 28, 2013; Mail Date: Jan. 8, 2015.
Karch, AM, "2006 Lippincott's Nursing Drug Guide," Publisher: Lippincott Williams & Wilkins, ISBN: 1582554382, 2006.
Lane DA, et al., Anticoagulant activities of four unfractionated and fractionated heparins. Thromb Res. Feb. 1978;12(2):257-71.
Lichtlen P, Lam TT, Nork TM, Streit T, Urech DM. Relative contribution of VEGF and TNF-alpha in the cynomolgus laser-induced CNV model: comparing the efficacy of bevacizumab, adalimumab, and SBA105. Invest Ophthalmol Vis Sci. Sep. 2010;51(9):4738-45.
Lytle et al., "Predicted Inactivation of Viruses of Relevance to Biodefense by Solar Radiation," J. Virol. 79(22): 14244-14252 (2005).
Metcalf D. Clonal extinction of myelomonocytic leukemic cells by serum from; mice injected with endotoxin. Int J Cancer. Feb. 15, 1980;25(2):225-33.
Murphy, D. B. and Davidson, M. W., "Differential Interference Contrast (DIC) Microscopy and Modulation Contrast" form Fun-

(56) References Cited

OTHER PUBLICATIONS damentals of Light Microscopy and Electronic Imaging Published 2001, Publisher, Wiley, pp. 153-175.
Nandi et al., "Development and Applications of Varieties of Bioactive Glass Compositions in Dental Surgery, Third Generation Tissue Engineering, Orthopaedic Surgery and as Drug Delivery System," Biomaterial Applications for Nanomedicine, Professor Rosario Pignatello (Ed.), 2011, ISBN: 978-953-307-661-4, InTech, available at cdn.intechopen.com/pdfs/23619/InTech-Development_and_applications_of_varieties_of_bioactive_glass_compositions_in_dental_surgery_third_generation_tissue_engineering_orthopaedic_surgery_and_as_drug_delivery_system.pdf, last accessed Nov. 25, 2015.
Non-Final Office Action mailed Mar. 14, 2013, relating to U.S. Appl. No. 13/660,394, filed Oct. 25, 2012.
Notice of Allowance mailed Jun. 27, 2013, relating to U.S. Appl. No. 13/660,394, filed Oct. 25, 2012.
Pharmaceutical Drug Manufacturers, Erythropoietin Injection, Sep. 18, 2008.
Randle PJ., "Assay of plasma insulin activity by the rat-diaphragm method", British Medical Journal, May 29, 1954, vol. 1 (4873), pp. 1237-1240.
Reynolds et al., "Glass Delamination and Breakage", Bioprocess International, Dec. 1, 2011, vol. 9, No. 11, pp. 52-57.
Ribel U, Subcutaneous absorption of insulin analogues. In Frontiers in Insulin Pharmacology, Berger M, Gries FA (eds), Thieme Verlag, pp. 70-77 (1993).
Ribel U., et al., The pig as a model for subcutaneous insulin absorption in man. Serrano_Rios, M and Lefebvre, P.J. 891-896. 1985. Amsterdam; New York; Oxford, Elsevier Science Publishers. 1985 (Conference Proceeding).
Roche Consumer Medicine Information, Neupogen®, Feb. 3, 2010.
Saragovi et al., "Design and synthesis of a mimetic from an antibody complementarity-determining region", Science, Aug. 16, 1991, vol. 253, No. 5021, pp. 792-795.
Silva M, et al., Erythropoietin can induce the expression of bcl-x(L) through Stat5 in erythropoietin-dependent progenitor cell lines. J Biol Chem. Aug. 6, 1999;274(32):22165-9.
Tarrant, "Production and Properties of Glass Containers," Journal of the Society for Cosmetic Chemists, vol. 13, No. 1:15-42 (1962).
Teien AN, et al., Evaluation of an amidolytic heparin assay method: increased sensitivity by adding purified antithrombin III. Thromb Res. Mar. 1977;10(3):399-410.
Ternant D, et al., An enzyme-linked immunosorbent assay for therapeutic drug monitoring of infliximab. Ther Drug Monit. Apr. 2006;28(2):169-74.
U.S. Food and Drug Administration, Package Insert HUMIRA (adalimumab) Abbott Laboratories, 2010.
Ueda et al., "Age-dependent changes in phenotypes and candidate gene analysis in a polygenic animal model of Type II diabetes mellitus; NSY mouse" Diabetologia, Jul. 2000, vol. 43, Issue 7, pp. 932-938.
Veer et al., "The strength of glass, a nontransparent value," HERON vol. 52, No. 1/2, pp. 87-104 (2007).
Wen, Zai-Qing et al., "Nondestructive detection of glass vial inner surface morphology with differential interference contrast microscopy", Journal of Pharmaceutical Sciences, Apr. 2012, vol. 101, Issue 4, pp. 1378-1384.
Yu L et al., Interaction between bevacizumab and murine VEGF-A: a reassessment. Invest Ophthalmol Vis Sci. Feb. 2008;49(2):522-7.
Lucentis product information, Novartis, 2007, p. 1-35.
Ciullo, PA, "Industrial Minerals and Their Uses—A Handbook & Formulary," William Andrew Publishing/Noyes, Westwood, New Jersey, 1996, Chapter 11: Ceramics and Glass, pp. 459-463.
[No Author Listed] European Pharmacopeia, 5th edition, Council of Europe, Jul. 2004, Preface pp. i-iii and Section 3.2 Containers, p. 303.
[No Author Listed] U.S. Pharmacopeial Convention Medicines Compendium, Monographs, Section 660, Containers—Glass, retrieved from mc.usp.org/general-chapters, 5 pages, last accessed Aug. 21, 2014.
Varshneya, A. K., "Chemical Strengthening of Glass: Lessons Learned and Yet To Be Learned", International Journal of Applied Glass Science 1 [2] 131-142 (2010).
Gomez, et al., "A look at the chemical strengthening process: alkali aluminosilicate glasses vs. soda-lime glass," 71st Conference on Glass Problems, Editro: Charles H. Drummond, III, The American Society, 2011, p. 62-66.
International Search Report & Written Opinion relating to PCT/US2012/061911 filed Oct. 25, 2012; Mail Date: Jan. 30, 2013.
International Search Report & Written Opinion relating to PCT/US2013/028184 filed Feb. 28, 2013; Mail Date: Jul. 11, 2013.
IPRP & Written Opinion relating to PCT/US2013/028184 filed Feb. 28, 2013; Mail Date: Sep. 12, 2014.

* cited by examiner

DELAMINATION RESISTANT PHARMACEUTICAL GLASS CONTAINERS CONTAINING ACTIVE PHARMACEUTICAL INGREDIENTS

CROSS REFERENCE TO RELATED APPLICATIONS

The present application claims priority to U.S. Provisional Application No. 61/815,696, filed Apr. 24, 2013, entitled "Delamination Resistant Pharmaceutical Glass Containers Containing Active Pharmaceutical Ingredients", the entirety of which is hereby incorporated by reference herein.

FIELD OF THE INVENTION

The present specification generally relates to pharmaceutical containers and, more specifically, to chemically and mechanically durable pharmaceutical containers that are delamination resistant and formed, at least in part, of a glass composition.

BACKGROUND

The design of a packaged pharmaceutical composition generally seeks to provide an active pharmaceutical ingredient (API) in a suitable package that is convenient to use, that maintains the stability of the API over prolonged storage, and that ultimately allows for the delivery of efficacious, stable, active, nontoxic and nondegraded API.

Most packaged formulations are complex physico-chemical systems, through which the API is subject to deterioration by a variety of chemical, physical, and microbial reactions. Interactions between drugs, adjuvants, containers, and/or closures may occur, which can lead to the inactivation, decomposition and/or degradation of the API.

Historically, glass has been used as the preferred material for packaging pharmaceuticals because of its hermeticity, optical clarity and excellent chemical durability relative to other materials. Specifically, the glass used in pharmaceutical packaging must have adequate chemical durability so as not to affect the stability of the pharmaceutical compositions contained therein. Glasses having suitable chemical durability include those glass compositions within the ASTM standard 'Type 1B' glass compositions which have a proven history of chemical durability.

However, use of glass for such applications is limited by the mechanical performance of the glass. Specifically, in the pharmaceutical industry, glass breakage is a safety concern for the end user as the broken package and/or the contents of the package may injure the end user. Further, non-catastrophic breakage (i.e., when the glass cracks but does not break) may cause the contents to lose their sterility which, in turn, may result in costly product recalls.

One approach to improving the mechanical durability of the glass package is to thermally temper the glass package. Thermal tempering strengthens glass by inducing a surface compressive stress during rapid cooling after forming. This technique works well for glass articles with flat geometries (such as windows), glass articles with thicknesses >2 mm, and glass compositions with high thermal expansion. However, pharmaceutical glass packages typically have complex geometries (vial, tubular, ampoule, etc.), thin walls (~1-1.5 mm), and are produced from low expansion glasses (30-55× $10^{-7} K^{-1}$) making glass pharmaceutical packages unsuitable for strengthening by thermal tempering.

Chemical tempering also strengthens glass by the introduction of surface compressive stress. The stress is introduced by submerging the article in a molten salt bath. As ions from the glass are replaced by larger ions from the molten salt, a compressive stress is induced in the surface of the glass. The advantage of chemical tempering is that it can be used on complex geometries, thin samples, and is relatively insensitive to the thermal expansion characteristics of the glass substrate. However, glass compositions which exhibit a moderate susceptibility to chemical tempering generally exhibit poor chemical durability and vice-versa.

Finally, glass compositions commonly used in pharmaceutical packages, e.g., Type 1a and Type 1b glass, further suffer from a tendency for the interior surfaces of the pharmaceutical package to shed glass particulates or "delaminate" following exposure to pharmaceutical solutions. Such delamination often destabilizes the active pharmaceutical ingredient (API) present in the solution, thereby rendering the API therapeutically ineffective or unsuitable for therapeutic use.

Delamination has caused the recall of multiple drug products over the last few years (see, for example, Reynolds et al., (2011) *BioProcess International* 9(11) pp. 52-57). In response to the growing delamination problem, the U.S. Food and Drug Administration (FDA) has issued an advisory indicating that the presence of glass particulate in injectable drugs can pose a risk.

The advisory states that, "[t]here is potential for drugs administered intravenously that contain these fragments to cause embolic, thrombotic and other vascular events; and subcutaneously to the development of foreign body granuloma, local injections site reactions and increased immunogenicity."

Accordingly, a recognized need exists for alternative glass containers for packaging of pharmaceutical compositions which exhibit a reduced propensity to delaminate.

SUMMARY

In one aspect, the present invention is directed to a delamination resistant pharmaceutical container formed, at least in part, of a glass composition including from about 70 mol. % to about 80 mol. % $SiO_2$; from about 3 mol. % to about 13 mol. % alkaline earth oxide; X mol. % $Al_2O_3$; and Y mol. % alkali oxide, wherein the alkali oxide includes $Na_2O$ in an amount greater than about 8 mol. %, wherein the ratio of Y:X is greater than 1, and the glass composition is free of boron and compounds of boron.

In one embodiment, the $SiO_2$ is present in an amount less than or equal to 78 mol. %.

In one embodiment, the amount of the alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) that is less than or equal to 0.5. In a particular embodiment, the alkaline earth oxide includes from about 0.1 mol. % to less than or equal to about 1.0 mol. % CaO. In a particular embodiment, the alkaline earth oxide includes from about 3 mol. % to about 7 mol. % MgO.

In another embodiment, the alkali oxide includes greater than or equal to about 9 mol. % $Na_2O$ and less than or equal to about 15 mol. % $Na_2O$. In another embodiment, the alkali oxide further includes $K_2O$ in an amount less than or equal to about 3 mol. %. In a particular embodiment, the alkali oxide includes $K_2O$ in an amount greater than or equal to about 0.01 mol. % and less than or equal to about 1.0 mol. %.

In one embodiment, X is greater than or equal to about 2 mol. % and less than or equal to about 10 mol. %. In a particular embodiment, the ratio of Y:X is less than or equal to 2. In a particular embodiment, the ratio of Y:X is greater than or equal to 1.3 and less than or equal to 2.0.

In another embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 μm and a surface compressive stress greater than or equal to 250 MPa.

In another aspect, the present invention provides a delamination resistant pharmaceutical container formed, at least in part, of a glass composition including from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %.; and Y mol. % alkali oxide, wherein the alkali oxide includes $Na_2O$ in an amount greater than or equal to about 9 mol. % and less than or equal to about 15 mol. %, wherein the ratio of Y:X is greater than 1, and the glass composition is free of boron and compounds of boron.

In a particular embodiment, the ratio of Y:X is less than or equal to about 2. In a particular embodiment, the ratio of Y:X is greater than or equal to about 1.3 and less than or equal to about 2.0.

In one embodiment, the alkaline earth oxide includes MgO and CaO and has a ratio (CaO (mol. %)/(CaO (mol. %)+MgO (mol. %))) less than or equal to 0.5.

In another embodiment, the alkali oxide includes $K_2O$ in an amount greater than or equal to about 0.01 mol. % and less than or equal to about 1.0 mol. %.

In another aspect, the present invention provides a delamination resistant pharmaceutical container formed, at least in part, of a glass composition including from about 68 mol. % to about 80 mol. % $SiO_2$; from about 3 mol. % to about 13 mol. % alkaline earth oxide; X mol. % $Al_2O_3$; Y mol. % alkali oxide, wherein the alkali oxide includes $Na_2O$ in an amount greater than about 8 mol. %; and $B_2O_3$, wherein the ratio ($B_2O_3$ (mol. %)/(Y mol. %–X mol. %) is greater than 0 and less than 0.3, and the ratio of Y:X is greater than 1.

In one embodiment, the amount of $SiO_2$ is greater than or equal to about 70 mol. %.

In one embodiment, the amount of alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) less than or equal to 0.5. In a particular embodiment, the alkaline earth oxide includes CaO in an amount greater than or equal to about 0.1 mol. % and less than or equal to about 1.0 mol. %. In a particular embodiment, the alkaline earth oxide includes from about 3 mol. % to about 7 mol. % MgO.

In one embodiment, the alkali oxide is greater than or equal to about 9 mol. % $Na_2O$ and less than or equal to about 15 mol. % $Na_2O$. In a particular embodiment, the alkali oxide further includes $K_2O$ in a concentration less than or equal to about 3 mol. %.

In another embodiment, the alkali oxide further includes $K_2O$ in a concentration greater than or equal to about 0.01 mol. % and less than or equal to about 1.0 mol. %.

In another embodiment, the pharmaceutical container has a ratio ($B_2O_3$ (mol. %)/(Y mol. %–X mol. %) less than 0.2. In a particular embodiment, the amount of $B_2O_3$ is less than or equal to about 4.0 mol. %. In another embodiment, the amount of $B_2O_3$ is greater than or equal to about 0.01 mol. %.

In one embodiment, X is greater than or equal to about 2 mol. % and less than or equal to about 10 mol. %. In a particular embodiment, the ratio of Y:X is less than or equal to 2. In another embodiment, the ratio of Y:X is greater than 1.3.

In one embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 μm and a surface compressive stress greater than or equal to 250 MPa.

In one embodiment of any of the foregoing aspects of the invention, the pharmaceutical container further includes a pharmaceutical composition having an active pharmaceutical ingredient. In a particular embodiment, the pharmaceutical composition includes a citrate or phosphate buffer, for example, sodium citrate, SSC, monosodium phosphate or disodium phosphate. Alternatively or in addition, the pharmaceutical composition has a pH between about 7 and about 11, between about 7 and about 10, between about 7 and about 9, or between about 7 and about 8.

In one embodiment of any of the foregoing aspects of the invention, the active pharmaceutical ingredient is recombinant humanized monoclonal antibody that targets the extracellular dimerization domain (Subdomain II) of the human epidermal growth factor receptor 2 protein (HER2). In one embodiment, the pharmaceutical composition is pertuzumab (PERJETA™).

In one embodiment of any of the foregoing aspects of the invention, the active pharmaceutical ingredient is a humanized anti-human interleukin-6 (IL-6) receptor antibody. In a particular embodiment, the pharmaceutical composition is tocilizumab (ACTEMRA®).

In one embodiment of any of the foregoing aspects of the invention, the active pharmaceutical ingredient is a HER2-targeted antibody and microtubule inhibitor conjugate, e.g., trastuzumab linked to mertansine. In a particular embodiment, the pharmaceutical composition is ado-trastuzumab emtansine (KADCYLA).

In one embodiment of any of the foregoing aspects of the invention, the active pharmaceutical ingredient is an anti-Met monoclonal antibody. In a particular embodiment, the pharmaceutical composition is onartuzumab (MetMAb).

In one embodiment of any of the foregoing aspects of the invention, the active pharmaceutical ingredient is a humanized anti-CD20 monoclonal antibody. In a particular embodiment, the pharmaceutical composition is obinutuzumab. In another embodiment, the pharmaceutical composition is ocrelizumab.

In one embodiment of any of the foregoing aspects of the invention, the active pharmaceutical ingredient is a humanized anti-interleukin-13 (IL-13) monoclonal antibody. In a particular embodiment, the pharmaceutical composition is lebrikizumab.

In a particular aspect, the present invention provides a delamination resistant pharmaceutical container formed, at least in part, of a glass composition including about 76.8 mol. % $SiO_2$; about 6.0 mol. % $Al_2O_3$; about 11.6 mol. % $Na_2O$; about 0.1 mol. % $K_2O$; about 4.8 mol. % MgO; and about 0.5 mol. % CaO, wherein the glass composition is free of boron and compounds of boron; and wherein the pharmaceutical container further comprises a pharmaceutical composition selected from the group consisting of PERJETA (pertuzumab), ACTEMRA (tocilizumab), KADCYLA (trastuzumab emtansine), MetMAb (onartuzumab), obinutuzumab, ocrelizumab and lebrikizumab.

In one aspect, the present invention includes a delamination resistant pharmaceutical container including a glass composition. The pharmaceutical container includes from about 70 mol. % to about 80 mol. % SiO2; from about 3 mol. % to about 13 mol. % alkaline earth oxide; X mol. % Al2O3; and Y mol. % alkali oxide. The alkali oxide includes Na2O in an amount greater than about 8 mol. %, a ratio of Y:X is greater than 1, and the glass composition is free of boron and compounds of boron. The delamination resistant pharmaceutical container further includes an active pharmaceutical ingredient.

In one or more embodiments, the SiO2 is present in an amount less than or equal to 78 mol. %. In some embodiments, an amount of the alkaline earth oxide is greater than or equal to about 4 mol. % and less than or equal to about 8 mol. %. In one or more embodiments, the alkaline earth oxide includes MgO and CaO and a ratio (CaO (mol. %)/(CaO (mol. %)+MgO (mol. %))) is less than or equal to 0.5. In one or more embodiments, the alkaline earth oxide includes from about 0.1 mol. % to less than or equal to about 1.0 mol. % CaO. In one or more embodiments, the alkaline earth oxide includes from about 3 mol. % to about 7 mol. % MgO. In one or more embodiments, X is greater than or equal to about 2 mol. % and less than or equal to about 10 mol. %. In embodiments, the alkali oxide includes greater than or equal to about 9 mol. % Na2O and less than or equal to about 15 mol. % Na2O. In some embodiments, the ratio of Y:X is less than or equal to 2. In one or more embodiments, the ratio of Y:X is greater than or equal to 1.3 and less than or equal to 2.0. In one or more embodiments, the alkali oxide further includes K2O in an amount less than or equal to about 3 mol. %. In one or more embodiments, the glass composition is free of phosphorous and compounds of phosphorous. In one or more embodiments, the alkali oxide includes K2O in an amount greater than or equal to about 0.01 mol. % and less than or equal to about 1.0 mol. %.

In another aspect, the invention includes a delamination resistant pharmaceutical container including a pharmaceutical composition. The pharmaceutical container includes an active pharmaceutical ingredient, such that the pharmaceutical container includes a glass composition including SiO2 in a concentration greater than about 70 mol. %; alkaline earth oxide including MgO and CaO, wherein CaO is present in an amount greater than or equal to about 0.1 mol. % and less than or equal to about 1.0 mol. %, and a ratio (CaO (mol. %)/(CaO (mol. %)+MgO (mol. %))) is less than or equal to 0.5; and Y mol. % alkali oxide, wherein the alkali oxide includes Na2O in an amount greater than about 8 mol. %, such that the glass composition is free of boron and compounds of boron.

In another aspect, the invention includes a delamination resistant pharmaceutical container including a pharmaceutical composition including an active pharmaceutical ingredient. The pharmaceutical container includes a glass composition including from about 72 mol. % to about 78 mol. % SiO2; from about 4 mol. % to about 8 mol. % alkaline earth oxide, wherein the alkaline earth oxide includes MgO and CaO and a ratio (CaO (mol. %)/(CaO (mol. %)+MgO (mol. %))) is less than or equal to 0.5; X mol. % Al2O3, such that X is greater than or equal to about 4 mol. % and less than or equal to about 8 mol. %.; and Y mol. % alkali oxide, such that the alkali oxide includes Na2O in an amount greater than or equal to about 9 mol. % and less than or equal to about 15 mol. %, a ratio of Y:X is greater than 1, and the glass composition is free of boron and compounds of boron.

In another aspect, the invention includes a delamination resistant pharmaceutical container including a pharmaceutical composition including an active pharmaceutical ingredient. The pharmaceutical container includes a glass composition. The glass composition includes from about 70 mol. % to about 80 mol. % SiO2; from about 3 mol. % to about 13 mol. % alkaline earth oxide, such that the alkaline earth oxide includes CaO in an amount greater than or equal to about 0.1 mol. % and less than or equal to about 1.0 mol. %, MgO, and a ratio (CaO (mol. %)/(CaO (mol. %)+MgO (mol. %))) is less than or equal to 0.5; X mol. % Al2O3, wherein X is greater than or equal to about 2 mol. % and less than or equal to about 10 mol. %; and Y mol. % alkali oxide, wherein the alkali oxide includes from about 0.01 mol. % to about 1.0 mol. % K2O and a ratio of Y:X is greater than 1, and the glass composition is free of boron and compounds of boron.

In one or more embodiments of any of the above aspects, the pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab.

In one aspect, the present invention includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container including an internal homogeneous layer.

In one or more embodiments, the pharmaceutical container has a compressive stress greater than or equal to 150 MPa. In one or more embodiments, the pharmaceutical container has a compressive stress greater than or equal to 250 MPa. In one or more embodiments, the pharmaceutical container includes a depth of layer greater than 30 μm. In one or more embodiments, the depth of layer is greater than 35 μm. In one or more embodiments, the pharmaceutical composition demonstrates increased stability, product integrity, or efficacy.

In one aspect, the present invention includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container including an internal homogeneous layer having a compressive stress greater than 150.

In one or more embodiments, the pharmaceutical container includes a depth of layer greater than 10 μm. In one or more embodiments, the pharmaceutical container includes a depth of layer greater than 25 μm. In one or more embodiments, the pharmaceutical container includes a depth of layer greater than 30 μm. In one or more embodiments, the pharmaceutical container has a compressive stress greater than or equal to 300 MPa. In one or more embodiments, the pharmaceutical container includes increased stability, product integrity, or efficacy.

In another aspect, the present technology includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container having a compressive stress greater than or equal to 150 MPa and a depth of layer greater than 10 μm, and such that the pharmaceutical composition demonstrates increased stability, product integrity, or efficacy.

In another aspect, the present technology includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container including a substantially homogeneous inner layer, and such that the pharmaceutical composition demonstrates increased stability, product integrity, or efficacy.

In another aspect, the present technology includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container having a delamination factor of less than 3, wherein the pharmaceutical composition demonstrates increased stability, product integrity, or efficacy.

In another aspect, the present technology includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container which is substantially free of boron, and such that the pharmaceutical composition demonstrates increased stability, product integrity, or efficacy.

In one or more embodiments, the glass pharmaceutical container has a compressive stress greater than or equal to 150 MPa and a depth of layer greater than 25 μm. In one or more embodiments, the glass pharmaceutical container has a compressive stress greater than or equal to 300 MPa and a depth of layer greater than 35 μm. In one or more embodiments, the glass pharmaceutical container includes a substantially homogeneous inner layer. In one or more embodiments, the glass pharmaceutical container has a compressive stress greater than or equal to 150 MPa and a depth of layer greater than 25 μm.

In another aspect, the present technology includes a pharmaceutical composition. The pharmaceutical composition includes PERJETA (pertuzumab), ACTEMRA (tocilizumab), KADCYLA (trastuzumab emtansine), MetMAb (onartuzumab), obinutuzumab, ocrelizumab or lebrikizumab and a pharmaceutically acceptable excipient, such that the pharmaceutical composition is contained within a glass pharmaceutical container including a delamination factor of less than 3, and such that the pharmaceutical composition includes increased stability, product integrity, or efficacy.

In one or more embodiments of any of the above aspects, the container has a compressive stress greater than or equal to 300 MPa. In one or more embodiments, the container has a depth of layer greater than 25 μm. In one or more embodiments, the container has a depth of layer greater than 30 μm. In one or more embodiments, the container has a depth of layer of at least 35 μm. In one or more embodiments, the container has a compressive stress greater than or equal to 300 MPa. In one or more embodiments, the container has a compressive stress greater than or equal to 350 MPa.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
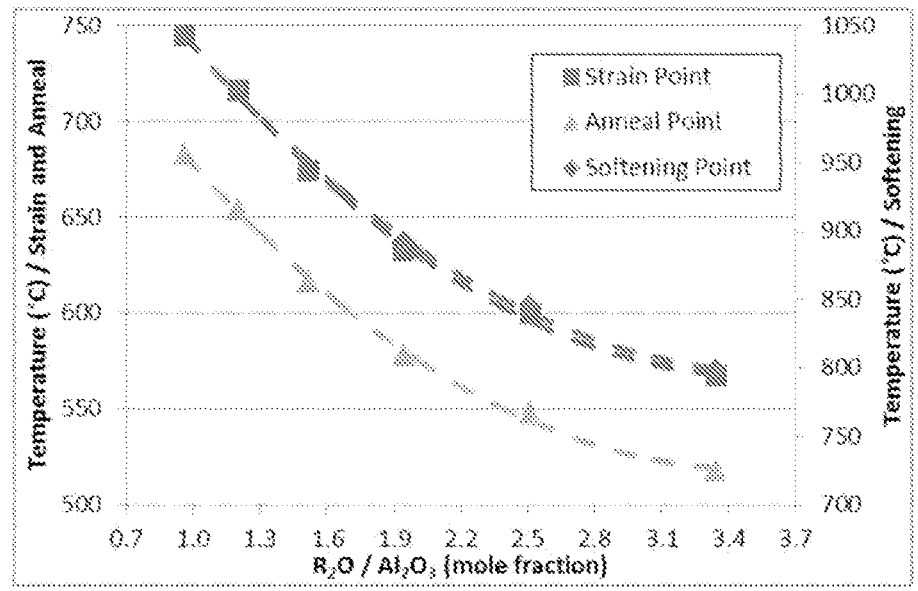
FIG. 1 graphically depicts the relationship between the ratio of alkali oxides to alumina (x-axis) and the strain point, annealing point, and softening point (y-axes) of inventive and comparative glass compositions.

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage, maintenance and/or delivery of therapeutically efficacious pharmaceutical compositions and, in particular pharmaceutical solutions comprising active pharmaceutical ingredients, for example, PERJETA (pertuzumab), ACTEMRA (tocilizumab), KADCYLA (trastuzumab emtansine), MetMAb (onartuzumab), obinutuzumab, ocrelizumab and lebrikizumab.

Conventional glass containers or glass packages for containing pharmaceutical compositions are generally formed from glass compositions which are known to exhibit chemical durability and low thermal expansion, such as alkali borosilicate glasses. While alkali borosilicate glasses exhibit good chemical durability, container manufacturers have sporadically observed silica-rich glass flakes dispersed in the solution contained in the glass containers as a result of delamination, particularly when the solution has been stored in direct contact with the glass surface for long time periods (months to years).

Delamination refers to a phenomenon in which glass particles are released from the surface of the glass following a series of leaching, corrosion, and/or weathering reactions. In general, the glass particles are silica-rich flakes of glass which originate from the interior surface of the package as a result of the leaching of modifier ions into a solution contained within the package. These flakes may generally be from about 1 nm to 2 μm thick with a width greater than about 50 μm.

It has heretofore been hypothesized that delamination is due to the phase separation which occurs in alkali borosilicate glasses when the glass is exposed to the elevated temperatures used for reforming the glass into a container shape.

However, it is now believed that the delamination of the silica-rich glass flakes from the interior surfaces of the glass containers is due to the compositional characteristics of the glass container in its as-formed condition. Specifically, the high silica content of alkali borosilicate glasses increases the melting temperature of the glass. However, the alkali and borate components in the glass composition melt and/or vaporize at much lower temperatures. In particular, the borate species in the glass are highly volatile and evaporate from the surface of the glass at the high temperatures necessary to melt and form the glass.

Specifically, glass stock is reformed into glass containers at high temperatures and in direct flames. The high temperatures cause the volatile borate species to evaporate from portions of the surface of the glass. When this evaporation occurs within the interior volume of the glass container, the volatilized borate species are re-deposited in other areas of the glass causing compositional heterogeneities in the glass container, particularly with respect to the bulk of the glass container. For example, as one end of a glass tube is closed to form the bottom or floor of the container, borate species may evaporate from the bottom portion of the tube and be re-deposited elsewhere in the tube. As a result, the areas of the container exposed to higher temperatures have silica-rich surfaces. Other areas of the container which are amenable to boron deposition may have a silica-rich surface with a boron-rich layer below the surface. Areas amenable to boron deposition are at a temperature greater than the anneal point of the glass composition but less than the hottest temperature the glass is subjected to during reformation when the boron is incorporated into the surface of the glass. Solutions contained in the container may leach the boron from the boron-rich layer. As the boron-rich layer is leached from the glass, the silica-rich surface begins to spall, shedding silica-rich flakes into the solution.

DEFINITIONS

The term "softening point," as used herein, refers to the temperature at which the viscosity of the glass composition is $1 \times 10^{7.6}$ poise.

The term "annealing point," as used herein, refers to the temperature at which the viscosity of the glass composition is $1 \times 10^{13}$ poise.

The terms "strain point" and "$T_{strain}$," as used herein, refers to the temperature at which the viscosity of the glass composition is $3 \times 10^{14}$ poise.

The term "CTE," as used herein, refers to the coefficient of thermal expansion of the glass composition over a temperature range from about room temperature (RT) to about 300° C.

In the embodiments of the glass compositions described herein, the concentrations of constituent components (e.g., $SiO_2$, $Al_2O_3$, and the like) are specified in mole percent (mol. %) on an oxide basis, unless otherwise specified.

The terms "free" and "substantially free," when used to describe the concentration and/or absence of a particular constituent component in a glass composition, means that the constituent component is not intentionally added to the glass composition. However, the glass composition may contain traces of the constituent component as a contaminant or tramp in amounts of less than 0.01 mol. %.

The term "chemical durability," as used herein, refers to the ability of the glass composition to resist degradation upon exposure to specified chemical conditions. Specifically, the chemical durability of the glass compositions described herein was assessed according to three established material testing standards: DIN 12116 dated March 2001 and entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; and ISO 720: 1985 entitled "Glass—Hydrolytic resistance of glass grains at 121 degrees C.—Method of test and classification." The chemical durability of the glass may also be assessed according to ISO 719:1985 "Glass—Hydrolytic resistance of glass grains at 98 degrees C.—Method of test and classification," in addition to the above referenced standards. The ISO 719 standard is a less rigorous version of the ISO 720 standard and, as such, it is believed that a glass which meets a specified classification of the ISO 720 standard will also meet the corresponding classification of the ISO 719 standard. The classifications associated with each standard are described in further detail herein.

Glass Compositions

Reference will now be made in detail to various embodiments of pharmaceutical containers formed, at least in part, of glass compositions which exhibit improved chemical and mechanical durability and, in particular, improved resistance to delamination. The glass compositions may also be chemically strengthened thereby imparting increased mechanical durability to the glass. The glass compositions described herein generally comprise silica ($SiO_2$), alumina ($Al_2O_3$), alkaline earth oxides (such as MgO and/or CaO), and alkali oxides (such as $Na_2O$ and/or $K_2O$) in amounts which impart chemical durability to the glass composition. Moreover, the alkali oxides present in the glass compositions facilitate chemically strengthening the glass compositions by ion exchange. Various embodiments of the glass compositions will be described herein and further illustrated with reference to specific examples.

The glass compositions described herein are alkali aluminosilicate glass compositions which generally include a combination of $SiO_2$, $Al_2O_3$, at least one alkaline earth oxide, and one or more alkali oxides, such as $Na_2O$ and/or $K_2O$. In some embodiments, the glass compositions may be free from boron and compounds containing boron. The combination of these components enables a glass composition which is resistant to chemical degradation and is also suitable for chemical strengthening by ion exchange. In some embodiments the glass compositions may further comprise minor amounts of one or more additional oxides such as, for example, $SnO_2$, $ZrO_2$, ZnO, $TiO_2$, $As_2O_3$ or the like. These components may be added as fining agents and/or to further enhance the chemical durability of the glass composition.

In the embodiments of the glass compositions described herein $SiO_2$ is the largest constituent of the composition and, as such, is the primary constituent of the resulting glass network. $SiO_2$ enhances the chemical durability of the glass and, in particular, the resistance of the glass composition to decomposition in acid and the resistance of the glass composition to decomposition in water. Accordingly, a high $SiO_2$ concentration is generally desired. However, if the content of $SiO_2$ is too high, the formability of the glass may be diminished as higher concentrations of $SiO_2$ increase the difficulty of melting the glass which, in turn, adversely impacts the formability of the glass. In the embodiments described herein, the glass composition generally comprises $SiO_2$ in an amount greater than or equal to 67 mol. % and less than or equal to about 80 mol. % or even less than or equal to 78 mol. %. In some embodiments, the amount of $SiO_2$ in the glass composition may be greater than about 68 mol. %, greater than about 69 mol. % or even greater than about 70 mol. %. In some other embodiments, the amount of $SiO_2$ in the glass composition may be greater than 72 mol. %, greater than 73 mol. % or even greater than 74 mol. %. For example, in some embodiments, the glass composition may include from about 68 mol. % to about 80 mol. % or even to about 78 mol. % $SiO_2$. In some other embodiments the glass composition may include from about 69 mol. % to about 80 mol. % or even to about 78 mol. % $SiO_2$. In some other embodiments the glass composition may include from about 70 mol. % to about 80 mol. % or even to about 78 mol. % $SiO_2$. In still other embodiments, the glass composition comprises $SiO_2$ in an amount greater than or equal to 70 mol. % and less than or equal to 78 mol. %. In some embodiments, $SiO_2$ may be present in the glass composition in an amount from about 72 mol. % to about 78 mol. %. In some other embodiments, $SiO_2$ may be present in the glass composition in an amount from about 73 mol. % to about 78 mol. %. In other embodiments, $SiO_2$ may be present in the glass composition in an amount from about 74 mol. % to about 78 mol. %. In still other embodiments, $SiO_2$ may be present in the glass composition in an amount from about 70 mol. % to about 76 mol. %.

The glass compositions described herein further include $Al_2O_3$. $Al_2O_3$, in conjunction with alkali oxides present in the glass compositions such as $Na_2O$ or the like, improves the susceptibility of the glass to ion exchange strengthening. In the embodiments described herein, $Al_2O_3$ is present in the glass compositions in X mol. % while the alkali oxides are present in the glass composition in Y mol. %. The ratio Y:X in the glass compositions described herein is greater than 1 in order to facilitate the aforementioned susceptibility to ion exchange strengthening. Specifically, the diffusion coefficient or diffusivity D of the glass composition relates to the rate at which alkali ions penetrate into the glass surface during ion exchange. Glasses which have a ratio Y:X greater than about 0.9 or even greater than about 1 have a greater diffusivity than glasses which have a ratio Y:X less than 0.9. Glasses in which the alkali ions have a greater diffusivity can obtain a greater depth of layer for a given ion exchange time and ion exchange temperature than glasses in which the alkali ions have a lower diffusivity. Moreover, as the ratio of Y:X increases, the strain point, anneal point, and softening point of the glass decrease, such that the glass is more readily formable. In addition, for a given ion exchange time and ion exchange temperature, it has been found that compressive stresses induced in glasses which have a ratio Y:X greater than about 0.9 and less than or equal to 2 are generally greater than those generated in glasses in which the ratio Y:X is less than 0.9 or greater than 2. Accordingly, in some embodiments, the ratio of Y:X is greater than 0.9 or even greater than 1. In some embodiments, the ratio of Y:X is greater than 0.9, or even greater than 1, and less than or equal to about 2. In still other embodiments, the ratio of Y:X may be greater than or equal to about 1.3 and less than or equal to about 2.0 in order to maximize the amount of compressive stress induced in the glass for a specified ion exchange time and a specified ion exchange temperature.

However, if the amount of $Al_2O_3$ in the glass composition is too high, the resistance of the glass composition to acid attack is diminished. Accordingly, the glass compositions described herein generally include $Al_2O_3$ in an amount greater than or equal to about 2 mol. % and less than or equal to about 10 mol. %. In some embodiments, the amount of $Al_2O_3$ in the glass composition is greater than or equal to about 4 mol. % and less than or equal to about 8 mol. %. In some other embodiments, the amount of $Al_2O_3$ in the glass composition is greater than or equal to about 5 mol. % to less than or equal to about 7 mol. %. In some other embodiments, the amount of $Al_2O_3$ in the glass composition is greater than or equal to about 6 mol. % to less than or equal to about 8 mol. %. In still other embodiments, the amount of $Al_2O_3$ in the glass composition is greater than or equal to about 5 mol. % to less than or equal to about 6 mol. %.

The glass compositions also include one or more alkali oxides such as $Na_2O$ and/or $K_2O$. The alkali oxides facilitate the ion exchangeability of the glass composition and, as such, facilitate chemically strengthening the glass. The alkali oxide may include one or more of $Na_2O$ and $K_2O$. The alkali oxides are generally present in the glass composition in a total concentration of Y mol. %. In some embodiments described herein, Y may be greater than about 2 mol. % and less than or equal to about 18 mol. %. In some other embodiments, Y may be greater than about 8 mol. %, greater than about 9 mol. %, greater than about 10 mol. % or even greater than about 11 mol. %. For example, in some embodiments described herein Y is greater than or equal to about 8 mol. % and less than or equal to about 18 mol. %. In still other embodiments, Y may be greater than or equal to about 9 mol. % and less than or equal to about 14 mol. %.

The ion exchangeability of the glass composition is primarily imparted to the glass composition by the amount of the alkali oxide $Na_2O$ initially present in the glass composition prior to ion exchange. Accordingly, in the embodiments of the glass compositions described herein, the alkali oxide present in the glass composition includes at least $Na_2O$. Specifically, in order to achieve the desired compressive strength and depth of layer in the glass composition upon ion exchange strengthening, the glass compositions include $Na_2O$ in an amount from about 2 mol. % to about 15 mol. % based on the molecular weight of the glass composition. In some embodiments the glass composition includes at least about 8 mol. % of $Na_2O$ based on the molecular weight of the glass composition. For example, the concentration of $Na_2O$ may be greater than 9 mol. %, greater than 10 mol. % or even greater than 11 mol. %. In some embodiments, the concentration of $Na_2O$ may be greater than or equal to 9 mol. % or even greater than or equal to 10 mol. %. For example, in some embodiments the glass composition may include $Na_2O$ in an amount greater than or equal to about 9 mol. % and less than or equal to about 15 mol. % or even greater than or equal to about 9 mol. % and less than or equal to 13 mol. %.

As noted above, the alkali oxide in the glass composition may further include $K_2O$. The amount of $K_2O$ present in the glass composition also relates to the ion exchangeability of the glass composition. Specifically, as the amount of $K_2O$ present in the glass composition increases, the compressive stress obtainable through ion exchange decreases as a result of the exchange of potassium and sodium ions. Accordingly, it is desirable to limit the amount of $K_2O$ present in the glass composition. In some embodiments, the amount of $K_2O$ is greater than or equal to 0 mol. % and less than or equal to 3 mol. %. In some embodiments, the amount of $K_2O$ is less or equal to 2 mol. % or even less than or equal to 1.0 mol. %. In embodiments where the glass composition includes $K_2O$, the $K_2O$ may be present in a concentration greater than or equal to about 0.01 mol. % and less than or equal to about 3.0 mol. % or even greater than or equal to about 0.01 mol. % and less than or equal to about 2.0 mol. %. In some embodiments, the amount of $K_2O$ present in the glass composition is greater than or equal to about 0.01 mol. % and less than or equal to about 1.0 mol. %. Accordingly, it should be understood that $K_2O$ need not be present in the glass composition. However, when $K_2O$ is included in the glass composition, the amount of $K_2O$ is generally less than about 3 mol. % based on the molecular weight of the glass composition.

The alkaline earth oxides present in the composition improve the meltability of the glass batch materials and increase the chemical durability of the glass composition. In the glass compositions described herein, the total mol. % of alkaline earth oxides present in the glass compositions is generally less than the total mol. % of alkali oxides present in the glass compositions in order to improve the ion exchangeability of the glass composition. In the embodiments described herein, the glass compositions generally include from about 3 mol. % to about 13 mol. % of alkaline earth oxide. In some of these embodiments, the amount of alkaline earth oxide in the glass composition may be from about 4 mol. % to about 8 mol. % or even from about 4 mol. % to about 7 mol. %.

The alkaline earth oxide in the glass composition may include MgO, CaO, SrO, BaO or combinations thereof. In some embodiments, the alkaline earth oxide includes MgO, CaO or combinations thereof. For example, in the embodiments described herein the alkaline earth oxide includes MgO. MgO is present in the glass composition in an amount which is greater than or equal to about 3 mol. % and less than or equal to about 8 mol. % MgO. In some embodiments, MgO may be present in the glass composition in an amount which is greater than or equal to about 3 mol. % and less than or equal to about 7 mol. % or even greater than or equal to 4 mol. % and less than or equal to about 7 mol. % by molecular weight of the glass composition.

In some embodiments, the alkaline earth oxide may further include CaO. In these embodiments CaO is present in the glass composition in an amount from about 0 mol. % to less than or equal to 6 mol. % by molecular weight of the glass composition. For example, the amount of CaO present in the glass composition may be less than or equal to 5 mol. %, less than or equal to 4 mol. %, less than or equal to 3 mol. %, or even less than or equal to 2 mol. %. In some of these embodiments, CaO may be present in the glass composition in an amount greater than or equal to about 0.1 mol. % and less than or equal to about 1.0 mol. %. For example, CaO may be present in the glass composition in an amount greater than or equal to about 0.2 mol. % and less than or equal to about 0.7 mol. % or even in an amount greater than or equal to about 0.3 mol. % and less than or equal to about 0.6 mol. %.

In the embodiments described herein, the glass compositions are generally rich in MgO, (i.e., the concentration of MgO in the glass composition is greater than the concentration of the other alkaline earth oxides in the glass composition including, without limitation, CaO). Forming the glass composition such that the glass composition is MgO-rich improves the hydrolytic resistance of the resultant glass, particularly following ion exchange strengthening. Moreover, glass compositions which are MgO-rich generally exhibit improved ion exchange performance relative to glass compositions which are rich in other alkaline earth oxides. Specifically, glasses formed from MgO-rich glass compositions generally have a greater diffusivity than glass compositions which are rich in other alkaline earth oxides, such as CaO. The greater diffusivity enables the formation of a deeper depth of layer in the glass. MgO-rich glass compositions also enable a higher compressive stress to be achieved in the surface of the glass compared to glass compositions which are rich in other alkaline earth oxides such as CaO. In addition, it is generally understood that as the ion exchange process proceeds and alkali ions penetrate more deeply into the glass, the maximum compressive stress achieved at the surface of the glass may decrease with time. However, glasses formed from glass compositions which are MgO-rich exhibit a lower reduction in compressive stress than glasses formed from glass compositions that are CaO-rich or rich in other alkaline earth oxides (i.e., glasses which are MgO-poor). Thus, MgO-rich glass compositions enable glasses which have higher compressive stress at the surface and greater depths of layer than glasses which are rich in other alkaline earth oxides.

In order to fully realize the benefits of MgO in the glass compositions described herein, it has been determined that the ratio of the concentration of CaO to the sum of the concentration of CaO and the concentration of MgO in mol.

% (i.e., (CaO/(CaO+MgO)) should be minimized. Specifically, it has been determined that (CaO/(CaO+MgO)) should be less than or equal to 0.5. In some embodiments (CaO/(CaO+MgO)) is less than or equal to 0.3 or even less than or equal to 0.2. In some other embodiments (CaO/(CaO+MgO)) may even be less than or equal to 0.1.

Boron oxide ($B_2O_3$) is a flux which may be added to glass compositions to reduce the viscosity at a given temperature (e.g., the strain, anneal and softening temperatures) thereby improving the formability of the glass. However, it has been found that additions of boron significantly decrease the diffusivity of sodium and potassium ions in the glass composition which, in turn, adversely impacts the ion exchange performance of the resultant glass. In particular, it has been found that additions of boron significantly increase the time required to achieve a given depth of layer relative to glass compositions which are boron free. Accordingly, in some embodiments described herein, the amount of boron added to the glass composition is minimized in order to improve the ion exchange performance of the glass composition.

For example, it has been determined that the impact of boron on the ion exchange performance of a glass composition can be mitigated by controlling the ratio of the concentration of $B_2O_3$ to the difference between the total concentration of the alkali oxides (i.e., $R_2O$, where R is the alkali metals) and alumina (i.e., $B_2O_3$ (mol. %)/($R_2O$ (mol. %)-$Al_2O_3$ (mol. %)). In particular, it has been determined that when the ratio of $B_2O_3/(R_2O—Al_2O_3)$ is greater than or equal to about 0 and less than about 0.3 or even less than about 0.2, the diffusivities of alkali oxides in the glass compositions are not diminished and, as such, the ion exchange performance of the glass composition is maintained. Accordingly, in some embodiments, the ratio of $B_2O_3/(R_2O—Al_2O_3)$ is greater than 0 and less than or equal to 0.3. In some of these embodiments, the ratio of $B_2O_3/(R_2O—Al_2O_3)$ is greater than 0 and less than or equal to 0.2. In some embodiments, the ratio of $B_2O_3/(R_2O—Al_2O_3)$ is greater than 0 and less than or equal to 0.15 or even less than or equal to 0.1. In some other embodiments, the ratio of $B_2O_3/(R_2O—Al_2O_3)$ may be greater than 0 and less than or equal to 0.05. Maintaining the ratio $B_2O_3/(R_2O—Al_2O_3)$ to be less than or equal to 0.3 or even less than or equal to 0.2 permits the inclusion of $B_2O_3$ to lower the strain point, anneal point and softening point of the glass composition without the $B_2O_3$ adversely impacting the ion exchange performance of the glass.

In the embodiments described herein, the concentration of $B_2O_3$ in the glass composition is generally less than or equal to about 4 mol. %, less than or equal to about 3 mol. %, less than or equal to about 2 mol. %, or even less than or equal to 1 mol. %. For example, in embodiments where $B_2O_3$ is present in the glass composition, the concentration of $B_2O_3$ may be greater than about 0.01 mol. % and less than or equal to 4 mol. %. In some of these embodiments, the concentration of $B_2O_3$ may be greater than about 0.01 mol. % and less than or equal to 3 mol. % In some embodiments, the $B_2O_3$ may be present in an amount greater than or equal to about 0.01 mol. % and less than or equal to 2 mol. %, or even less than or equal to 1.5 mol. %. Alternatively, the $B_2O_3$ may be present in an amount greater than or equal to about 1 mol. % and less than or equal to 4 mol. %, greater than or equal to about 1 mol. % and less than or equal to 3 mol. % or even greater than or equal to about 1 mol. % and less than or equal to 2 mol. %. In some of these embodiments, the concentration of $B_2O_3$ may be greater than or equal to about 0.1 mol. % and less than or equal to 1.0 mol. %.

While in some embodiments the concentration of $B_2O_3$ in the glass composition is minimized to improve the forming properties of the glass without detracting from the ion exchange performance of the glass, in some other embodiments the glass compositions are free from boron and compounds of boron such as $B_2O_3$. Specifically, it has been determined that forming the glass composition without boron or compounds of boron improves the ion exchangeability of the glass compositions by reducing the process time and/or temperature required to achieve a specific value of compressive stress and/or depth of layer.

In some embodiments of the glass compositions described herein, the glass compositions are free from phosphorous and compounds containing phosphorous including, without limitation, $P_2O_5$. Specifically, it has been determined that formulating the glass composition without phosphorous or compounds of phosphorous increases the chemical durability of the glass composition.

In addition to the $SiO_2$, $Al_2O_3$, alkali oxides and alkaline earth oxides, the glass compositions described herein may optionally further comprise one or more fining agents such as, for example, $SnO_2$, $As_2O_3$, and/or Cl⁻ (from NaCl or the like). When a fining agent is present in the glass composition, the fining agent may be present in an amount less than or equal to about 1 mol. % or even less than or equal to about 0.4 mol. %. For example, in some embodiments the glass composition may include $SnO_2$ as a fining agent. In these embodiments $SnO_2$ may be present in the glass composition in an amount greater than about 0 mol. % and less than or equal to about 1 mol. % or even an amount greater than or equal to about 0.01 mol. % and less than or equal to about 0.30 mol. %.

Moreover, the glass compositions described herein may comprise one or more additional metal oxides to further improve the chemical durability of the glass composition. For example, the glass composition may further include ZnO, $TiO_2$, or $ZrO_2$, each of which further improves the resistance of the glass composition to chemical attack. In these embodiments, the additional metal oxide may be present in an amount which is greater than or equal to about 0 mol. % and less than or equal to about 2 mol. %. For example, when the additional metal oxide is ZnO, the ZnO may be present in an amount greater than or equal to 1 mol. % and less than or equal to about 2 mol. %. When the additional metal oxide is $ZrO_2$ or $TiO_2$, the $ZrO_2$ or $TiO_2$ may be present in an amount less than or equal to about 1 mol. %.

Based on the foregoing, it should be understood that, in a first exemplary embodiment, a glass composition may include: $SiO_2$ in a concentration greater than about 70 mol. % and Y mol. % alkali oxide. The alkali oxide may include $Na_2O$ in an amount greater than about 8 mol. %. The glass composition may be free of boron and compounds of boron. The concentration of $SiO_2$ in this glass composition may be greater than or equal to about 72 mol. %, greater than 73 mol. % or even greater than 74 mol. %. The glass composition of this first exemplary embodiment may be free from phosphorous and compounds of phosphorous. The glass composition may also include X mol. % $Al_2O_3$. When $Al_2O_3$ is included, the ratio of Y:X may be greater than 1. The concentration of $Al_2O_3$ may be greater than or equal to about 2 mol. % and less than or equal to about 10 mol. %.

The glass composition of this first exemplary embodiment may also include alkaline earth oxide in an amount from about 3 mol. % to about 13 mol. %. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

In a second exemplary embodiment, a glass composition may include: greater than about 68 mol. % $SiO_2$; X mol. % $Al_2O_3$; Y mol. % alkali oxide; and $B_2O_3$. The alkali oxide may include $Na_2O$ in an amount greater than about 8 mol %. A ratio ($B_2O_3$ (mol. %)/(Y mol. %–X mol. %) may be greater than 0 and less than 0.3. The concentration of $SiO_2$ in this glass composition may be greater than or equal to about 72 mol. %, greater than 73 mol. % or even greater than 74 mol. %. The concentration of $Al_2O_3$ may be greater than or equal to about 2 mol. % and less than or equal to about 10 mol. %. In this second exemplary embodiment, the ratio of Y:X may be greater than 1. When the ratio of Y:X is greater than 1, an upper bound of the ratio of Y:X may be less than or equal to 2. The glass composition of this first exemplary embodiment may be free from phosphorous and compounds of phosphorous.

The glass composition of this second exemplary embodiment may also include alkaline earth oxide. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

The concentration of $B_2O_3$ in this second exemplary embodiment may be greater than or equal to about 0.01 mol. % and less than or equal to about 4 mol. %.

In a third exemplary embodiment, a glass article may have a type HgB1 hydrolytic resistance according to ISO 719. The glass article may include greater than about 8 mol. % $Na_2O$ and less than about 4 mol. % $B_2O_3$. The glass article may further comprise X mol. % $Al_2O_3$ and Y mol. % alkali oxide. The ratio ($B_2O_3$ (mol. %)/(Y mol. %–X mol. %) may be greater than 0 and less than 0.3. The glass article of this third exemplary embodiment may further include a compressive stress layer having a surface compressive stress greater than or equal to about 250 MPa. The glass article may also have at least a class S3 acid resistance according to DIN 12116; at least a class A2 base resistance according to ISO 695; and a type HgA1 hydrolytic resistance according to ISO 720.

In a fourth exemplary embodiment, a glass pharmaceutical package may include $SiO_2$ in an amount greater than about 70 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. The glass pharmaceutical package may also have a type HGB1 hydrolytic resistance according to ISO 719. The concentration of $SiO_2$ in the glass pharmaceutical package of this fourth exemplary embodiment may be greater than or equal to 72 mol. % and less than or equal to about 78 mol. % or even greater than 74 mol. % and less than or equal to about 78 mol. %. The concentration of $Al_2O_3$ in the glass pharmaceutical may be greater than or equal to about 4 mol. % and less than or equal to about 8 mol. %. A ratio of Y:X may be greater than 1 and less than 2.

The glass pharmaceutical package of this fourth exemplary embodiment may also include alkaline earth oxide in an amount from about 4 mol. % to about 8 mol. %. The alkaline earth oxide may include MgO and CaO. The CaO may be present in an amount greater than or equal to about 0.2 mol. % and less than or equal to about 0.7 mol. %. A ratio (CaO (mol. %)/(CaO (mol. %)+MgO (mol. %))) may be less than or equal to 0.5. The glass pharmaceutical package of this fourth exemplary embodiment may have a type HGA1 hydrolytic resistance according to ISO 720.

In a fifth exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. A ratio of Y:X may be greater than 1. The glass composition may be free of boron and compounds of boron.

In a sixth exemplary embodiment, a glass composition may include from about 68 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. The glass composition of this sixth exemplary embodiment may also include $B_2O_3$. A ratio ($B_2O_3$ (mol. %)/(Y mol. %–X mol. %) may be greater than 0 and less than 0.3. A ratio of Y:X may be greater than 1.

In a seventh exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The amount of $Al_2O_3$ in the glass composition may be greater than or equal to about 2 mol. % and less than or equal to about 10 mol. %. The alkaline earth oxide may include CaO in an amount greater than or equal to about 0.1 mol. % and less than or equal to about 1.0 mol. %. The alkali oxide may include from about 0.01 mol. % to about 1.0 mol. % $K_2O$. A ratio of Y:X may be greater than 1. The glass composition may be free of boron and compounds of boron. The glass composition may be amenable to strengthening by ion exchange.

In a seventh exemplary embodiment, a glass composition may include $SiO_2$ in an amount greater than about 70 mol. % and less than or equal to about 80 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. A ratio of Y:X may be greater than 1.

In an eighth exemplary embodiment, a glass composition may include from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %.; and Y mol. % alkali oxide, wherein the alkali oxide comprises $Na_2O$ in an amount greater than or equal to about 9 mol. % and less than or equal to about 15 mol. %. A ratio of a concentration of $B_2O_3$ (mol. %) in the glass pharmaceutical package to (Y mol. %–X mol. %) is less than 0.3. A ratio of Y:X may be greater than 1.

In a ninth exemplary embodiment, a pharmaceutical package for containing a pharmaceutical composition may include from about 70 mol. % to about 78 mol. % $SiO_2$; from about 3 mol. % to about 13 mol. % alkaline earth oxide; X mol. % $Al_2O_3$, wherein X is greater than or equal to 2 mol. % and less than or equal to about 10 mol. %; and Y mol. % alkali oxide, wherein the alkali oxide comprises $Na_2O$ in an amount greater than about 8 mol. %. The alkaline earth oxide may include CaO in an amount less than or equal to about 6.0 mol. %. A ratio of Y:X may be greater than about 1. The package may be free of boron and compounds of boron and may include a compressive stress layer with a compressive stress greater than or equal to about 250 MPa and a depth of layer greater than or equal to about 10 μm.

In a tenth exemplary embodiment, a glass article may be formed from a glass composition comprising from about 70 mol. % to about 78 mol. % SiO$_2$; alkaline earth oxide, wherein the alkaline earth oxide comprises MgO and CaO and a ratio (CaO (mol. %)/(CaO (mol. %)+MgO (mol. %))) is less than or equal to 0.5; X mol. % Al$_2$O$_3$, wherein X is from about 2 mol. % to about 10 mol. %; and Y mol. % alkali oxide, wherein the alkali oxide comprises Na$_2$O in an amount greater than about 8 mol. % and a ratio of Y:X is greater than 1. The glass article may be ion exchange strengthened with a compressive stress greater than or equal to 250 MPa and a depth of layer greater than or equal to 10 μm. The glass article may have a type HgA1 hydrolytic resistance according to ISO 720.

As noted above, the presence of alkali oxides in the glass composition facilitates chemically strengthening the glass by ion exchange. Specifically, alkali ions, such as potassium ions, sodium ions and the like, are sufficiently mobile in the glass to facilitate ion exchange. In some embodiments, the glass composition is ion exchangeable to form a compressive stress layer having a depth of layer greater than or equal to 10 μm. In some embodiments, the depth of layer may be greater than or equal to about 25 μm or even greater than or equal to about 50 μm. In some other embodiments, the depth of the layer may be greater than or equal to 75 μm or even greater than or equal to 100 μm. In still other embodiments, the depth of layer may be greater than or equal to 10 μm and less than or equal to about 100 μm. The associated surface compressive stress may be greater than or equal to about 250 MPa, greater than or equal to 300 MPa or even greater than or equal to about 350 MPa after the glass composition is treated in a salt bath of 100% molten KNO$_3$ at a temperature of 350° C. to 500° C. for a time period of less than about 30 hours or even about less than 20 hours.

The glass articles formed from the glass compositions described herein may have a hydrolytic resistance of HGB2 or even HGB1 under ISO 719 and/or a hydrolytic resistance of HGA2 or even HGA1 under ISO 720 (as described further herein) in addition to having improved mechanical characteristics due to ion exchange strengthening. In some embodiments described herein the glass articles may have compressive stresses which extend from the surface into the glass article to a depth of layer greater than or equal to 10 μm, greater than or equal to 15 μm, greater than or equal to 20 μm, greater than or equal to 25 μm, greater than or equal to 30 μm or even greater than or equal to 35 μm. In some embodiments, the depth of layer may be greater than or equal to 40 μm or even greater than or equal to 50 μm. The surface compressive stress of the glass article may be greater than or equal to 150 MPa, greater than or equal to 200 MPa, greater than or equal to 250 MPa, greater than or equal to 350 MPa, or even greater than or equal to 400 MPa.

In one embodiment, the glass pharmaceutical container has a compressive stress greater than or equal to 150 MPa and a depth of layer greater than or equal to 10 μm, 15 μm, 20 μm, 25 μm, 30 μm, 35 μm, 40 μm, 45 μm or 50 μm. In a particular embodiment, the glass pharmaceutical container has a compressive stress greater than or equal to 150 MPa and a depth of layer greater than or equal to 10 μm. In a particular embodiment, the glass pharmaceutical container has a compressive stress greater than or equal to 150 MPa and a depth of layer greater than or equal to 25 μm. In a particular embodiment, the glass pharmaceutical container has a compressive stress greater than or equal to 150 MPa and a depth of layer greater than or equal to 30 μm.

In one embodiment, the glass pharmaceutical container has a compressive stress greater than or equal to 300 MPa and a depth of layer greater than or equal to 10 μm, 15 μm, 20 μm, 25 μm, 30 μm, 35 μm, 40 μm, 45 μm or 50 μm. In a particular embodiment, the glass pharmaceutical container has a compressive stress greater than or equal to 300 MPa and a depth of layer greater than or equal to 25 μm. In yet another embodiment, the glass pharmaceutical container has a compressive stress greater than or equal to 300 MPa and a depth of layer greater than or equal to 30 μm. In yet another embodiment, the glass pharmaceutical container has a compressive stress greater than or equal to 300 MPa and a depth of layer greater than or equal to 35 μm.

The glass compositions described herein facilitate achieving the aforementioned depths of layer and surface compressive stresses more rapidly and/or at lower temperatures than conventional glass compositions due to the enhanced alkali ion diffusivity of the glass compositions as described hereinabove. For example, the depths of layer (i.e., greater than or equal to 25 μm) and the compressive stresses (i.e., greater than or equal to 250 MPa) may be achieved by ion exchanging the glass article in a molten salt bath of 100% KNO$_3$ (or a mixed salt bath of KNO$_3$ and NaNO$_3$) for a time period of less than or equal to 5 hours or even less than or equal to 4.5 hours. In some embodiments, these depths of layer and compressive stresses may be achieved by ion exchanging the glass article in a molten salt bath of 100% KNO$_3$ (or a mixed salt bath of KNO$_3$ and NaNO$_3$) for a time period of less than or equal to 4 hours or even less than or equal to 3.5 hours. Moreover, these depths of layers and compressive stresses may be achieved by ion exchanging the glass articles in a molten salt bath of 100% KNO3 (or a mixed salt bath of KNO$_3$ and NaNO$_3$) at a temperature less than or equal to 500° C. or even less than or equal to 450° C. In some embodiments, these depths of layers and compressive stresses may be achieved by ion exchanging the glass articles in a molten salt bath of 100% KNO3 (or a mixed salt bath of KNO$_3$ and NaNO$_3$) at a temperature less than or equal to 400° C. or even less than or equal to 350° C.

These improved ion exchange characteristics can be achieved when the glass composition has a threshold diffusivity of greater than about 16 μm$^2$/hr or even greater than or equal to 20 μm$^2$/hr at 450° C. In some embodiments, the threshold diffusivity may be greater than or equal to about 25 μm$^2$/hr or even 30 μm$^2$/hr at 450° C. In some other embodiments, the threshold diffusivity may be greater than or equal to about 35 μm$^2$/hr or even 40 μm$^2$/hr at 450° C. In still other embodiments, the threshold diffusivity may be greater than or equal to about 45 μm$^2$/hr or even 50 μm$^2$/hr at 450° C.

The glass compositions described herein may generally have a strain point greater than or equal to about 525° C. and less than or equal to about 650° C. The glasses may also have an anneal point greater than or equal to about 560° C. and less than or equal to about 725° C. and a softening point greater than or equal to about 750° C. and less than or equal to about 960° C.

In the embodiments described herein the glass compositions have a CTE of less than about 70×10$^{-7}$K$^{-1}$ or even less than about 60×10$^{-7}$K$^{-1}$. These lower CTE values improve the survivability of the glass to thermal cycling or thermal stress conditions relative to glass compositions with higher CTEs.

Further, as noted hereinabove, the glass compositions are chemically durable and resistant to degradation as determined by the DIN 12116 standard, the ISO 695 standard, and the ISO 720 standard.

Specifically, the DIN 12116 standard is a measure of the resistance of the glass to decomposition when placed in an acidic solution. In brief, the DIN 12116 standard utilizes a polished glass sample of a known surface area which is weighed and then positioned in contact with a proportional amount of boiling 6M hydrochloric acid for 6 hours. The sample is then removed from the solution, dried and weighed again. The glass mass lost during exposure to the acidic solution is a measure of the acid durability of the sample with smaller numbers indicative of greater durability. The results of the test are reported in units of half-mass per surface area, specifically mg/dm$^2$. The DIN 12116 standard is broken into individual classes. Class S1 indicates weight losses of up to 0.7 mg/dm$^2$; Class S2 indicates weight losses from 0.7 mg/dm$^2$ up to 1.5 mg/dm$^2$; Class S3 indicates weight losses from 1.5 mg/dm$^2$ up to 15 mg/dm$^2$; and Class S4 indicates weight losses of more than 15 mg/dm$^2$.

The ISO 695 standard is a measure of the resistance of the glass to decomposition when placed in a basic solution. In brief, the ISO 695 standard utilizes a polished glass sample which is weighed and then placed in a solution of boiling 1M NaOH+0.5M Na$_2$CO$_3$ for 3 hours. The sample is then removed from the solution, dried and weighed again. The glass mass lost during exposure to the basic solution is a measure of the base durability of the sample with smaller numbers indicative of greater durability. As with the DIN 12116 standard, the results of the ISO 695 standard are reported in units of mass per surface area, specifically mg/dm$^2$. The ISO 695 standard is broken into individual classes. Class A1 indicates weight losses of up to 75 mg/dm$^2$; Class A2 indicates weight losses from 75 mg/dm$^2$ up to 175 mg/dm$^2$; and Class A3 indicates weight losses of more than 175 mg/dm$^2$.

The ISO 720 standard is a measure of the resistance of the glass to degradation in purified, CO$_2$-free water. In brief, the ISO 720 standard protocol utilizes crushed glass grains which are placed in contact with the purified, CO$_2$-free water under autoclave conditions (121° C., 2 atm) for 30 minutes. The solution is then titrated colorimetrically with dilute HCl to neutral pH. The amount of HCl required to titrate to a neutral solution is then converted to an equivalent of Na$_2$O extracted from the glass and reported in μg Na$_2$O per weight of glass with smaller values indicative of greater durability. The ISO 720 standard is broken into individual types. Type HGA1 is indicative of up to 62 μg extracted equivalent of Na$_2$O per gram of glass tested; Type HGA2 is indicative of more than 62 μg and up to 527 μg extracted equivalent of Na$_2$O per gram of glass tested; and Type HGA3 is indicative of more than 527 μg and up to 930 μg extracted equivalent of Na$_2$O per gram of glass tested.

The ISO 719 standard is a measure of the resistance of the glass to degradation in purified, CO$_2$-free water. In brief, the ISO 719 standard protocol utilizes crushed glass grains which are placed in contact with the purified, CO$_2$-free water at a temperature of 98° C. at 1 atmosphere for 30 minutes. The solution is then titrated colorimetrically with dilute HCl to neutral pH. The amount of HCl required to titrate to a neutral solution is then converted to an equivalent of Na$_2$O extracted from the glass and reported in μg Na$_2$O per weight of glass with smaller values indicative of greater durability. The ISO 719 standard is broken into individual types. The ISO 719 standard is broken into individual types. Type HGB1 is indicative of up to 31 μg extracted equivalent of Na$_2$O; Type HGB2 is indicative of more than 31 μg and up to 62 μg extracted equivalent of Na$_2$O; Type HGB3 is indicative of more than 62 μg and up to 264 μg extracted equivalent of Na$_2$O; Type HGB4 is indicative of more than 264 μg and up to 620 μg extracted equivalent of Na$_2$O; and Type HGB5 is indicative of more than 620 μg and up to 1085 μg extracted equivalent of Na$_2$O. The glass compositions described herein have an ISO 719 hydrolytic resistance of type HGB2 or better with some embodiments having a type HGB1 hydrolytic resistance.

The glass compositions described herein have an acid resistance of at least class S3 according to DIN 12116 both before and after ion exchange strengthening with some embodiments having an acid resistance of at least class S2 or even class S1 following ion exchange strengthening. In some other embodiments, the glass compositions may have an acid resistance of at least class S2 both before and after ion exchange strengthening with some embodiments having an acid resistance of class S1 following ion exchange strengthening. Further, the glass compositions described herein have a base resistance according to ISO 695 of at least class A2 before and after ion exchange strengthening with some embodiments having a class A1 base resistance at least after ion exchange strengthening. The glass compositions described herein also have an ISO 720 type HGA2 hydrolytic resistance both before and after ion exchange strengthening with some embodiments having a type HGA1 hydrolytic resistance after ion exchange strengthening and some other embodiments having a type HGA1 hydrolytic resistance both before and after ion exchange strengthening. The glass compositions described herein have an ISO 719 hydrolytic resistance of type HGB2 or better with some embodiments having a type HGB1 hydrolytic resistance. It should be understood that, when referring to the above referenced classifications according to DIN 12116, ISO 695, ISO 720 and ISO 719, a glass composition or glass article which has "at least" a specified classification means that the performance of the glass composition is as good as or better than the specified classification. For example, a glass article which has a DIN 12116 acid resistance of "at least class S2" may have a DIN 12116 classification of either S1 or S2.

The glass compositions described herein are formed by mixing a batch of glass raw materials (e.g., powders of SiO$_2$, Al$_2$O$_3$, alkali oxides, alkaline earth oxides and the like) such that the batch of glass raw materials has the desired composition. Thereafter, the batch of glass raw materials is heated to form a molten glass composition which is subsequently cooled and solidified to form the glass composition. During solidification (i.e., when the glass composition is plastically deformable) the glass composition may be shaped using standard forming techniques to shape the glass composition into a desired final form. Alternatively, the glass article may be shaped into a stock form, such as a sheet, tube or the like, and subsequently reheated and formed into the desired final form.

In order to assess the long-term resistance of the glass container to delamination, an accelerated delamination test was utilized. The test is performed on glass containers after the containers have been ion-exchange strengthened. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers.

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles due based on the aspect ratio of the particle (i.e., the ratio of the width of the particle to the thickness of the particle). Delamination produces particulate flakes or lamellae which are irregularly shaped and are typically >50 μm in diameter but often >200 μm. The thickness of the flakes is usually greater than about 100 nm and may be as large as about 1 μm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

In the embodiments described herein, glass containers which average less than 3 glass particles with a minimum width of 50 μm and an aspect ratio of greater than 50 per trial following accelerated delamination testing are considered to have a delamination factor of 3. In the embodiments described herein, glass containers which average less than 2 glass particles with a minimum width of 50 μm and an aspect ratio of greater than 50 per trial following accelerated delamination testing are considered to have a delamination factor of 2. In the embodiments described herein, glass containers which average less than 1 glass particle with a minimum width of 50 μm and an aspect ratio of greater than 50 per trial following accelerated delamination testing are considered to have a delamination factor of 1. In the embodiments described herein, glass containers which have 0 glass particles with a minimum width of 50 μm and an aspect ratio of greater than 50 per trial following accelerated delamination testing are considered to have a delamination factor of 0. Accordingly, it should be understood that the lower the delamination factor, the better the resistance of the glass container to delamination. In the embodiments described herein, the glass containers have a delamination factor of 3 or lower (i.e., a delamination factor of 3, 2, 1 or 0).

Pharmaceutical Containers

In view of the chemical durability of the glass composition of the present invention, the glass compositions described herein are particularly well suited for use in designing pharmaceutical containers for storing, maintaining and/or delivering pharmaceutical compositions, such as liquids, solutions, powders, e.g., lyophilized powders, solids and the like. As used herein, the term "pharmaceutical container" refers to a composition designed to store, maintain and/or deliver a pharmaceutical composition. The pharmaceutical containers, as described herein, are formed, at least in part, of the delamination resistant glass compositions described above. Pharmaceutical containers of the present invention include, but are not limited to, Vacutainers™, cartridges, syringes, ampoules, bottles, flasks, phials, tubes, beakers, vials, injection pens or the like. In a particular embodiment, the pharmaceutical container is a vial. In a particular embodiment, the pharmaceutical container is an ampoule. In a particular embodiment, the pharmaceutical container is an injection pen. In a particular embodiment, the pharmaceutical container is a tube. In a particular embodiment, the pharmaceutical container is a bottle. In a particular embodiment, the pharmaceutical container is a syringe.

Moreover, the ability to chemically strengthen the glass compositions through ion exchange can be utilized to improve the mechanical durability of pharmaceutical containers formed from the glass composition. Accordingly, it should be understood that, in at least one embodiment, the glass compositions are incorporated in a pharmaceutical container in order to improve the chemical durability and/or the mechanical durability of the pharmaceutical container.

Pharmaceutical Compositions

In various embodiments, the pharmaceutical container further includes a pharmaceutical composition comprising an active pharmaceutical ingredient (API). As used herein, the term "pharmaceutical composition" refers to a composition comprising an active pharmaceutical ingredient to be delivered to a subject, for example, for therapeutic, prophylactic, diagnostic, preventative or prognostic effect. In certain embodiments, the pharmaceutical composition comprises the active pharmaceutical ingredient and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active pharmaceutical agent.

As used herein, the term "active pharmaceutical ingredient" or "API" refers a substance in a pharmaceutical composition that provides a desired effect, for example, a therapeutic, prophylactic, diagnostic, preventative or prognostic effect. In various embodiments, the active pharmaceutical ingredient can be any of a variety of substances known in the art, for example, a small molecule, a polypeptide mimetic, a biologic, an antisense RNA, a small interfering RNA (siRNA), etc.

For example, in a particular embodiment, the active pharmaceutical ingredient may be a small molecule. As used herein, the term "small molecule" includes any chemical or other moiety, other than polypeptides and nucleic acids, that can act to affect biological processes. Small molecules can include any number of therapeutic agents presently known and used, or that can be synthesized from a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include, without limitation, organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

In another embodiment, the active pharmaceutical ingredient may be a polypeptide mimetic ("peptidomimetic"). As used herein, the term "polypeptide mimetic" is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

In other embodiments, the active pharmaceutical ingredient may be a biologic. As used herein, the term "biologic" includes products created by biologic processes instead of by chemical synthesis. Non-limiting examples of a "biologic" include proteins, antibodies, antibody like molecules, vaccines, blood, blood components, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., *Cancer Res.* 2004 Apr. 15, 64(8):2853-2857)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., *Science*, Aug. 16, 1991, 253(5021):792-795. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., *Biochem. Biophys. Res. Commun.* Jul. 18, 2003, 307(1): 198-205. Additional discussion of related principles, methods, etc., that may be applicable in the context of this invention are provided in, e.g., Fassina, *Immunomethods.* October 1994, 5(2):121-9.

In various embodiments, the active pharmaceutical ingredient may have any of a variety of activities selected from the group consisting of anti-rheumatics, anti-neoplastic, vaccines, anti-diabetics, haematologicals, muscle relaxant, immunostimulants, anti-coagulants, bone calcium regulators, sera and gammaglobulins, anti-fibrinolytics, MS therapies, anti-anaemics, cytostatics, interferons, anti-metabolites, radiopharmaceuticals, anti-psychotics, anti-bacterials, immunosuppressants, cytotoxic antibiotics, cerebral & peripheral vasotherapeutics, nootropics, CNS drugs, dermatologicals, angiotensin antagonists, anti-spasmodics, anti-cholinergics, interferons, anti-psoriasis agents, anti-hyperlipidaemics, cardiac therapies, alkylating agents, bronchodilators, anti-coagulants, anti-inflammatories, growth hormones, and diagnostic imaging agents.

In various embodiments, the pharmaceutical composition may be selected from the group consisting of PERJETA (pertuzumab), ACTEMRA (tocilizumab), KADCYLA (trastuzumab emtansine), MetMAb (onartuzumab), obinutuzumab, ocrelizumab and lebrikizumab.

In a particular embodiment, the pharmaceutical composition comprises pertuzumab. In a particular embodiment, the active pharmaceutical ingredient comprises a recombinant humanized monoclonal antibody that targets the extracellular dimerization domain (Subdomain II) of the human epidermal growth factor receptor 2 protein (HER2). Pertuzumab (PERJETA™) is a recombinant humanized monoclonal antibody that targets the extracellular dimerization domain (Subdomain II) of the human epidermal growth factor receptor 2 protein (HER2). Pertuzumab is produced by recombinant DNA technology in a mammalian cell (Chinese Hamster Ovary) culture containing the antibiotic, gentamicin. Gentamicin is not detectable in the final product. Pertuzumab has an approximate molecular weight of 148 kDa. PERJETA is a sterile, clear to slightly opalescent, colorless to pale brown liquid for intravenous infusion. Each single use vial contains 420 mg of pertuzumab at a concentration of 30 mg/mL in in 20 mM L-histidine acetate (pH 6.0), 120 mM sucrose and 0.02% polysorbate 20.

Pertuzumab targets the extracellular dimerization domain (Subdomain II) of the human epidermal growth factor receptor 2 protein (HER2) and, thereby, blocks ligand-dependent heterodimerization of HER2 with other HER family members, including EGFR, HER3 and HER4. As a result, pertuzumab inhibits ligand-initiated intracellular signaling through two major signal pathways, mitogen-activated protein (MAP) kinase and phosphoinositide 3-kinase (PI3K). Inhibition of these signaling pathways can result in cell growth arrest and apoptosis, respectively. In addition, pertuzumab mediates antibody-dependent cell-mediated cytotoxicity (ADCC).

In a particular embodiment, the pharmaceutical composition comprises Tocilizumab. In a particular embodiment, the active pharmaceutical ingredient comprises a humanized anti-human interleukin-6 (IL-6) receptor antibody. Tocilizumab (ACTEMRA®), a recombinant humanized anti-human interleukin 6 (IL-6) receptor monoclonal antibody of the immunoglobulin IgG1κ (gamma 1, kappa) subclass with a typical $H_2L_2$ polypeptide structure. Each light chain and heavy chain consists of 214 and 448 amino acids, respectively. The four polypeptide chains are linked intra- and inter-molecularly by disulfide bonds. Tocilizumab has a molecular weight of approximately 148 kDa.

ACTEMRA is supplied as a sterile, preservative-free solution for intravenous (IV) infusion at a concentration of 20 mg/mL. ACTEMRA is a colorless to pale yellow liquid, with a pH of about 6.5. Single-use vials are available containing 80 mg/4 mL, 200 mg/10 mL, or 400 mg/20 mL of ACTEMRA. Injectable solutions of ACTEMRA are formulated in an aqueous solution containing disodium phosphate dodecahydrate and sodium dihydrogen phosphate dehydrate (as a 15 mmol/L phosphate buffer), polysorbate 80 (0.5 mg/ml), and sucrose (50 mg/mL).

Tocilizumab binds specifically to both soluble and membrane-bound IL-6 receptors (sIL-6R and mIL-6R), and has been shown to inhibit IL-6-mediated signaling through these receptors. IL-6 is a pleiotropic pro-inflammatory cytokine produced by a variety of cell types including T- and B-cells, lymphocytes, monocytes and fibroblasts. IL-6 has been shown to be involved in diverse physiological processes such as T-cell activation, induction of immunoglobulin secretion, initiation of hepatic acute phase protein synthesis, and stimulation of hematopoietic precursor cell proliferation and differentiation. IL-6 is also produced by synovial and endothelial cells leading to local production of IL-6 in joints affected by inflammatory processes such as rheumatoid arthritis.

In particular embodiments, the pharmaceutical composition comprises a HER2-targeted antibody and microtubule inhibitor conjugate. In a particular embodiment, the active pharmaceutical ingredient comprises ado-trastuzumab emtansine. Ado-trastuzumab emtansine (KADCYLA) is a HER2-targeted antibody-drug conjugate (ADC) which contains the humanized anti-HER2 IgG1, trastuzumab, covalently linked to the microtubule inhibitory drug DM1 (a maytansine derivative) via the stable thioether linker MCC (4-[N-maleimidomethyl]cyclohexane-1-carboxylate).

Emtansine refers to the MCC-DM1 complex. The antibody trastuzumab, is a well characterized recombinant monoclonal antibody product produced by mammalian (Chinese hamster ovary) cells, and the small molecule components (DM1 and MCC) are produced by chemical synthesis. Ado-trastuzumab emtansine contains an average of 3.5 DM1 molecules per antibody. Ado-trastuzumab emtansine has the following chemical structure:

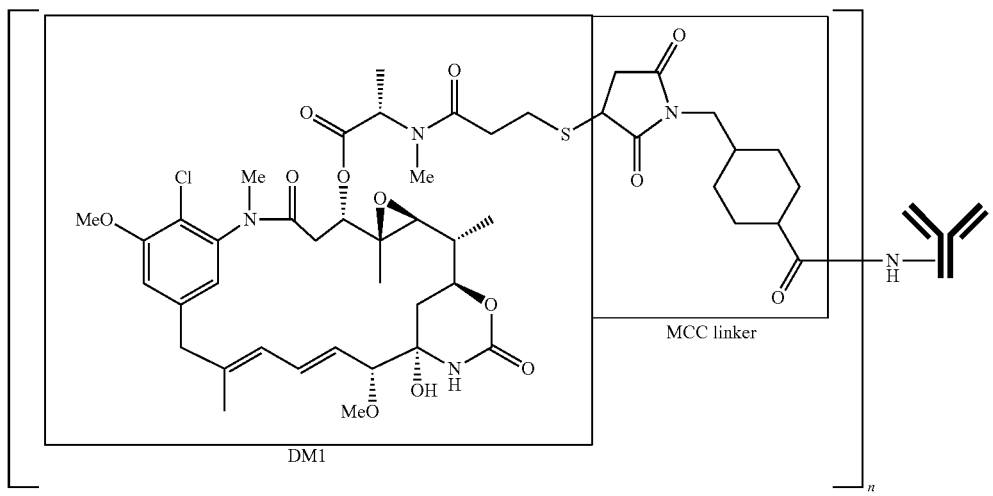

Where n ~ 3.5
DM1/Mab

Ado-trastuzumab emtansine is a HER2-targeted antibody-drug conjugate. The antibody is the humanized anti-HER2 IgG1, trastuzumab. The small molecule cytotoxin, DM1, is a microtubule inhibitor. Upon binding to sub-domain IV of the HER2 receptor, ado-trastuzumab emtansine undergoes receptor-mediated internalization and subsequent lysosomal degradation, resulting in intracellular release of DM1-containing cytotoxic catabolites. Binding of DM1 to tubulin disrupts microtubule networks in the cell, which results in cell cycle arrest and apoptotic cell death. In addition, in vitro studies have shown that similar to trastuzumab, ado-trastuzumab emtansine inhibits HER2 receptor signaling, mediates antibody-dependent cell-mediated cytotoxicity and inhibits shedding of the HER2 extracellular domain in human breast cancer cells that overexpress HER2.

KADCYLA (ado-trastuzumab emtansine) is a sterile, white to off-white preservative free lyophilized powder in single-use vials. Each vial contains 100 mg or 160 mg ado-trastuzumab emtansine. Following reconstitution, each single-use vial contains ado-trastuzumab emtansine (20 mg/mL), polysorbate 20 [0.02% (w/v)], sodium succinate (10 mM), and sucrose [6% (w/v)] with a pH of 5.0 and density of 1.026 g/mL. The resulting solution containing 20 mg/mL ado trastuzumab emtansine is administered by intravenous infusion following dilution.

In a particular embodiment, the pharmaceutical composition comprises onartuzumab. Onartuzumab (MetMAb) is a monovalent (one-armed), monoclonal antibody designed to bind to Met and inhibit HGF/SF binding. Traditional bivalent antibodies to Met potentially activate, rather than inhibit, Met signaling by inducing Met dimerization. In contrast, the monovalent design of Onartuzumab (MetMAb) inhibits HGF/SF binding without inducing Met dimerization. Onartuzumab (MetMAb), having an apparent molecular weight of approximately 99.1 kD, has demonstrated antitumor activity in preclinical analyses Onartuzumab (MetMAb) is specifically designed as a monovalent antibody to avoid agonistic activity that may occur when a bivalent antibody binds two Met molecules. Onartuzumab (MetMAb) binds to the Sema domain of Met, an extracellular region essential for binding its ligand, HGF/SF. Onartuzumab (MetMAb) inhibits HGF/SF from binding to Met, thereby blocking ligand-induced Met dimerization and activation of the intracellular kinase domain. Blockade of Met activation inhibits its downstream pathways, preventing cancer cell growth, survival, and metastasis.

In a particular embodiment, the pharmaceutical composition comprises obinutuzumab. Obinutuzumab, having a molecular weight of approximately 146.1 kDa, is a glyco-engineered, fully humanized IgG1 monoclonal antibody with potential antineoplastic activity. Obinutuzumab is a third generation type II anti-CD20 antibody, selectivity binds to the extracellular domain of the human CD20 antigen on malignant human B cells. The Fc region carbohydrates of the antibody, enriched in bisected non-fucosylated glycosylation variants, contribute to its higher binding affinity for human Fcgamma RIII receptors compared to non-glycoengineered antibodies, resulting in enhanced antibody-dependent cellular cytotoxicity (ADCC) and caspase-independent apoptosis. In addition, modification of elbow hinge sequences within the antibody variable framework regions may account for the strong apoptosis-inducing activity of R7159 upon binding to CD20 on target cells. Obinutuzumab is an advanced drug in development for the treatment of hematological malignancies (cancers which affect the blood, bone marrow and lymph nodes). A first stage of phase III study has demonstrated that Obinutuzumab significantly improved progression-free survival in people with chronic lymphocytic leukemia (CLL).

In a particular embodiment, the pharmaceutical composition comprises ocrelizumab. Ocrelizumab is a humanized monoclonal antibody designed to selectively target CD20-positive B-cells, which are involved in multiple sclerosis (MS). Ocrelizumab operates by interacting with the body's immune system to eliminate CD20-positive B-cells.

In a particular embodiment, the pharmaceutical composition comprises lebrikizumab, a humanized monoclonal antibody against interleukin-13 (IL-13), over-expression of which can result in inflammation of airways, a feature of asthma. In a recent Phase II clinical trial, lebrikizumab was shown to significantly decrease the symptoms of asthma in patients whose disease cannot be adequately controlled with inhalable glucocorticoids. Lebrikizumab is administered by a subcutaneous injection.

Lebrikizumab blocks interleukin 13 (IL-13), a cytokine (cell-signalling protein) that is produced by Th2 cells, a type of white blood cell. IL-13 is thought to induce the expression of another signalling protein, periostin, by epithelial cells of the bronchi. Periostin, in turn, seems to partake in a number of asthma related problems, such as bronchial hyperresponsiveness, inflammation, and activation and proliferation of airway fibroblasts, which are involved in airway remodelling.

Degradation and Stability of Pharmaceutical Compositions

According to the present invention, delamination resistant pharmaceutical containers comprising a glass composition provide for improved resistance to degradation of, improved stability of, improved resistance to inactivation of, and improved maintenance of levels of a pharmaceutical composition having at least one active pharmaceutical ingredient, for example, PERJETA (pertuzumab), ACTEMRA (tocilizumab), KADCYLA (trastuzumab emtansine), MetMAb (onartuzumab), obinutuzumab, ocrelizumab and lebrikizumab.

In one embodiment of the present invention, the delamination resistant pharmaceutical containers provide improved stability to pharmaceutical compositions contained therein, for example, PERJETA (pertuzumab), ACTEMRA (tocilizumab), KADCYLA (trastuzumab emtansine), MetMAb (onartuzumab), obinutuzumab, ocrelizumab and lebrikizumab. As used herein, the term "stability" refers to the ability of an active pharmaceutical ingredient to essentially retain its physical, chemical and conformational identity and integrity upon storage in the pharmaceutical containers of the invention. Stability is associated with the ability of an active pharmaceutical ingredient to retain its potency and efficacy over a period of time. Instability of an active pharmaceutical ingredient may be associated with, for example, chemical or physical degradation, fragmentation, conformational change, increased toxicity, aggregation (e.g., to form higher order polymers), deglycosylation, modification of glycosylation, oxidation, hydrolysis, or any other structural, chemical or physical modification. Such physical, chemical and/or conformational changes often result in reduced activity or inactivation of the active pharmaceutical ingredient, for example, such that at least one biological activity of the active pharmaceutical ingredient is reduced or eliminated. Alternatively or in addition, such physical, chemical and/or conformational changes often result in the formation of structures toxic to the subject to whom the pharmaceutical composition is administered.

The pharmaceutical containers of the present invention maintain stability of the pharmaceutical compositions, in part, by minimizing or eliminating delamination of the glass composition which forms, at least in part, the pharmaceutical container. In addition, the pharmaceutical containers of the present invention maintain stability of the pharmaceutical compositions, in part, by reducing or preventing the interaction of the active pharmaceutical ingredient with the pharmaceutical container and/or delaminated particles resulting therefrom. By minimizing or eliminating delamination and, further, by reducing or preventing interaction, the pharmaceutical containers thereby reduce or prevent the destabilization of the active pharmaceutical ingredient as found in, for example, PERJETA (pertuzumab), ACTEMRA (tocilizumab), KADCYLA (trastuzumab emtansine), MetMAb (onartuzumab), obinutuzumab, ocrelizumab and lebrikizumab.

The pharmaceutical containers of the present invention provide the additional advantage of preventing loss of active pharmaceutical ingredients. For example, by reducing or preventing the interaction of and, thus, the adherence of, the active pharmaceutical ingredient with the pharmaceutical container and/or delaminated particles resulting therefrom, the level of active pharmaceutical ingredient available for administration to a subject is maintained, as found in, for example, PERJETA (pertuzumab), ACTEMRA (tocilizumab), KADCYLA (trastuzumab emtansine), MetMAb (onartuzumab), obinutuzumab, ocrelizumab and lebrikizumab.

In one embodiment of the present invention, the pharmaceutical composition has a high pH. According to the present invention, it has been discovered that high pHs serve to increase delamination of glass compositions. Accordingly, the pharmaceutical containers of the present invention are particularly suitable for storing and maintaining pharmaceutical compositions having a high pH, for example, pharmaceutical compositions having a pH between about 7 and about 11, between about 7 and about 10, between about 7 and about 9, or between about 7 and about 8.

In additional embodiments, the pharmaceutical containers of the present invention are particularly suitable for storing and maintaining pharmaceutical compositions having phosphate or citrate based buffers. According to the present invention, it has been discovered that phosphate or citrate based buffers serve to increase delamination of glass compositions. According in particular embodiments, the pharmaceutical composition includes a buffer comprising a salt of citrate, e.g., sodium citrate, or SSC. In other embodiments, the pharmaceutical composition includes a buffer comprising a salt of phosphate, e.g., mono or disodium phosphate.

In additional embodiments, the pharmaceutical containers of the present invention are particularly suitable for storing and maintaining active pharmaceutical ingredient that needs to be subsequently formulated. In other embodiments, the pharmaceutical containers of the present invention are particularly suitable for storing and maintaining a lyophilized pharmaceutical composition or active pharmaceutical ingredient that requires reconstitution, for example, by addition of saline.

Assaying for Delamination of Pharmaceutical Containers

As noted above, delamination may result in the release of silica-rich glass flakes into a solution contained within the glass container after extended exposure to the solution. Accordingly, the resistance to delamination may be characterized by the number of glass particulates present in a solution contained within the glass container after exposure to the solution under specific conditions. In order to assess the long-term resistance of the glass container to delamination, an accelerated delamination test was utilized. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp. 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers. Table 7 summarizes some non-limiting examples of sample volumes and numbers of containers for testing is shown below:

TABLE 7

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 2 | 4 | 3.2 | 4 | 10 | 128 |
| 3.5 | 7 | 5.6 | 2 | 10 | 112 |
| 4 | 6 | 4.8 | 3 | 10 | 144 |
| 5 | 10 | 8 | 2 | 10 | 160 |
| 6 | 10 | 8 | 2 | 10 | 160 |

TABLE 7-continued

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 8 | 11.5 | 9.2 | 2 | 10 | 184 |
| 10 | 13.5 | 10.8 | 1 | 10 | 108 |
| 20 | 26 | 20.8 | 1 | 10 | 208 |
| 30 | 37.5 | 30 | 1 | 10 | 300 |
| 50 | 63 | 50.4 | 1 | 10 | 504 |

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles based on the aspect ratio of the particle (i.e., the ratio of the width of the particle to the thickness of the particle). Delamination produces particulate flakes or lamellae which are irregularly shaped and are typically >50 µm in diameter but often >200 µm. The thickness of the flakes is usually greater than about 100 nm and may be as large as about 1 µm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

In the embodiments described herein, glass containers which average less than 3 glass particles with a minimum width of 50 µm and an aspect ratio of greater than 50 per trial following accelerated delamination testing are considered "delamination resistant." In the embodiments described herein, glass containers which average less than 2 glass particles with a minimum width of 50 µm and an aspect ratio of greater than 50 per trial following accelerated delamination testing are considered "delamination-stable." In the embodiments described herein, glass containers which average less than 1 glass particle with a minimum width of 50 µm and an aspect ratio of greater than 50 per trial following accelerated delamination testing are considered "delamination-proof." In the embodiments described herein, glass containers which have 0 glass particles with a minimum width of 50 µm and an aspect ratio of greater than 50 per trial following accelerated delamination testing are considered "delamination-free".

Assessing Stability of Pharmaceutical Compositions

As set forth above, any of a variety of active pharmaceutical ingredients can be incorporated within the claimed pharmaceutical container including, for example, a small molecule, a polypeptide mimetic, a biologic, an antisense RNA, a small interfering RNA (siRNA), etc. These active ingredients degrade in varying manners and, thus, assessing the stability thereof in the pharmaceutical containers of the present invention requires different techniques.

Depending on the nature of the active pharmaceutical ingredient, the stability, maintenance and/or continued efficacy of the pharmaceutical compositions contained within the delamination resistant pharmaceutical containers of the present invention can be evaluated as follows.

Biologics API are often susceptible to degradation and/or inactivation arising from various factors, including pH, temperature, temperature cycling, light, humidity, etc. Biologics API are further susceptible to degradation, inactivation or loss, arising from interaction of the pharmaceutical composition with the pharmaceutical container, or delaminants leeching therefrom. For example, biologics may undergo physical degradation which may render the resulting pharmaceutical composition inactive, toxic or insufficient to achieve the desired effect. Alternatively, or in addition, biologics may undergo structural or conformational changes that can alter the activity of the API, with or without degradation. For example, proteins may undergo unfolding which can result in effective loss and inactivity of the API. Alternatively, or in addition, biologics may adhere to the surface of the container, thereby rendering the API administered to the subject insufficient to achieve the desired effect, e.g., therapeutic effect.

(i) General Methods for Investigation of Biologic Compound Degradation

Depending on the size and complexity of the biologic, methods for analysis of degradation of non-biologic, small molecule API may be applied to biologics. For example, peptides and nucleic acids can be analyzed using any of a number of chromatography and spectrometry techniques applicable to small molecules to determine the size of the molecules, either with or without protease or nuclease digestion. However, as proper secondary and tertiary structures are required for the activity of biologics, particularly protein biologics, confirmation of molecular weight is insufficient to confirm activity of biologics. Protein biologics containing complex post-translational modifications, e.g., glycosylation, are less amenable to analysis using chromatography and spectrometry. Moreover, complex biologics, e.g., vaccines which can include complex peptide mixtures, attenuated or killed viruses, or killed cells, are not amenable to analysis by most chromatography or spectrometry methods.

(ii) In Vitro Functional Assays for Investigation of Compound Stability

One or more in vitro assays, optionally in combination with one or more in vivo assays, can be used to assess the stability and activity of the API. Functional assays to determine API stability can be selected based on the structural class of the API and the function of the API. Exemplary assays are provided below to confirm the activity of the API after stability and/or stress testing. It is understood that assays should be performed with the appropriate controls (e.g., vehicle controls, control API not subject to stress or stability testing) with a sufficient number of dilutions and replicate samples to provide data with sufficient statistical significance to detect changes in activity of 10% or less, preferably 5% or less, 4% or less, more preferably 3% or less, 2% or less, or 1% or less, as desired. Such considerations in the art are well understood.

For example, antibody based therapeutics, regardless of the disease or condition to be treated, can be assayed for stability and activity using assays that require specific binding of the antibody to its cognate antigen, e.g., ELISA. The antigen used in the ELISA should have the appropriate conformational structure as would be found in vivo. Antibody based API are used, for example, for the treatment of cancer and inflammatory diseases including autoimmune diseases.

ELISA assays to assay the concentration of a protein biologic API are commercially available from a number of sources, e.g., R&D Systems, BD Biosciences, AbCam, Pierce, Invitrogen.

API are frequently targeted to receptors, particularly cell surface receptors. Receptor binding assays can be used to assess the activity of such agents. API that bind cell surface receptors can be agonists, antagonists or allosteric modulators. API that bind cell surface receptors need not bind the same location as the native ligand to modulate, for example, inhibit or enhance, signaling through the receptor. Depending on the activity of the API, an appropriate assay can be selected, e.g., assay for stimulation of receptor signaling when the API is a receptor agonist; and inhibition assay in which binding of an agonist, e.g., inhibition of activation by a receptor agonist by the API. Such assays can be used regardless of the disease(s) or condition(s) to be treated with the API. Modulation of cellular activity, e.g., cell proliferation, apoptosis, cell migration, modulation of expression of genes or proteins, differentiation, tube formation, etc. is assayed using routine methods. In other assay methods, a reporter construct is used to indicate activation of the receptor. Such methods are routine in the art. APIs that bind to cell surface receptors are used, for example, as anti-cancer agents, anti-diabetic agents, anti-inflammatory agents for the treatment of inflammatory mediated diseases including autoimmune disorders, anti-angiogenic agents, anti-cholinergic agents, bone calcium regulators, muscle and vascular tension regulators, and psychoactive agents.

Modulators of cell proliferation can be assayed for activity using a cell proliferation assays. For example, cell proliferation is induced using anti-anemic agents or stimulators of hematopoietic cell growth. Anti-proliferative agents, e.g., cytotoxic agents, anti-neoplastic agents, chemotherapeutic agents, cytostatic agents, antibiotic agents, are used to inhibit growth of various cell types. Some anti-inflammatory agents also act by inhibiting proliferation of immune cells, e.g., blast cells. In proliferation assays, replicate wells containing the same number of cells are cultured in the presence of the API. The effect of the API is assessed using, for example, microscopy or fluorescence activated cell sorting (FACS) to determine if the number of cells in the sample increased or decreased in response to the presence of the API. It is understood that the cell type selected for the proliferation assay is dependent on the specific API to be tested.

Modulators of angiogenesis can be assayed using cell migration and/or tube formation assays. For cell migration assays, human vascular endothelial cells (HUVECs) are cultured in the presence of the API in transwell devices. Migration of cells through the device at the desired time intervals is assessed. Alternatively, 3-dimensional HUVECs cultures in MATRIGEL can be assessed for tube formation. Anti-angiogenic agents are used, for example, for the treatment of cancer, macular degeneration, and diabetic retinopathy.

Anti-inflammatory API can be assayed for their effects on immune cell stimulation as determined, for example, by modulation of one or more of cytokine expression and secretion, antigen presentation, migration in response to cytokine or chemokine stimulation, and immune cell proliferation. In such assays, immune cells are cultured in the presence of the API and changes in immune cell activity are determined using routine methods in the art, e.g., ELISA and cell imaging and counting.

Anti-diabetic API can be assayed for their effects on insulin signaling, including insulin signaling in response to modulated glucose levels, and insulin secretion. Insulin signaling can be assessed by assessing kinase activation in response to exposure to insulin and/or modulation of glucose levels. Insulin secretion can be assessed by ELISA assay.

Modulators of blood clotting, i.e., fibrinolytics, anti-fibrinolytics, and anti-coagulants, can be assayed for their effects using an INR assay on serum by measuring prothrombin time to determine a prothrombin ratio. Time to formation of a clot is assayed in the presence or absence of the API.

Modulators of muscle or vascular tone can be assayed for their effects using vascular or muscle explants. The tissue can be placed in a caliper for detection of changes in length and/or tension. Whole coronary explants can be used to assess the activity of API on heart. The tissue is contacted with the API, and optionally agents to alter vascular tone (e.g., $K^+$, $Ca^{++}$). The effects of the API on length and/or tension of the vasculature or muscle is assessed.

Psychoactive agents can act by modulation of neurotransmitter release and/or recycling. Neuronal cells can be incubated in the presence of an API and stimulated to release neurotransmitters. Neurotransmitter levels can be assessed in the culture medium collected at defined time points to detect alterations in the level of neurotransmitter present in the media. Neurotransmitters can be detected, for example, using ELISA, LC/MS/MS, or by preloading the vesicles with radioactive neurotransmitters to facilitate detection.

(iii) In Vivo Assays for Investigation of Compound Stability

In addition to in vitro testing for compound stability, API can also be tested in vivo to confirm the stability of the API after storage and/or stress testing. For example, some API are not amenable to testing using in vitro assays due to the complexity of the disease state or the complexity of the response required. For example, psychoactive agents, e.g., antipsychotic agents, anti-depressant agents, nootropic agents, immunosuppressant agents, vasotherapeutic agents, muscular dystrophy agents, central nervous system modulating agents, antispasmodic agents, bone calcium regenerating agents, anti-rheumatic agents, anti-hyperlipidemic agents, hematopoietic proliferation agents, growth factors, vaccine agents, and imaging agents, may not be amenable to full functional characterization using in vitro models. Moreover, for some agents, factors that may not alter in vitro activity may alter activity in vivo, e.g., antibody variable domains may be sufficient to block signaling through a receptor, but the Fc domains may be required for efficacy in the treatment of disease. Further, changes in stability may result in changes in pharmacokinetic properties of an API (e.g., half-life, serum protein binding, tissue distribution, CNS permeability). Finally, changes in stability may result in the generation of toxic degradation or reaction products that would not be detected in vivo. Therefore, confirmation of pharmacokinetic and pharmacodynamic properties and toxicity in vivo is useful in conjunction with stability and stress testing.

(iv) Pharmacokinetic Assays

Pharmacokinetics includes the study of the mechanisms of absorption and distribution of an administered drug, the rate at which a drug action begins and the duration of the effect, the chemical changes of the substance in the body (e.g. by metabolic enzymes such as CYP or UGT enzymes) and the effects and routes of excretion of the metabolites of the drug. Pharmacokinetics is divided into several areas including the extent and rate of absorption, distribution, metabolism and excretion. This is commonly referred to as the ADME scheme:

Absorption—the process of a substance entering the blood circulation.

Distribution—the dispersion or dissemination of substances throughout the fluids and tissues of the body.

Metabolism (or Biotransformation)—the irreversible transformation of parent compounds into daughter metabolites.

Excretion—the removal of the substances from the body. In rare cases, some drugs irreversibly accumulate in body tissue.

Elimination is the result of metabolism and excretion.

Pharmacokinetics describes how the body affects a specific drug after administration. Pharmacokinetic properties of drugs may be affected by elements such as the site of administration and the dose of administered drug, which may affect the absorption rate. Such factors cannot be fully assessed using in vitro models.

The specific pharmacokinetic properties to be assessed for a specific API in stability testing will depend, for example, on the specific API to be tested. In vitro pharmacokinetic assays can include assays of drug metabolism by isolated enzymes or by cells in culture. However, pharmacokinetic analysis typically requires analysis in vivo.

As pharmacokinetics are not concerned with the activity of the drug, but instead with the absorption, distribution, metabolism, and excretion of the drug, assays can be performed in normal subjects, rather than subjects suffering from a disease or condition for which the API is typically administered, by administration of a single dose of the API to the subject. However, if the subject to be treated with the API has a condition that would alter the metabolism or excretion of the API, e.g., liver disease, kidney disease, testing of the API in an appropriate disease model may be useful. Depending on the half life of the compound, samples (e.g., serum, urine, stool) are collected at predetermined time points for at least two, preferably three half-lives of the API, and analyzed for the presence of the API and metabolic products of the API. At the end of the study, organs are harvested and analyzed for the presence of the API and metabolic products of the API. The pharmacokinetic properties of the API subjected to stability and/or stress testing are compared to API not subjected to stability or stress testing and other appropriate controls (e.g., vehicle control). Changes in pharmacokinetic properties as a result of stability and/or stress testing are determined.

(v) Pharmacodynamic Assays

Pharmacodynamics includes the study of the biochemical and physiological effects of drugs on the body or on microorganisms or parasites within or on the body and the mechanisms of drug action and the relationship between drug concentration and effect. Due to the complex nature of many disease states and the actions of many API, the API should be tested in vivo to confirm the desired activity of the agent. Mouse models for a large variety of disease states are known and commercially available (see, e.g., jaxmice.jax.org/query/f?p=205:1:989373419139701::::P1_ADV:1). A number of induced models of disease are also known. Agents can be tested on the appropriate animal model to demonstrate stability and efficacy of the API on modulating the disease state.

(vi) Specific Immune Response Assay

Vaccines produce complex immune responses that are best assessed in vivo. The specific potency assay for a vaccine depends, at least in part, on the specific vaccine type. The most accurate predictions are based on mathematical modeling of biologically relevant stability-indicating parameters. For complex vaccines, e.g., whole cell vaccines, whole virus vaccines, complex mixtures of antigens, characterization of each component biochemically may be difficult, if not impossible. For example, when using a live, attenuated virus vaccine, the number of plaque forming units (e.g., mumps, measles, rubella, smallpox) or colony forming units (e.g., *S. typhi*, TY21a) are determined to confirm potency after storage. Chemical and physical characterization (e.g., polysaccharide and polysaccharide-protein conjugate vaccines) is performed to confirm the stability and activity of the vaccine. Serological response in animals to inactivated toxins and/or animal protection against challenge (e.g., rabies, anthrax, diphtheria, tetanus) is performed to confirm activity of vaccines of any type, particularly when the activity of the antigen has been inactivated. In vivo testing of vaccines subjected to stability and/or stress testing is performed by administering the vaccine to a subject using the appropriate immunization protocol for the vaccine, and determining the immune response by detection of specific immune cells that respond to stimulation with the antigen or pathogen, detection of antibodies against the antigen or pathogen, or protection in an immune challenge. Such methods are well known in the art. Vaccines include, but are not limited to, meningococcal B vaccine, hepatitis A and B vaccines, human papillomavirus vaccine, influenza vaccine, herpes zoster vaccine, and pneumococcal vaccine.

(vii) Toxicity Assays

Degradation of API can result in the formation of toxic agents. Toxicity assays include the administration of doses, typically far higher than would be used for therapeutic applications, to detect the presence of toxic products in the API. Toxicity assays can be performed in vitro and in vivo and are frequently single, high dose experiments. After administration of the compound, in addition to viability, organs are harvested and analyzed for any indication of toxicity, especially organs involved with clearance of API, e.g., liver, kidneys, and those for which damage could be catastrophic, e.g., heart, brain. The toxicologic properties of the API subjected to stability and/or stress testing are compared to API not subjected to stability or stress testing and other appropriate controls (e.g., vehicle control). Changes in toxicologic properties as a result of stability and/or stress testing are determined.

In accordance with present invention, the degradation, alteration or depletion of API contained within a delamination resistant pharmaceutical container of the present invention can be assessed by a variety of physical techniques. Indeed, in various aspects of the invention, the stability and degradation caused by the interaction of API with the container or delaminants thereof, or changes in concentration or amount of the API in a container can be assessed using techniques as follows. Such methods include, e.g., X-Ray Diffraction (XRPD), Thermal Analysis (such as Differential Scanning calorimetry (DSC), Thermogravimetry (TG) and Hot-Stage Microscopy (HSM), chromatography methods (such as High-Performance Liquid Chromatography (HPLC), Column Chromatography (CC), Gas Chromatography (GC), Thin-Layer Chromatography (TLC), and Super Critical Phase Chromatograph (SFC)), Mass Spectroscopy (MS), Capillary Electrophoresis (CE), Atomic Spectroscopy (AS), vibrational spectroscopy (such as Infrared Spectroscopy (IR)), Luminescence Spectroscopy (LS), and Nuclear Magnetic Resonance Spectroscopy (NMR).

In the case of pharmaceutical formulations where the API is not in solution or needs to be reconstituted into a different medium, XRPD may be a method for analyzing degradation. In ideal cases, every possible crystalline orientation is represented equally in a non-liquid sample.

Powder diffraction data is usually presented as a diffractogram in which the diffracted intensity I is shown as function either of the scattering angle $2\theta$ or as a function of the scattering vector q. The latter variable has the advantage that the diffractogram no longer depends on the value of the wavelength $\lambda$. Relative to other methods of analysis, powder diffraction allows for rapid, non-destructive analysis of multi-component mixtures without the need for extensive sample preparation. Deteriorations of an API may be analyzed using this method, e.g., by comparing the diffraction pattern of the API to a known standard of the API prior to packaging.

Thermal methods of analysis may include, e.g., differential scanning calorimetry (DSC), thermogravimetry (TG), and hot-stage microscopy (HSM). All three methods provide information upon heating the sample. Depending on the information required, heating can be static or dynamic in nature.

Differential scanning calorimetry monitors the energy required to maintain the sample and a reference at the same temperature as they are heated. A plot of heat flow (W/g or J/g) versus temperature is obtained. The area under a DSC peak is directly proportional to the heat absorbed or released and integration of the peak results in the heat of transition.

Thermogravimetry (TG) measures the weight change of a sample as a function of temperature. A total volatile content of the sample is obtained, but no information on the identity of the evolved gas is provided. The evolved gas must be identified by other methods, such as gas chromatography, Karl Fisher titration (specifically to measure water), TG-mass spectroscopy, or TG-infrared spectroscopy. The temperature of the volatilization and the presence of steps in the TG curve can provide information on how tightly water or solvent is held in the lattice. If the temperature of the TG volatilization is similar to an endothermic peak in the DSC, the DSC peak is likely due or partially due to volatilization. It may be necessary to utilize multiple techniques to determine if more than one thermal event is responsible for a given DSC peak.

Hot-Stage Microscopy (HSM) is a technique that supplements DSC and TG. Events observed by DSC and/or TG can be readily characterized by HSM. Melting, gas evolution, and solid-solid transformations can be visualized, providing the most straightforward means of identifying thermal events. Thermal analysis can be used to determine the melting points, recrystallizations, solid-state transformations, decompositions, and volatile contents of pharmaceutical materials.

Other methods to analyze degradation or alteration of API and excipients are infrared (IR) and Raman spectroscopy. These techniques are sensitive to the structure, conformation, and environment of organic compounds. Infrared spectroscopy is based on the conversion of IR radiation into molecular vibrations. For a vibration to be IR-active, it must involve a changing molecular dipole (asymmetric mode). For example, vibration of a dipolar carbonyl group is detectable by IR spectroscopy. Whereas IR has been traditionally used as an aid in structure elucidation, vibrational changes also serve as probes of intermolecular interactions in solid materials.

Raman spectroscopy is based on the inelastic scattering of laser radiation with loss of vibrational energy by a sample. A vibrational mode is Raman active when there is a change in the polarizability during the vibration. Symmetric modes tend to be Raman-active. For example, vibrations about bonds between the same atom, such as in alkynes, can be observed by Raman spectroscopy.

NMR spectroscopy probes atomic environments based on the different resonance frequencies exhibited by nuclei in a strong magnetic field. Many different nuclei are observable by the NMR technique, but those of hydrogen and carbon atoms are most frequently studied. Solid-state NMR measurements are extremely useful for characterizing the crystal forms of pharmaceutical solids. Nuclei that are typically analyzed with this technique include those of 13C, 31P, 15N, 25Mg, and 23Na.

Chromatography is a general term applied to a wide variety of separation techniques based on the sample partitioning between a moving phase, which can be a gas, liquid, or supercritical fluid, and a stationary phase, which may be either a liquid or a solid. Generally, the crux of chromatography lies in the highly selective chemical interactions that occur in both the mobile and stationary phases. For example, depending on the API and the separation required, one or more of absorption, ion-exchange, size-exclusion, bonded phase, reverse, or normal phase stationary phases may be employed.

Mass spectrometry (MS) is an analytical technique that works by ionizing chemical compounds to generate charged molecules or molecule fragments and measuring their mass-to-charge ratios. Based on this analysis method, one can determine, e.g., the isotopic composition of elements in an API and determine the structure of the API by observing its fragmentation pattern.

It would be understood that the foregoing methods do not represent a comprehensive list of means by which one can analyze possible deteriorations, alterations, or concentrations of certain APIs. Therefore, it would be understood that other methods for determining the physical amounts and/or characteristics of an API may be employed. Additional methods may include, but are not limited to, e.g., Capillary Electrophoresis (CE), Atomic Spectroscopy (AS), and Luminescence Spectroscopy (LS).

EXAMPLES

The embodiments of the delamination resistant pharmaceutical containers described herein will be further clarified by the following examples.

Example 1

Six exemplary inventive glass compositions (compositions A-F) were prepared. The specific compositions of each exemplary glass composition are reported below in Table 8. Multiple samples of each exemplary glass composition were produced. One set of samples of each composition was ion exchanged in a molten salt bath of 100% KNO$_3$ at a temperature of 450° C. for at least 5 hours to induce a compressive layer in the surface of the sample. The compressive layer had a surface compressive stress of at least 500 MPa and a depth of layer of at least 45 μm.

The chemical durability of each exemplary glass composition was then determined utilizing the DIN 12116 standard, the ISO 695 standard, and the ISO 720 standard described above. Specifically, non-ion exchanged test samples of each exemplary glass composition were subjected to testing according to one of the DIN 12116 standard, the ISO 695 standard, or the ISO 720 standard to determine the acid resistance, the base resistance or the hydrolytic resistance of the test sample, respectively. The hydrolytic resistance of the ion exchanged samples of each exemplary composition was determined according to the ISO 720 standard. The average results of all samples tested are reported below in Table 8.

As shown in Table 8, exemplary glass compositions A-F all demonstrated a glass mass loss of less than 5 mg/dm$^2$ and greater than 1 mg/dm$^2$ following testing according to the DIN 12116 standard with exemplary glass composition E having the lowest glass mass loss at 1.2 mg/dm$^2$. Accordingly, each of the exemplary glass compositions were classified in at least class S3 of the DIN 12116 standard, with exemplary glass composition E classified in class S2. Based on these test results, it is believed that the acid resistance of the glass samples improves with increased $SiO_2$ content.

Further, exemplary glass compositions A-F all demonstrated a glass mass loss of less than 80 mg/dm$^2$ following testing according to the ISO 695 standard with exemplary glass composition A having the lowest glass mass loss at 60 mg/dm$^2$. Accordingly, each of the exemplary glass compositions were classified in at least class A2 of the ISO 695 standard, with exemplary glass compositions A, B, D and F classified in class A1. In general, compositions with higher silica content exhibited lower base resistance and compositions with higher alkali/alkaline earth content exhibited greater base resistance.

Table 8 also shows that the non-ion exchanged test samples of exemplary glass compositions A-F all demonstrated a hydrolytic resistance of at least Type HGA2 following testing according to the ISO 720 standard with exemplary glass compositions C-F having a hydrolytic resistance of Type HGA1. The hydrolytic resistance of exemplary glass compositions C-F is believed to be due to higher amounts of $SiO_2$ and the lower amounts of $Na_2O$ in the glass compositions relative to exemplary glass compositions A and B.

Moreover, the ion exchanged test samples of exemplary glass compositions B-F demonstrated lower amounts of extracted $Na_2O$ per gram of glass than the non-ion exchanged test samples of the same exemplary glass compositions following testing according to the ISO 720 standard.

TABLE 8

Composition and Properties of Exemplary Glass Compositions

| | Composition in mole % | | | | | |
|---|---|---|---|---|---|---|
| | A | B | C | D | E | F |
| $SiO_2$ | 70.8 | 72.8 | 74.8 | 76.8 | 76.8 | 77.4 |
| $Al_2O_3$ | 7.5 | 7 | 6.5 | 6 | 6 | 7 |
| $Na_2O$ | 13.7 | 12.7 | 11.7 | 10.7 | 11.6 | 10 |
| $K_2O$ | 1 | 1 | 1 | 1 | 0.1 | 0.1 |
| MgO | 6.3 | 5.8 | 5.3 | 4.8 | 4.8 | 4.8 |

TABLE 8-continued

Composition and Properties of Exemplary Glass Compositions

| | Composition in mole % | | | | | |
|---|---|---|---|---|---|---|
| | A | B | C | D | E | F |
| CaO | 0.5 | 0.5 | 0.5 | 0.5 | 0.5 | 0.5 |
| $SnO_2$ | 0.2 | 0.2 | 0.2 | 0.2 | 0.2 | 0.2 |
| DIN 12116 (mg/dm$^2$) | 3.2 | 2.0 | 1.7 | 1.6 | 1.2 | 1.7 |
| classification | S3 | S3 | S3 | S3 | S2 | S3 |
| ISO 695 (mg/dm$^2$) | 60.7 | 65.4 | 77.9 | 71.5 | 76.5 | 62.4 |
| classification | A1 | A1 | A2 | A1 | A2 | A1 |
| ISO 720 (ug $Na_2O$/ g glass) | 100.7 | 87.0 | 54.8 | 57.5 | 50.7 | 37.7 |
| classification | HGA2 | HGA2 | HGA1 | HGA1 | HGA1 | HGA1 |
| ISO 720 (with IX) (ug $Na_2O$/ g glass) | 60.3 | 51.9 | 39.0 | 30.1 | 32.9 | 23.3 |
| classification | HGA1 | HGA1 | HGA1 | HGA1 | HGA1 | HGA1 |

Example 2

Three exemplary inventive glass compositions (compositions G-I) and three comparative glass compositions (compositions 1-3) were prepared. The ratio of alkali oxides to alumina (i.e., Y:X) was varied in each of the compositions in order to assess the effect of this ratio on various properties of the resultant glass melt and glass. The specific compositions of each of the exemplary inventive glass compositions and the comparative glass compositions are reported in Table 9. The strain point, anneal point, and softening point of melts formed from each of the glass compositions were determined and are reported in Table 2. In addition, the coefficient of thermal expansion (CTE), density, and stress optic coefficient (SOC) of the resultant glasses were also determined and are reported in Table 9. The hydrolytic resistance of glass samples formed from each exemplary inventive glass composition and each comparative glass composition was determined according to the ISO 720 Standard both before ion exchange and after ion exchange in a molten salt bath of 100% $KNO_3$ at 450° C. for 5 hours. For those samples that were ion exchanged, the compressive stress was determined with a fundamental stress meter (FSM) instrument, with the compressive stress value based on the measured stress optical coefficient (SOC). The FSM instrument couples light into and out of the birefringent glass surface. The measured birefringence is then related to stress through a material constant, the stress-optic or photoelastic coefficient (SOC or PEC) and two parameters are obtained: the maximum surface compressive stress (CS) and the exchanged depth of layer (DOL). The diffusivity of the alkali ions in the glass and the change in stress per square root of time were also determined.

TABLE 9

Glass properties as a function of alkali to alumina ratio
Composition Mole %

| | G | H | I | 1 | 2 | 3 |
|---|---|---|---|---|---|---|
| $SiO_2$ | 76.965 | 76.852 | 76.962 | 76.919 | 76.960 | 77.156 |
| $Al_2O_3$ | 5.943 | 6.974 | 7.958 | 8.950 | 4.977 | 3.997 |
| $Na_2O$ | 11.427 | 10.473 | 9.451 | 8.468 | 12.393 | 13.277 |
| $K_2O$ | 0.101 | 0.100 | 0.102 | 0.105 | 0.100 | 0.100 |
| MgO | 4.842 | 4.878 | 4.802 | 4.836 | 4.852 | 4.757 |

TABLE 9-continued

Glass properties as a function of alkali to alumina ratio
Composition Mole %

|  | G | H | I | 1 | 2 | 3 |
|---|---|---|---|---|---|---|
| CaO | 0.474 | 0.478 | 0.481 | 0.480 | 0.468 | 0.462 |
| $SnO_2$ | 0.198 | 0.195 | 0.197 | 0.197 | 0.196 | 0.196 |
| Strain (° C.) | 578 | 616 | 654 | 683 | 548 | 518 |
| Anneal (° C.) | 633 | 674 | 716 | 745 | 600 | 567 |
| Softening (° C.) | 892 | 946 | 1003 | 1042 | 846 | 798 |
| Expansion ($10^{-7}$ $K^{-1}$) | 67.3 | 64.3 | 59.3 | 55.1 | 71.8 | 74.6 |
| Density (g/cm³) | 2.388 | 2.384 | 2.381 | 2.382 | 2.392 | 2.396 |
| SOC (nm/mm/Mpa) | 3.127 | 3.181 | 3.195 | 3.232 | 3.066 | 3.038 |
| ISO720 (non-IX) | 88.4 | 60.9 | 47.3 | 38.4 | 117.1 | 208.1 |
| ISO720 (IX450° C.-5 hr) | 25.3 | 26 | 20.5 | 17.8 | 57.5 | 102.5 |
| $R_2O/Al_2O_3$ | 1.940 | 1.516 | 1.200 | 0.958 | 2.510 | 3.347 |
| CS@t = 0 (MPa) | 708 | 743 | 738 | 655 | 623 | 502 |
| CS/√t (MPa/hr$^{1/2}$) | −35 | −24 | −14 | −7 | −44 | −37 |
| D (μm²/hr) | 52.0 | 53.2 | 50.3 | 45.1 | 51.1 | 52.4 |

The data in Table 9 indicates that the alkali to alumina ratio Y:X influences the melting behavior, hydrolytic resistance, and the compressive stress obtainable through ion exchange strengthening. In particular, FIG. 1 graphically depicts the strain point, anneal point, and softening point as a function of Y:X ratio for the glass compositions of Table 9. FIG. 1 demonstrates that, as the ratio of Y:X decreases below 0.9, the strain point, anneal point, and softening point of the glass rapidly increase. Accordingly, to obtain a glass which is readily meltable and formable, the ratio Y:X should be greater than or equal to 0.9 or even greater than or equal to 1.

Further, the data in Table 2 indicates that the diffusivity of the glass compositions generally decreases with the ratio of Y:X. Accordingly, to achieve glasses can be rapidly ion exchanged in order to reduce process times (and costs) the ratio of Y:X should be greater than or equal to 0.9 or even greater than or equal to 1.

Figure 2:
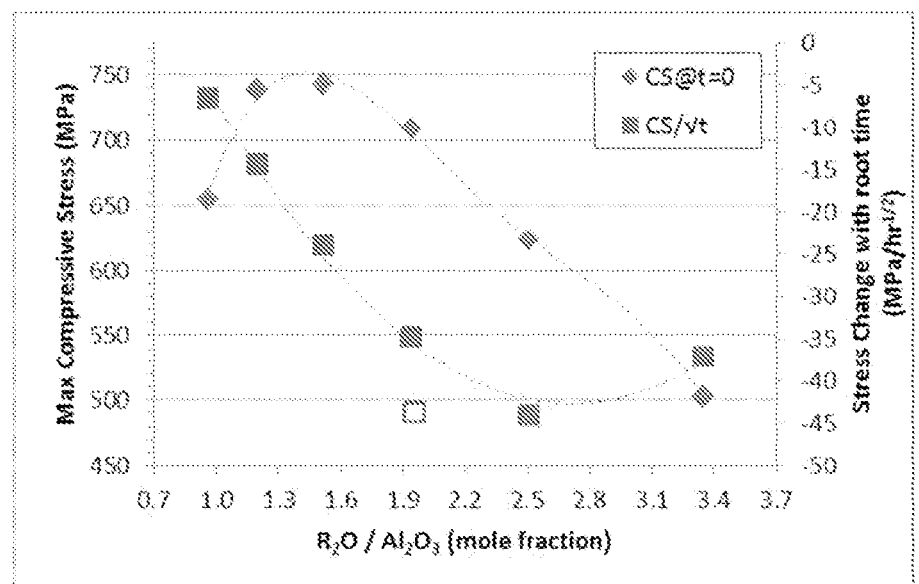
FIG. 2 graphically depicts the relationship between the ratio of alkali oxides to alumina (x-axis) and the maximum compressive stress and stress change (y-axes) of inventive and comparative glass compositions.

Moreover, FIG. 2 indicates that for a given ion exchange time and ion exchange temperature, the maximum compressive stresses are obtained when the ratio of Y:X is greater than or equal to about 0.9, or even greater than or equal to about 1, and less than or equal to about 2, specifically greater than or equal to about 1.3 and less than or equal to about 2.0. Accordingly, the maximum improvement in the load bearing strength of the glass can be obtained when the ratio of Y:X is greater than about 1 and less than or equal to about 2. It is generally understood that the maximum stress achievable by ion exchange will decay with increasing ion-exchange duration as indicated by the stress change rate (i.e., the measured compressive stress divided by the square root of the ion exchange time). FIG. 2 generally shows that the stress change rate decreases as the ratio Y:X decreases.

Figure 3:
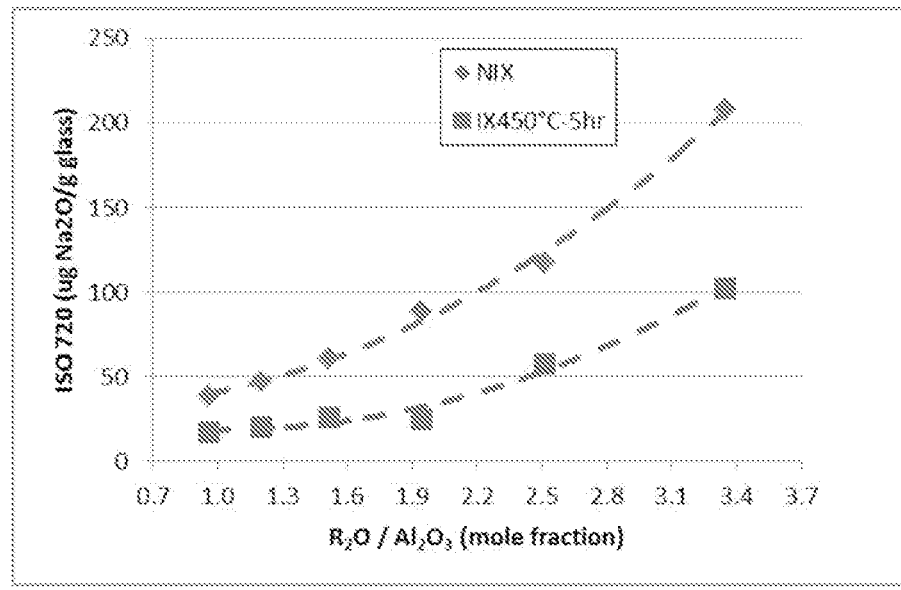
FIG. 3 graphically depicts the relationship between the ratio of alkali oxides to alumina (x-axis) and hydrolytic resistance as determined from the ISO 720 standard (y-axis) of inventive and comparative glass compositions.

FIG. 3 graphically depicts the hydrolytic resistance (y-axis) as a function of the ratio Y:X (x-axis). As shown in FIG. 3, the hydrolytic resistance of the glasses generally improves as the ratio Y:X decreases.

Based on the foregoing it should be understood that glasses with good melt behavior, superior ion exchange performance, and superior hydrolytic resistance can be achieved by maintaining the ratio Y:X in the glass from greater than or equal to about 0.9, or even greater than or equal to about 1, and less than or equal to about 2.

Example 3

Three exemplary inventive glass compositions (compositions J-L) and three comparative glass compositions (compositions 4-6) were prepared. The concentration of MgO and CaO in the glass compositions was varied to produce both MgO-rich compositions (i.e., compositions J-L and 4) and CaO-rich compositions (i.e., compositions 5-6). The relative amounts of MgO and CaO were also varied such that the glass compositions had different values for the ratio (CaO/(CaO+MgO)). The specific compositions of each of the exemplary inventive glass compositions and the comparative glass compositions are reported below in Table 10. The properties of each composition were determined as described above with respect to Example 2.

TABLE 10

Glass properties as function of CaO content
Composition Mole %

|  | J | K | L | 4 | 5 | 6 |
|---|---|---|---|---|---|---|
| $SiO_2$ | 76.99 | 77.10 | 77.10 | 77.01 | 76.97 | 77.12 |
| $Al_2O_3$ | 5.98 | 5.97 | 5.96 | 5.96 | 5.97 | 5.98 |
| $Na_2O$ | 11.38 | 11.33 | 11.37 | 11.38 | 11.40 | 11.34 |
| $K_2O$ | 0.10 | 0.10 | 0.10 | 0.10 | 0.10 | 0.10 |
| MgO | 5.23 | 4.79 | 3.78 | 2.83 | 1.84 | 0.09 |
| CaO | 0.07 | 0.45 | 1.45 | 2.46 | 3.47 | 5.12 |
| $SnO_2$ | 0.20 | 0.19 | 0.19 | 0.19 | 0.19 | 0.19 |
| Strain (° C.) | 585 | 579 | 568 | 562 | 566 | 561 |
| Anneal (° C.) | 641 | 634 | 620 | 612 | 611 | 610 |
| Softening (° C.) | 902 | 895 | 872 | 859 | 847 | 834 |
| Expansion ($10^{-7}$ $K^{-1}$) | 67.9 | 67.1 | 68.1 | 68.8 | 69.4 | 70.1 |
| Density (g/cm³) | 2.384 | 2.387 | 2.394 | 2.402 | 2.41 | 2.42 |

TABLE 10-continued

Glass properties as function of CaO content
Composition Mole %

|  | J | K | L | 4 | 5 | 6 |
|---|---|---|---|---|---|---|
| SOC nm/mm/Mpa | 3.12 | 3.08 | 3.04 | 3.06 | 3.04 | 3.01 |
| ISO720 (non-IX) | 83.2 | 83.9 | 86 | 86 | 88.7 | 96.9 |
| ISO720 (IX450° C.-5 hr) | 29.1 |  | 28.4 | 33.2 | 37.3 | 40.1 |
| Fraction of RO as CaO | 0.014 | 0.086 | 0.277 | 0.465 | 0.654 | 0.982 |
| CS@t = 0 (MPa) | 707 | 717 | 713 | 689 | 693 | 676 |
| CS/√t (MPa/hr$^{1/2}$) | −36 | −37 | −39 | −38 | −43 | −44 |
| D (μm$^2$/hr) | 57.2 | 50.8 | 40.2 | 31.4 | 26.4 | 20.7 |

Figure 4:
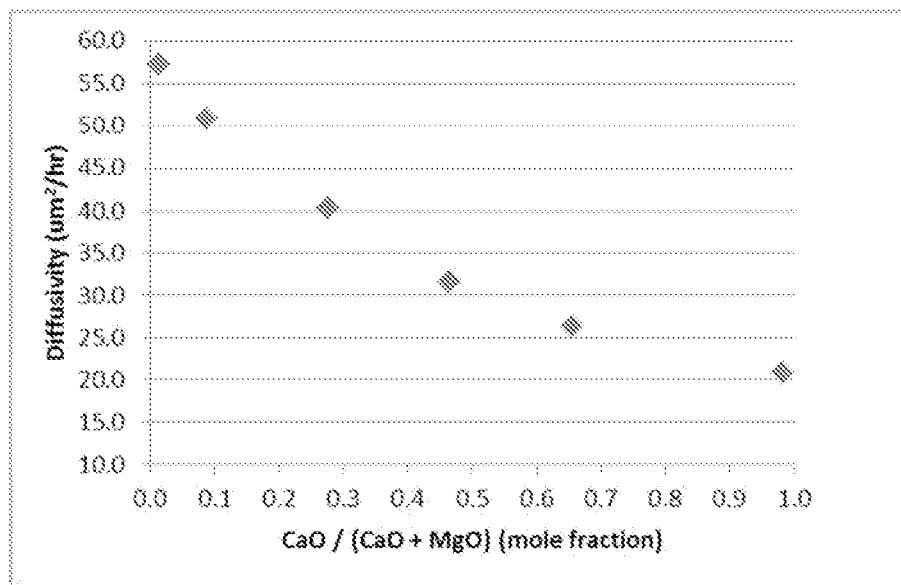
FIG. 4 graphically depicts diffusivity D (y-axis) as a function of the ratio (CaO/(CaO+MgO)) (x-axis) for inventive and comparative glass compositions.
Figure 5:
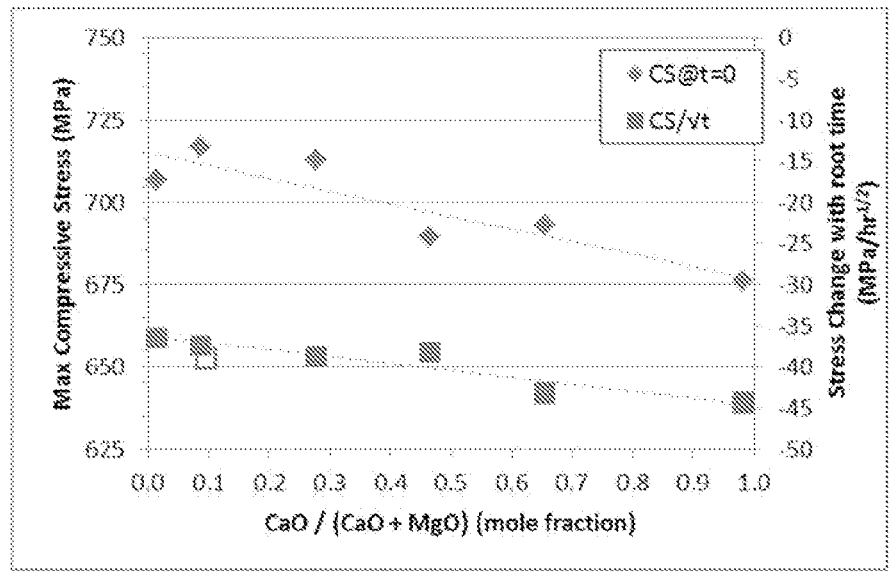
FIG. 5 graphically depicts the maximum compressive stress (y-axis) as a function of the ratio (CaO/(CaO+MgO)) (x-axis) for inventive and comparative glass compositions.

FIG. 4 graphically depicts the diffusivity D of the compositions listed in Table 10 as a function of the ratio (CaO/(CaO+MgO)). Specifically, FIG. 4 indicates that as the ratio (CaO/(CaO+MgO)) increases, the diffusivity of alkali ions in the resultant glass decreases thereby diminishing the ion exchange performance of the glass. This trend is supported by the data in Table 10 and FIG. 5. FIG. 5 graphically depicts the maximum compressive stress and stress change rate (y-axes) as a function of the ratio (CaO/(CaO+MgO)). FIG. 5 indicates that as the ratio (CaO/(CaO+MgO)) increases, the maximum obtainable compressive stress decreases for a given ion exchange temperature and ion exchange time. FIG. 5 also indicates that as the ratio (CaO/(CaO+MgO)) increases, the stress change rate increases (i.e., becomes more negative and less desirable).

Accordingly, based on the data in Table 10 and FIGS. 4 and 5, it should be understood that glasses with higher diffusivities can be produced by minimizing the ratio (CaO/(CaO+MgO)). It has been determined that glasses with suitable diffusivities can be produced when the (CaO/(CaO+MgO)) ratio is less than about 0.5. The diffusivity values of the glass when the (CaO/(CaO+MgO)) ratio is less than about 0.5 decreases the ion exchange process times needed to achieve a given compressive stress and depth of layer. Alternatively, glasses with higher diffusivities due to the ratio (CaO/(CaO+MgO)) may be used to achieve a higher compressive stress and depth of layer for a given ion exchange temperature and ion exchange time.

Moreover, the data in Table 10 also indicates that decreasing the ratio (CaO/(CaO+MgO)) by increasing the MgO concentration generally improves the resistance of the glass to hydrolytic degradation as measured by the ISO 720 standard.

Example 4

Three exemplary inventive glass compositions (compositions M-O) and three comparative glass compositions (compositions 7-9) were prepared. The concentration of $B_2O_3$ in the glass compositions was varied from 0 mol. % to about 4.6 mol. % such that the resultant glasses had different values for the ratio $B_2O_3/(R_2O—Al_2O_3)$. The specific compositions of each of the exemplary inventive glass compositions and the comparative glass compositions are reported below in Table 11. The properties of each glass composition were determined as described above with respect to Examples 2 and 3.

TABLE 11

Glass properties as a function of $B_2O_3$ content
Composition Mole %

|  | M | N | O | 7 | 8 | 9 |
|---|---|---|---|---|---|---|
| SiO$_2$ | 76.860 | 76.778 | 76.396 | 74.780 | 73.843 | 72.782 |
| Al$_2$O$_3$ | 5.964 | 5.948 | 5.919 | 5.793 | 5.720 | 5.867 |
| B$_2$O$_3$ | 0.000 | 0.214 | 0.777 | 2.840 | 4.443 | 4.636 |
| Na$_2$O | 11.486 | 11.408 | 11.294 | 11.036 | 10.580 | 11.099 |
| K$_2$O | 0.101 | 0.100 | 0.100 | 0.098 | 0.088 | 0.098 |
| MgO | 4.849 | 4.827 | 4.801 | 4.754 | 4.645 | 4.817 |
| CaO | 0.492 | 0.480 | 0.475 | 0.463 | 0.453 | 0.465 |
| SnO$_2$ | 0.197 | 0.192 | 0.192 | 0.188 | 0.183 | 0.189 |
| Strain (° C.) | 579 | 575 | 572 | 560 | 552 | 548 |
| Anneal (° C.) | 632 | 626 | 622 | 606 | 597 | 590 |
| Softening (° C.) | 889 | 880 | 873 | 836 | 816 | 801 |
| Expansion (10$^{-7}$ K$^{-1}$) | 68.3 | 67.4 | 67.4 | 65.8 | 64.1 | 67.3 |
| Density (g/cm$^3$) | 2.388 | 2.389 | 2.390 | 2.394 | 2.392 | 2.403 |
| SOC (nm/mm/MPa) | 3.13 | 3.12 | 3.13 | 3.17 | 3.21 | 3.18 |
| ISO720 (non-IX) | 86.3 | 78.8 | 68.5 | 64.4 | 52.7 | 54.1 |
| ISO720 (IX450° C.-5 hr) | 32.2 | 30.1 | 26 | 24.7 | 22.6 | 26.7 |
| B$_2$O$_3$/(R$_2$O—Al$_2$O$_3$) | 0.000 | 0.038 | 0.142 | 0.532 | 0.898 | 0.870 |
| CS@t = 0 (MPa) | 703 | 714 | 722 | 701 | 686 | 734 |
| CS/√t (MPa/hr$^{1/2}$) | −38 | −38 | −38 | −33 | −32 | −39 |
| D (μm$^2$/hr) | 51.7 | 43.8 | 38.6 | 22.9 | 16.6 | 15.6 |

Figure 6:
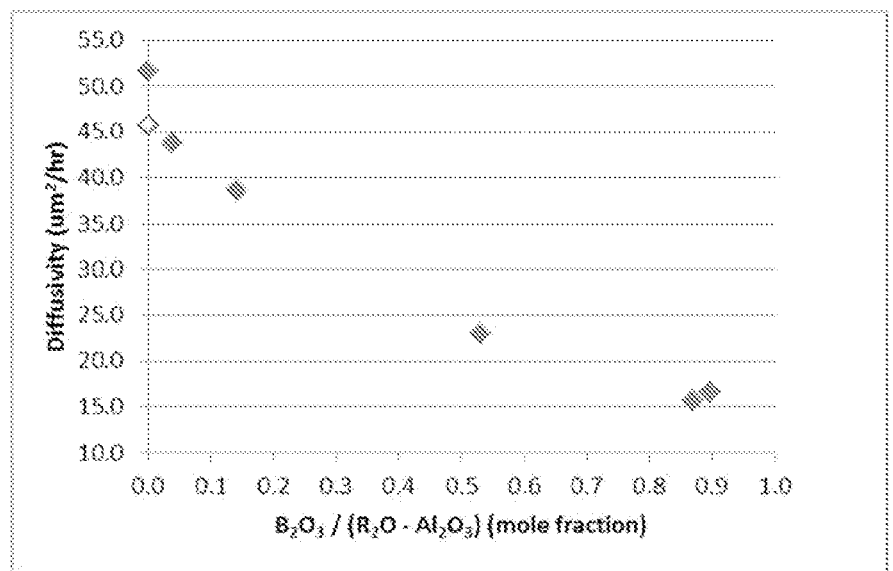
FIG. 6 graphically depicts diffusivity D (y-axis) as a function of the ratio ($B_2O_3/(R_2O-Al_2O_3)$) (x-axis) for inventive and comparative glass compositions.

FIG. 6 graphically depicts the diffusivity D (y-axis) of the glass compositions in Table 11 as a function of the ratio $B_2O_3/(R_2O—Al_2O_3)$ (x-axis) for the glass compositions of Table 11. As shown in FIG. 6, the diffusivity of alkali ions in the glass generally decreases as the ratio $B_2O_3/(R_2O—Al_2O_3)$ increases.

Figure 7:
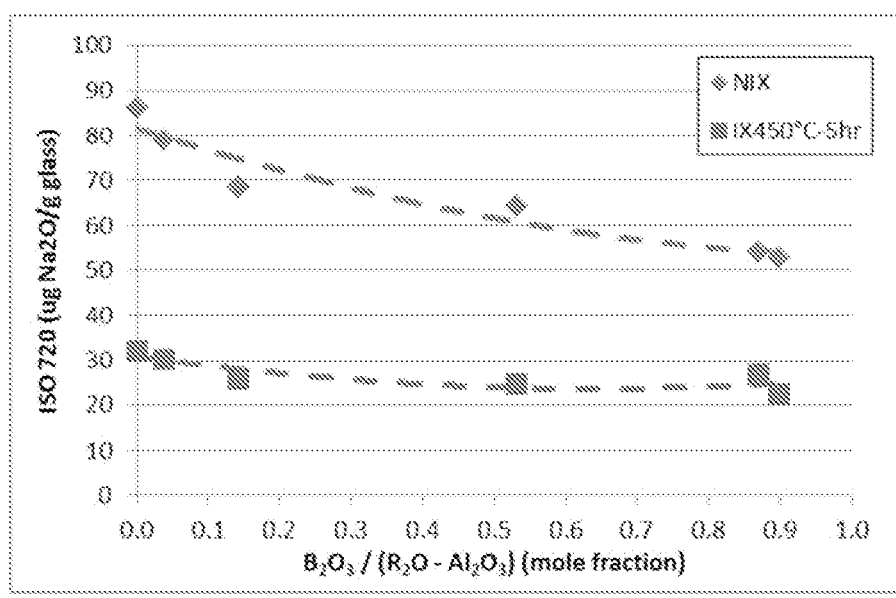
FIG. 7 graphically depicts the hydrolytic resistance as determined from the ISO 720 standard (y-axis) as a function of the ratio ($B_2O_3/(R_2O-Al_2O_3)$) (x-axis) for inventive and comparative glass compositions.

FIG. 7 graphically depicts the hydrolytic resistance according to the ISO 720 standard (y-axis) as a function of the ratio $B_2O_3/(R_2O—Al_2O_3)$ (x-axis) for the glass compositions of Table 11. As shown in FIG. 6, the hydrolytic resistance of the glass compositions generally improves as the ratio $B_2O_3/(R_2O—Al_2O_3)$ increases.

Based on FIGS. 6 and 7, it should be understood that minimizing the ratio $B_2O_3/(R_2O—Al_2O_3)$ improves the diffusivity of alkali ions in the glass thereby improving the ion exchange characteristics of the glass. Further, increasing the ratio $B_2O_3/(R_2O—Al_2O_3)$ also generally improves the resistance of the glass to hydrolytic degradation. In addition, it has been found that the resistance of the glass to degradation in acidic solutions (as measured by the DIN 12116 standard) generally improves with decreasing concentrations of $B_2O_3$. Accordingly, it has been determined that maintaining the ratio $B_2O_3/(R_2O—Al_2O_3)$ to less than or equal to about 0.3 provides the glass with improved hydrolytic and acid resistances as well as providing for improved ion exchange characteristics.

It should now be understood that the glass compositions described herein exhibit chemical durability as well as mechanical durability following ion exchange. These properties make the glass compositions well suited for use in various applications including, without limitation, pharmaceutical packaging materials.

Example 5: Determining the Presence and Amount of Glass Flakes in Pharmaceutical Solutions The resistance to delamination may be characterized by the number of glass particulates present in a pharmaceutical solution contained within a glass container described herein after. In order to assess the long-term resistance of the glass container to delamination, an accelerated delamination test is utilized. The test consists of washing the glass container at room temperature for 1 minute and depyrogenating the container at about 320° C. for 1 hour. Thereafter a pharmaceutical solution is placed in the glass container to 80-90% full, the glass container is closed, and rapidly heated to, for example, 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the pharmaceutical solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp. 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers.

It should be understood that the aforementioned test is used to identify particles which are shed from the interior wall(s) of the glass container due to delamination and not tramp particles present in the container from forming processes. Specifically, delamination particles will be differentiated from tramp glass particles based on the aspect ratio of the particle (i.e., the ratio of the width of the particle to the thickness of the particle). Delamination produces particulate flakes or lamellae which are irregularly shaped and are typically >50 μm in diameter but often >200 μm. The thickness of the flakes is usually greater than about 100 nm and may be as large as about 1 μm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

Using this method, pharmaceutical compositions can be tested for the presence of glass flakes and various compositions can be compared to each other to assess the safety of various pharmaceutical compositions.

Example 6: Stability Testing of Pharmaceutical Compositions

Stability studies are part of the testing required by the FDA and other regulatory agencies. Stability studies should include testing of those attributes of the API that are susceptible to change during storage and are likely to influence quality, safety, and/or efficacy. The testing should cover, as appropriate, the physical, chemical, biological, and microbiological attributes of the API (e.g., small molecule or biologic therapeutic agent) in the container with the closure to be used for storage of the agent. If the API is formulated as a liquid by the manufacturer, the final formulation should be assayed for stability. If the API is formulated as an agent for reconstitution by the end user using a solution provided by the manufacturer, both the API and the solution for reconstitution are preferably tested for stability as the separate packaged components (e.g., the API subjected to storage reconstituted with solution for reconstitution not subject to storage, API not subject to storage reconstituted with a solution subject to storage, and both API and solution subject to storage). This is particularly the case when the solution for reconstitution includes an active agent (e.g., an adjuvant for reconstitution of a vaccine).

In general, a substance API should be evaluated under storage conditions (with appropriate tolerances) that test its thermal stability and, if applicable, its sensitivity to moisture. The storage conditions and the lengths of studies chosen should be sufficient to cover storage, shipment, and subsequent use.

API should be stored in the container(s) in which the API will be provided to the end user (e.g., vials, ampules, syringes, injectable devices). Stability testing methods provided herein refer to samples being removed from the storage or stress conditions indicated. Removal of a sample preferably refers to removing an entire container from the storage or stress conditions. Removal of a sample should not be understood as withdrawing a portion of the API from the container as removal of a portion of the API from the container would result in changes of fill volume, gas environment, etc. At the time of testing the API subject to stability and/or stress testing, portions of the samples subject to stability and/or stress testing can be used for individual assays.

The long-term testing should cover a minimum of 12 months' duration on at least three primary batches at the time of submission and should be continued for a period of time sufficient to cover the proposed retest period. Additional data accumulated during the assessment period of the registration application should be submitted to the authorities if requested. Data from the accelerated storage condition and, if appropriate, from the intermediate storage condition can be used to evaluate the effect of short-term excursions outside the label storage conditions (such as might occur during shipping).

Long-term, accelerated, and, where appropriate, intermediate storage conditions for API are detailed in the sections below. The general case should apply if the API is not specifically covered by a subsequent section. It is understood that the time points for analysis indicated in the table are suggested end points for analysis. Interim analysis can be preformed at shorter time points (e.g., 1, 2, 3, 4, 5, 6, 7, 8, 9, 10, or 11 months). For API to be labeled as stable for storage for more than 12 months, time points beyond 12 months can be assessed (e.g., 15, 18, 21, 24 months). Alternative storage conditions can be used if justified.

TABLE 12

General Conditions for Stability Analysis

| Study | Storage condition | Time points for analysis |
|---|---|---|
| Long-term | Long-term* 25° C. ± 2° C./ 60% RH ± 5% RH or 30° C. ± 2° C./65% RH ± 5% RH | 12 months |
| Intermediate | 30° C. ± 2° C./65% RH ± 5% RH | 6 months |
| Accelerated | 40° C. ± 2° C./75% RH ± 5% RH | 6 months |

TABLE 13

Conditions for Stability Analysis for Storage in a Refrigerator

| Study | Storage condition | Minimum time period covered by data at submission |
|---|---|---|
| Long-term | 5° C. ± 3° C. | 12 months |
| Accelerated | 25° C. ± 2° C./ 60% RH ± 5% RH | 6 months |

TABLE 14

Conditions for Stability Analysis for Storage in a Freezer

| Study | Storage condition | Minimum time period covered by data at submission |
|---|---|---|
| Long-term | −20° C. ± 5° C. | 12 months |

Storage condition for API intended to be stored in a freezer, testing on a single batch at an elevated temperature (e.g., 5° C.±3° C. or 25° C.±2° C.) for an appropriate time period should be conducted to address the effect of short-term excursions outside the proposed label storage condition (e.g., stress during shipping or handling, e.g., increased temperature, multiple freeze-thaw cycles, storage in a non-upright orientation, shaking, etc.).

The assays performed to assess stability of an API include assays to that are used across most APIs to assess the physical properties of the API, e.g., degradation, pH, color, particulate formation, concentration, toxicity, etc. Assays to detect the general properties of the API are also selected based on the chemical class of the agent, e.g., denaturation and aggregation of protein based API. Assays to detect the potency of the API, i.e., the ability of the API to achieve its intended effect as demonstrated by the quantitative measurement of an attribute indicative of the clinical effect as compared to an appropriate control, are selected based on the activity of the particular agent. For example, the biological activity of the API, e.g., enzyme inhibitor activity, cell killing activity, anti-inflammatory activity, coagulation modulating activity, etc., is measured using in vitro and/or in vivo assays such as those provided herein. Pharmacokinetic and toxicological properties of the API are also assessed using methods known in the art, such as those provided herein.

Example 7: Analysis of Adherence to Glass Vials

Changes in the surface of glass can result in changes in the adherence of API to glass. The amount of agent in samples withdrawn from glass vials are tested at intervals to determine if the concentration of the API in solution changes over time. API are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the concentration of the API in solution. The concentration of the API is determined using methods and controls appropriate to the API. The concentration of the API is preferably determined in conjunction with at least one assay to confirm that the API, rather than degradation products of the API, is detected. In the case of biologics in which the conformational structure of the biologic agent is essential to its function of the API, the assays for concentration of the biologic are preferably preformed in conjunction with an assay to confirm the structure of the biologic (e.g., activity assay).

For example, in the cases of small molecule APIs, the amount of agent present is determined, for example, by mass spectrometry, optionally in combination with liquid chromatography, as appropriate, to separate the agent from any degradation products that may be present in the sample.

For protein based biologic APIs, the concentration of the API is determined, for example, using ELISA assay. Chromatography methods are used in conjunction with methods to determine protein concentration to confirm that protein fragments or aggregates are not being detected by the ELISA assay.

For nucleic acid biologic APIs, the concentration of the API is determined, for example, using quantitative PCR when the nucleic acids are of sufficient length to permit detection by such methods. Chromatography methods are used to determine both the concentration and size of nucleic acid based API.

For viral vaccine APIs, the concentration of the virus is determined, for example, using colony formation assays.

Example 8: Analysis of Pharmacokinetic Properties

Pharmacokinetics is concerned with the analysis of absorption, distribution, metabolism, and excretion of API. Storage and stress can potentially affect the pharmacokinetic properties of various API. To assess pharmacokinetics of API subject to stability and/or stress testing, agents are incubated in containers as described in Example 6. Preferably, the API are incubated both in standard glass vials with appropriate closures and glass vials such as those provided herein. At the desired intervals, samples are removed and assayed.

The API is delivered to subjects by the typical route of delivery for the API (e.g., injection, oral, topical). As pharmacokinetics are concerned with the absorption and elimination of the API, normal subjects are typically used to assess pharmacokinetic properties of the API. However, if the API is to be used in subjects with compromised ability to absorb or eliminate the API (e.g., subjects with liver or kidney disease), testing in an appropriate disease model may be advantageous. Depending on the half life of the compound, samples (e.g., blood, urine, stool) are collected at predetermined time points (e.g., 0 min, 30 min, 60 min, 90 min, 120 min, 4 hours, 6 hours, 12 hours, 24 hours, 36 hours, 48 hours, etc.) for at least two, preferably three half-lives of the API, and analyzed for the presence of the API and metabolic products of the API. At the end of the study, organs are harvested and analyzed for the presence of the API and metabolic products of the API.

The results are analyzed using an appropriate model selected based on, at least, the route of administration of the API. The pharmacokinetic properties of the API subjected to stability and/or stress testing are compared to API not subjected to stability or stress testing and other appropriate controls (e.g., vehicle control). Changes, if any, in pharmacokinetic properties as a result of storage of the API under each condition are determined.

Example 9: Analysis of Toxicity Profiles

Storage of API can result in alterations of toxicity of API as a result of reactivity of the API with the container, leeching of agents from the container, delamination resulting in particulates in the agent, reaction of the API molecules with each other or components of the storage buffer, or other causes.

Agents are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the toxicity the API. The toxicity of the API is determined using methods and controls appropriate to the API. In vitro and in vivo testing can be used alone or in combination to assess changes in toxicity of agents as a result of storage or stress.

In in vitro assays, cell lines are grown in culture and contacted with increasing concentrations of API subjected to stability and/or stress testing for predetermined amounts of time (e.g., 12, 24, 36, 48, and 72 hours). Cell viability is assessed using any of a number of routine or commercially available assays. Cells are observed, for example, by microscopy or using fluorescence activated cell sorting (FACS) analysis using commercially available reagents and kits. For example, membrane-permeant calcein AM is cleaved by esterases in live cells to yield cytoplasmic green fluorescence, and membrane-impermeant ethidium homodimer-1 labels nucleic acids of membrane-compromised cells with red fluorescence. Membrane-permeant SYTO 10 dye labels the nucleic acids of live cells with green fluorescence, and membrane-impermeant DEAD Red dye labels nucleic acids of membrane-compromised cells with red fluorescence. A change in the level of cell viability is detected between the cells contacted with API subjected to stress and/or stability testing in standard glass vials as compared to the glass vials provided herein and appropriate controls (e.g., API not subject to stability testing, vehicle control).

In vivo toxicity assays are performed in animals. Typically preliminary assays are performed on normal subjects. However, if the disease or condition to be treated could alter the susceptibility of the subject to toxic agents (e.g., decreased liver function, decreased kidney function), toxicity testing in an appropriate model of the disease or condition can be advantageous. One or more doses of agents subjected to stability and/or stress testing are administered to animals. Typically, doses are far higher (e.g., 5 times, 10 times) the dose that would be used therapeutically and are selected, at least in part, on the toxicity of the API not subject to stability and/or stress testing. However, for the purpose of assaying stability of API, the agent can be administered at a single dose that is close to (e.g., 70%-90%), but not at, a dose that would be toxic for the API not subject to stability or stress testing. In single dose studies, after administration of the API subject to stress and/or stability testing (e.g., 12 hours, 24 hours, 48 hours, 72 hours), during which time blood, urine, and stool samples may be collected. In long term studies, animals are administered a lower dose, closer to the dose used for therapeutic treatment, and are observed for changes indicating toxicity, e.g., weight loss, loss of appetite, physical changes, or death. In both short and long term studies, organs are harvested and analyzed to determine if the API is toxic. Organs of most interest are those involved in clearance of the API, e.g., liver and kidneys, and those for which toxicity would be most catastrophic, e.g., heart, brain. An analysis is performed to detect a change in toxicity between the API subjected to stress and/or stability testing in standard glass vials as compared to the glass vials provided herein, as compared to API not subject to stability and/or stress testing and vehicle control. Changes, if any, in toxicity properties as a result of storage of the API under each condition are determined.

Example 10: Analysis of Pharmacodynamic Profiles

Pharmacodynamics includes the study of the biochemical and physiological effects of drugs on the body or on microorganisms or parasites within or on the body and the mechanisms of drug action and the relationship between drug concentration and effect. Mouse models for a large variety of disease states are known and commercially available (see, e.g., jaxmice.jax.org/query/f?p=205:1:989373419139701::::P1_ADY: 1). A number of induced models of disease are also known.

Agents are incubated in containers as described in the stability testing and/or stress testing methods provided in Example 6. Preferably, the samples are incubated both in standard glass vials with appropriate closures and glass vials such as those provided herein. At the desired intervals, samples are removed and assayed for pharmacodynamic activity using known animal models. Exemplary mouse models for testing the various classes of agents indicated are known in the art.

The mouse is treated with the API subject to stability and/or stress testing. The efficacy of the API subject to stability and/or stress testing to treat the appropriate disease or condition is assayed as compared to API not subject to stability and/or stress testing and vehicle control. Changes, if any, in pharmacodynamic properties as a result of storage of the API under each condition are determined.

Example 11: Confirmation of Stability and Integrity of Antibody API by Size Determination (PERJETA (Pertuzumab), ACTEMRA (Tocilizumab), KADCYLA (Trastuzumab Emtansine), Onartuzumab, Obinutuzumab, Ocrelizumab and Lebrikizumab)

Antibody based API are used in the treatment of a number of diseases and conditions. The activity of antibody based API is dependent upon the ability of the antibody to specifically bind to its target antigen and, depending on the specific agent and condition to be treated, for the antibody-antigen complex to be recognized and cleared by the body. These activities are dependent upon proper subunit structure of the antibody which can be assessed, for example, by column chromatography and gel electrophoresis and staining. Column chromatography can also be used to assess protein concentration and degradation.

For example, pertuzumab (PERJETA™), a recombinant humanized monoclonal antibody that targets the extracellular dimerization domain (Subdomain II) of the human epidermal growth factor receptor 2 protein (HER2), is presently indicated in combination with trastuzumab and docetaxel for the treatment of patients with HER2-positive metastatic breast cancer who have not received prior anti-HER2 therapy or chemotherapy for metastatic disease.

Tocilizumab (ACTEMRA®), a humanized anti-human interleukin-6 (IL-6) receptor antibody, is presently indicated for the treatment of rheumatoid arthritis.

Ado-trastuzumab emtansine (KADCYLA), a HER2-targeted antibody and microtubule inhibitor conjugate, is presently indicated for the treatment of patients with HER2-positive, metastatic breast cancer who previously received trastuzumab and a taxane, separately or in combination.

Onartuzumab (MetMAb), an anti-Met monovalent (one-armed), monoclonal antibody, is presently in development for the treatment of cancer.

Obinutuzumab, a glycoengineered, fully humanized anti-CD20 IgG1 monoclonal antibody, is presently in development for the treatment of hematological malignancies (cancers which affect the blood, bone marrow and lymph nodes).

Ocrelizumab, a humanized anti-CD20 monoclonal antibody, designed to selectively target CD20-positive B-cells, which are believed to play a critical role in multiple sclerosis (MS).

Lebrikizumab, a humanized anti-interleukin-13 (IL-13) monoclonal antibody, was shown to significantly decrease the symptoms of asthma in patients whose disease cannot be adequately controlled with inhalable glucocorticoids.

Antibody based API are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine antibody based API size and subunit structure, for example, by chromatography and/or gel electrophoresis methods.

Chromatography Methods for Size Detection

Samples of antibody based API subject or not subject to stability and/or stress testing are diluted and subject to analysis by size exclusion chromatography (SEC), preferably SEC-high performance liquid chromatography (SEC-HPLC). Chromatography columns are available from a number of commercial vendors (e.g., WATERS, BIO-RAD). Size exclusion chromatography columns separate compounds by gel filtration chromatography. The working range of the gel is the volume between the void volume, those solutes which elute first, and the totally included volume, those solutes which elute last. Protein aggregates; complexes, e.g., dimers; monomers; and fragments, can be detected by photometry for absorbance at 350-500 nm or by UV detection at 280 nm.

The specific column type, column size, solvent type, flow rate, and detector type can be selected based on the specific API to be analyzed. Different solvents can be selected to detect monomer or higher order structures. Antibodies are composed of two light chains and two heavy chains held together by disulfide bonds. Column chromatography methods can be used to assess the antibody structure as a tetramer, under non-reducing conditions, or as the monomer subunits, under reducing conditions. Antibody-antigen binding can also be analyzed by incubating an excess of antigen with the antibody prior to column chromatography. The amount of antibody-antigen complex is determined by a shift in molecular weight of the antibody, and the ratio of antibody that does or does not bind antigen is determined. An excess of unbound antigen is observed.

The relative amounts of aggregates, tetramers, monomers, degradation products, and antigen binding are determined in an antibody API sample that has undergone stability and/or stress testing and compared to the control sample that has not undergone stability and/or stress testing. The total protein concentration is also determined. A change in the amount of aggregate, tetramer, monomer, or degradation products; and/or a change in total protein concentration, indicate a change in the API during stress and/or stability testing.

Gel Electrophoresis Methods for Size Detection

Samples of antibody based API subject or not subject to stability and/or stress testing are diluted and resolved by gel electrophoresis. SDS-PAGE is used to determine protein size and aggregate formation. Native, non-reducing gel electrophoresis is used to analyze antibody tetramer structure. Antibodies resolved by gel electrophoresis are detected using sensitive staining methods, such as silver stain. Gel electrophoresis and silver staining methods are known in the art. A change in the amount of aggregate, tetramer, monomer, or degradation products; and/or a change in total protein concentration, indicate a change in the antibody based API during stress and/or stability testing.

Example 12: Confirmation of Stability and Integrity of Protein API by Antibody Binding A number of antibody-based API are known including, but not limited to, PERJETA (pertuzumab), ACTEMRA (tocilizumab), KADCYLA (trastuzumab emtansine), Met-MAb (onartuzumab), obinutuzumab, ocrelizumab and lebrikizumab. Antibody concentration and conformation can be assessed using an enzyme-linked immunosorbent assay (ELISA).

Antibody based API are incubated in containers as described in the stability testing and/or stress testing methods provided in Example 6. Preferably, the samples are incubated both in standard glass vials with appropriate closures and glass vials such as those provided herein. At the desired intervals, samples are removed and assayed using ELISA. A sandwich ELISA method, described briefly herein, can be used to probe the structure of the antigen biding domain as well as the immunoglobulin domain. Variations based on the specific antibody API and ELISA format used, as well as selection of appropriate dilutions and controls, are well within the ability of those of skill in the art.

In the description of sandwich ELISA methods below for the detection and characterization of an antibody based API, for the sake of clarity, the example refers to the IL-13-binding antibody lebrikizumab and its antigen IL-13. However, it is understood that any of the antibody API and their cognate antigens can be used in the methods.

A first antibody capable of binding IL-13 simultaneously with lebrikizumab is bound to a solid support. IL-13 is then added to the well. Serial dilutions of samples of lebrikizumab, subject or not subject to stability and/or stress testing, are diluted and contacted with the complex attached to the solid support. Therefore, the amount of lebrikizumab present in the well is dependent upon the amount of lebrikizumab in the sample subject to or not subject to stability and/or stress testing with a correctly folded antigen binding domain to bind IL-13. A detectably labeled secondary antibody (e.g., horse radish peroxidase, alkaline phosphatase) that binds to human IgG1κ is added to the well. The amount of secondary antibody in the sample is detected using an appropriate method based on the label. The amount of lebrikizumab detected in the samples subject to or not subject to stability and/or stress testing are compared.

Example 13: Assessing Stability and Efficacy of Pertuzumab (Perjeta) and Ado-Trastuzumab Emtansine (Kadcyla)

Pertuzumab or ado-trastuzumab emtansine samples will be incubated in containers as described in the stability testing and/or stress testing methods provided in Example 6. Preferably, the samples will be incubated both in standard glass vials with appropriate closures and glass vials such as those provided herein. At the desired intervals, samples will be removed and assayed in vitro or in vivo assay to assess the activity of pertuzumab or ado-trastuzumab emtansine. The activity will be determined using methods and controls appropriate to the agent.

The SKBR-3 cells expressing the Her2 receptor are cultured under conditions to permit the HER2/neu receptor expression. A dilution series of pertuzumab or ado-trastuzumab emtansine subjected to stability and/or stress testing is prepared and added to the cells to bind to the HER2/neu receptor. Peripheral blood mononuclear cells (PBMCs) are then added to the cells to bind to pertuzumab or ado-trastuzumab emtansine to promote apoptosis. Live/dead cell assays or apoptotic assays are used with immunofluorescence or FACS analysis to determine the activity of pertuzumab or ado-trastuzumab emtansine in promoting apoptosis.

Example 14: Determination of Immunological Activity of Tocilizumab

Tocilizumab (ACTEMRA) samples will be incubated in containers as described in the stability testing and/or stress testing methods provided in Example 6. Preferably, the samples will be incubated both in standard glass vials with appropriate closures and glass vials such as those provided herein. At the desired intervals, samples will be removed and assayed in vitro or in vivo assay to assess the activity of Tocilizumab. The activity will be determined using methods and controls appropriate to the agent.

The immunological activity of tocilizumab is assessed using human gp130-transfected cell, BAF-h130, COS-7 cells, and IL-6-dependent myeloma cell line, KPMM2 as described below and in M. Mihara et al., *International Immunopharmacology* (2005) 5:1731-1740.

IL-6 Signaling Mediated by sIL-6R

BAF-h130 cell is a human gp130-transfected murine pro-B cell, BAF-B03. BAF-h130 cells ($1 \times 10^4$) are cultured with IL-6 (100 ng/mL) (Genzyme-techne, Minneapolis, Minn., USA), sIL-6R (500 ng/mL) or tocilizumab (0.01-100 Ag/mL) at 37° C. under 5% CO2 for 4 days in 96-well flat-bottomed plates. The culture is performed in quadruplicate. [$^3$H]-thymidine (10 μL/well, 3.7 MBq/mL) (Amercham Pharmacia Biotech, Piscataway, N.J., USA) is added to each well 5 h before the completion of culture. After incubation, the amount of [$^3$H]-thymidine uptake into cells is determined with a scintillation counter (1450 MicroBeta) (Wallace Oy, Turku, Finland).

BaF-h130 cells could grow by the co-addition of IL-6 (100 ng/ml) and sIL-6R (500 ng/mL), but not by IL-6 or sIL-6R alone. Tocilizumab suppresses the proliferation of BAF-h130 cells induced by the complex of IL-6 and sIL-6R in a concentration-dependent manner. Tocilizumab suppresses the IL-6/sIL-6R complex-induced proliferation of human gp130-transfected cell, BAF-h130.

Transfection of Cos-7 Cells with Human IL-6R Expression Vector

COS-7 cells ($1 \times 10^6$) are inoculated into 10 mL of the medium on a 10 cm dish. Next day, the old medium is replaced with 20 mL of new medium per dish. After 3.42 mL of Opti-MEM (Invitrogen, Carlsbad, Calif., USA) is placed in a polystyrene tube, 180 μL of Trans-IT LTI reagent (Takara Bio, Shiga, Japan) is added and mixed well. The mixture (3.6 mL) is left at room temperature for 15 min. After 60 μg of human IL-6R expression vector hIL-6R/pcDNA3.1 (+) or control (empty) vector pcDNA3.1 (+) (Invitrogen) is added to 5.4 mL of Opti-MEM and mixed well with the above mixture, the resulting solution (9 mL) is allowed to stand at room temperature for 15 min, divided in 3 mL aliquots on three dishes, and incubated at 37 8 C under 5% CO2 for 3 days.

Il-6 Signaling Mediated by mIL-6R

IL-6-dependent myeloma cell line, KPMM2 ($1 \times 10^5$ cells/mL) are cultured with IL-6 (0-100 ng/mL) and tocilizumab (0-100 µg/mL) in a CO2 incubator for 4 days in a 96-well plate. After incubation, the amount of [$^3$H]-thymidine uptake into cells is determined with a scintillation counter.

Tocilizumab increases the fluorescent intensity in COS-7 cells expressing human IL-6R (IL-6R transfectant), but not in COS-7 mock cells (a control vector pcDNA3.1 (+) transfectant), whereas control hIgG1 does not increase fluorescent intensity in both IL-6R transfectant and mock transfectant. Tocilizumab has the ability to bind to human IL-6R expressing COS-7 cells and to suppress the growth of the IL-6-dependent myeloma cell line, KPMM2.

Example 15: Determination of Immunological Activity of Onartuzumab

Onartuzumab samples will be incubated in containers as described in the stability testing and/or stress testing methods provided in Example 6. Preferably, the samples will be incubated both in standard glass vials with appropriate closures and glass vials such as those provided herein. At the desired intervals, samples will be removed and assayed in vitro or in vivo assay to assess the activity of onartuzumab. The activity will be determined using methods and controls appropriate to the agent.

The immunological activity of onartuzumab is assessed using assays as described below.

Electro-Chemiluminescent Assay for Onartuzumab Blocking of HGF/cMet Binding

Purified cMet-Ig protein is biotinylated by incubating with 20-fold molar excess NHS-X-Biotin in 0.1 M NaHCO3, pH 8.5 using biotin-X-NHS (Research Organics, Cleveland, Ohio). Purified human 2-chain HGF is labeled with BV-TAG (cat #110034) via NHS-ester chemistry according to manufacturer's directions (BioVeris International, Gaithersburg, Md.). cMet-Ig-biotin (500 ng/mL), HGF-Ruthenium Tag (250 ng/mL), and titrations of onartuzumab antibody ranging from 3333-0.21 nM of antibody are incubated together in a volume of 100 µl of assay diluent: PBS+0.5% BSA/0.5% Tween 20/0.033% Proclin (Supelco Inc. Bellefonte Pa.). The mixtures are incubated in sealed polypropylene round bottom 96 well plates (Corning) for 24 hours at room temperature with shaking. Streptavidin magnetic beads (Dynabeads, BioVeris) are added. Following a final 45 min incubation with vigorous shaking, the plates are read using a BioVeris M-Series instrument (BioVeris International, Gaithersburg, Md.).

KIRA (HGF-Dependent-Met Phosphorylation)

A549 cells (ATCC, Manassas, Va.) are maintained in growth medium (Ham's F12/DMEM 50:50 [Gibco, Grand Island, N.Y.] containing 10% fetal bovine serum (FBS, Sigma, St. Louis, Mo.). To prepare cells for the assay, cells from confluent cultures are detached using Accutase (ICN, Aurora, Ohio) and seeded into 96 well plates at a density of 50,000 cells per well. After an overnight incubation at 37° C., growth media is removed and cells are serum starved for 30-60 min in medium containing 0.1% FBS. To determine the ability of onartuzumab to inhibit cMet phosphorylation, the molecule is serially diluted from 200 to 0.19 nM in medium+0.1% FBS and added to the assay plates. After a 15 min incubation at 37° C., HGF (50 ng/ml) is added. The plates are then incubated for an additional 10 minutes at 37° C., the media is removed and a cell lysis buffer is added (Cell Signaling Technologies, Cat #9803, Beverly, Mass.; supplemented with a protease inhibitor cocktail purchased from Calbiochem, Cat #539131, San Diego, Calif.). The lysates are analyzed for phosphorylated c-Met via an electrochemiluminescence assay using an BioVeris M-Series instrument (BioVeris International, Gaithersburg, Md.). An anti-phosphotyrosine mAb (clone 4G10, Upstate, Lake Placid, N.Y.) is labeled with BV-TAG via NHS-ester chemistry according to manufacturer's directions (BioVeris). Onartuzumab is biotinylated using biotin-X-NHS (Research Organics, Cleveland, Ohio). The BV-TAG-labeled 4G10 and biotinylated onartuzumab are diluted in assay buffer (PBS/0.5% Tween-20/0.5% BSA) and added as a cocktail to the cell lysates. After a 1.5-2 hr incubation at room temperature with vigorous shaking, streptavidin magnetic beads (Dynabeads, BioVeris) are added. Following a final 45 min incubation, the plates are read on the BioVeris instrument.

Cell Culture and Proliferation Assay

BaF3 is a murine IL-3 dependent lymphoid cell that normally does not express cMet and does not respond to HGF. However, in BaF3-hMet derived by transfection with a normal, full-length cDNA for human c-Met (Schwall et al., *J. Cell Biol.* (1996), 133:709-718), HGF stimulates proliferation and survival in the absence of 1L-3. BaF3-hMet and BaF3-neo cells are routinely passaged in RPMI 1640, 5% fetal bovine serum, 4 µl/L β-mercapthoethanol, 100 U/ml penicillin, 100 µg/ml streptomycin sulfate, 2 mM L-glutamine, and 5% WEHI-conditioned medium as a source of IL-3. To measure HGF-dependent proliferation the number of cells after 3 days of treatment is quantitated by adding 25 µl Alarma Blue (Trek Diagnostic Systems; Cleveland, Ohio) and measuring fluorescence intensity 6 hours later. Control experiments are proliferation of these cells in the absence of HGF. H358-PSF2 and HGF-PSF8 cells are passaged in RPMI 1640, 10% fetal bovine serum, 100 U/ml penicillin, 100 µg/ml streptomycin sulfate, 2 mM L-glutamine. The assay medium is RPMI 1640 plus 0.1%, 0.5% BSA, or 10% FBS respectively.

Immunoprecipitation and Western Blot

H358 cells are a cell line derived from human non-small cell lung carcinoma (NSCLC). H358-PSF2, H358-PSF8 cells are human HGF stable transfected H358 cells (Tsao et al., *Neoplasia*, Vol. 2, No. 3, 2000), and are cultured in RPMI 1640, 10% fetal bovine serum, 100 U/ml penicillin, 100 µg/ml streptomycin sulfate, 2 mM L-glutamine. cMet tyrosine phosphorylation detection was performed essentially as described previously (Zioncheck, *J. Bio. Chem.*, 270(28):16871-8, 1995). In brief, cells are plated in 60-mm plates overnight, and medium is changed to RPMI 1640 containing 0.5% BSA, before adding the combinations of with or without 1 nM HGF or competitor onartuzumab. After 10 min at 37° C., medium is removed and cells are lysed using lysis buffer (150 mM NaCl, 1.5 mM MgCl2, 1% Triton X-100, 1× protease inhibitor cocktail, 1× phosphatase inhibitor cocktail (Sigma, St. Louis, Mo.)). After spinning, the supernatant of the lysate is incubated with anti-cMet IgG polyclonal antibody (c-28; Santa Cruz Biotechnology, Santa Cruz, Calif.) bound to protein G-Sepharose for 1 hour at 4° C. The immune complexes are washed and boiled in 1× sample buffer, before separation by SDS-PAGE and electroblotting to nitrocellulose. Phosphotyrosine-containing proteins are visualized using an anti-phosphotyrosine antibody (4G10; Upstate Biotechnology, Waltham, Mass.) followed by HRP-conjugated goat anti-mouse Fab (1:10,000; Jackson Labs, West Grove, Pa.), and in the case of total cMet using c-28 antibody (1:400; Santa Cruz Biotechnology,

Example 16: Determination of Immunological Activity of Obinutuzumab and Ocrelizumab Obinutuzumab or ocrelizumab samples will be incubated in containers as described in the stability testing and/or stress testing methods provided in Example 6. Preferably, the samples will be incubated both in standard glass vials with appropriate closures and glass vials such as those provided herein. At the desired intervals, samples will be removed and assayed in vitro or in vivo assay to assess the activity of obinutuzumab or ocrelizumab. The activity will be determined using methods and controls appropriate to the agent.

Human C1q Analysis

Binding to human C1q is assessed in a flow cytometry assay using fluorescein labeled C1q (C1q can be obtained from Quidel, Mira Mesa, Calif., Prod. No. A400 and FITC label from Sigma, St. Louis Mo., Prod. No. F-7250; FITC. Labeling of C1q is accomplished in accordance with the protocol described in Selected Methods In Cellular Immunology, Michell & Shiigi, Ed. (W.H. Freeman & Co., San Francisco, Calif., 1980, p. 292). Analytical results are derived using a Becton Dickinson FACScan™ flow cytometer (fluorescein measured over a range of 515-545 nm). Equivalent amounts of obinutuzumab or ocrelizumab, human IgG1 nadK myeloma protein (Binding Site, San Diego, Calif., Prod. No. BP078) are incubated with an equivalent number of CD20-positive SB cells, followed by a wash step with FACS buffer (0.2% BSA in PBS, pH 7.4, 0.02% sodium azide) to remove unattached antibody, followed by incubation with FITC labeled C1q. Following a 30-60 minutes incubation, cells are again washed. The three conditions, including FITC-labeled C1q as a control, are analyzed on the FACScan™ following manufacturing instructions.

Complement Dependent Cell Lyses

Obinutuzumab or ocrelizumab is analyzed for its ability to lyse lymphoma cell lines in the presence of human serum (complement source). CD20 positive SB cells are labeled with $^{51}$Cr by admixing 100 μCi of $^{51}$Cr with 1×10$^6$ SB cells for 1 hr at 37° C.; labeled SB cells are then incubated in the presence of equivalent amounts of human complement and equivalent amounts (0-50 μg/ml) of obinutuzumab or ocrelizumab for 4 hrs at 37° C. (see, Brunner, K. T. et al., "Quantitative assay of the lytic action of immune lymphoid cells on $^{51}$Cr-labeled allogeneic target cells in vitro," *Immunology* 14:181-189 (1968).

Antibody Dependent Cellular Cytotoxicity Effector Assay

For this study, CD20 positive cells (SB) and CD20 negative cells (T cell leukemia line HSB; see, Adams, Richard, "Formal Discussion," Can. Res. 27:2479-2482 (1967); ATCC deposit no. ATCC CCL 120.1) are utilized; both are labeled with $^{51}$Cr. Analysis is conducted following the protocol described in Brunner, K. T. et al., "Quantitative assay of the lytic action of immune lymphoid cells on $^{51}$Cr-labeled allogeneic target cells in vitro; inhibition by isoantibody and drugs," *Immunology* 14:181-189 (1968). Anti-CD20 antibody dependent cell mediated lysis of CD20 positive SB target cells ($^{51}$Cr Cr-labeled) at the end of a 4 hr, 37° C. incubation, is assessed (effector cells were human peripheral lymphocytes; ratio of effector cells:target was 100:1).

Example 17: Determination of Immunological Activity of Lebrikizumab

Lebrikizumab samples will be incubated in containers as described in the stability testing and/or stress testing methods provided in Example 6. Preferably, the samples will be incubated both in standard glass vials with appropriate closures and glass vials such as those provided herein. At the desired intervals, samples will be removed and assayed in vitro or in vivo assay to assess the activity of lebrikizumab. The activity will be determined using methods and controls appropriate to the agent.

Reactivity of Lebrikizumab with Human and Mouse IL13 in ELISA

The reactivity of lebrikizumab is tested by ELISA. Different wells of 96-well microtest plates are coated with either *E. coli* expressed non-glycosylated human IL13 (R&D Systems), 293T cell expressed glycosylated MT-IL13/Fc, or *E. coli* expressed mouse IL13 (R&D Systems) by the addition of 100 μL of IL13 protein at 0.1 μg/mL in PBS. After overnight incubation at room temperature, the wells are treated with PBSTB (PBST containing 2% BSA) to saturate the remaining binding sites. The wells are then washed with PBST.

One hundred microliters of two-fold serially diluted lebrikizumab (0.5 μg/mL (3.33 nM) to 0.05 ng/mL (0.00033 nM)) are added to the wells for 1 hour at room temperature. An anti-IL13 MAb JES-5A2 from (BD Biosciences-Pharmingen, San Diego, Calif.) is also tested as a positive control. This antibody is generated by using *E. coli* expressed human IL13 as immunogen. An isotype-matched mouse anti-HIV-1 gp120 MAb is used as irrelevant negative control. The wells are then washed with PBST. Bound lebrikizumab is detected by incubation with diluted HRP-goat anti-mouse IgG (Fc) (Jackson ImmunoResearch) for 1 hour at room temperature. Peroxidase substrate solution is then added for color development as described above. The OD450 was measured using an ELISA reader.

Neutralizing IL-13-Autocrine Dependent Proliferation Assay Using L-1236 and HDLM-2 Cells L-1236 and HDLM-2 are Hodgkin lymphoma cell lines obtained from the German Collection of Microorganisms and Cell Cultures (DSMZ, Braunschweig, Germany). These cell lines produce IL13 which in turn activates their cell proliferation in an autocrine fashion (Kapp U et. al., *J. Exp. Med.* 189:1939 (1999)).

Cells are cultured (25,000 cells/well) in the presence or absence of lebrikizumab (0.2, 0.02 and 0.002 μg/mL) in 5% CO2 at 37° C. for 3-5 days. Cell proliferation is then measured either by an assay using the tetrazolium compound MTS (Promega, Madison, Wis.) (readouts at Oat %) or by the incorporation of 3H-thymidine (Amersham Biosciences, Piscataway, N.J.).

The addition of active lebrikizumab to the culture of these cell lines is expected to inhibit their proliferation by the binding and inactivation of the IL13 produced by these cells.

Assay for IL13-Regulated CD14 and CD23 Expression on Primary Human Monocytes

IL13 induces suppression of CD14 expression and the up-regulation of CD23 expression in the human monocytes (de Waal Malefyt et al., *J. Immunol.*, 151:6370 (1993), Chomarat et al., *Int. Rev. Immunol.*, 17:1 (1998)). Peripheral blood leukocytes (PBLs) are isolated from freshly collected, heparinized whole blood of healthy human donors by density-gradient centrifugation in Histopaque-1077 (Sigma). PBLs (1.5×106) suspended in RPMI-1640 medium (Invitrogen) with 5% fetal bovine serum are added to each well of a 96-well tissue culture plate containing recombinant IL13 (final 10 ng/mL=0.813 nM) and lebrikizumab or an irrelevant antibody (three-fold serial dilutions, from a final 12 μg/mL=80 nM). CD14 expression or CD23 expression on monocytes is suppressed or up-regulated, respectively, by the addition of 0.813 nM human IL13 to the incubating medium. The medium control contained RPMI-1640/FBS medium without recombinant IL13.

The cells are incubated in 5% CO2 at 37° C. for 2 days. The cells are harvested for staining with anti-CD14-FITC or anti-CD23-PE (BD Biosciences-Pharmingen). The expression levels of CD14 and CD23 in the monocyte population are measured by flow cytometry and represented by Median Fluorescence Intensity (MFI).

Active lebrikizumab with high affinity neutralizing IL-13 is able to demonstrate high potency in inhibiting the effect of IL13 on CD14 expression. Active lebrikizumab with high affinity neutralizing IL-13 is able to demonstrate high potency in inhibiting the effect of IL13 on CD23 expression.

IL13-Induced STAT6 Phosphorylation Assay In THP-1 Cells

IL13 can activate the myeloid cell line THP-1 (ATCC, Manassas, Va.) to induce phosphorylation of STAT6 which is a critical step in the signal transduction pathway of IL13 (Murata T et al., *Int. Immunol.* 10:1103-1110 (1998). Lebrikizumab incubated in different containers is tested for inhibition of IL13 in this assay.

THP-1 cells are maintained in Dulbecco's Modified Eagle Medium (DMEM) (Invitrogen) supplemented with 5% fetal bovine serum. On the day of experiments, the cells are washed and incubated in serum-free DMEM at 37° C. in 5% CO2 for 2 hours. 0.3×106 cells in 80 μL of the serum-free medium are then added to each well of a 96-well round-bottom plate. One hundred and twenty microliters of medium containing human IL13 (final concentration of 10 ng/mL=0.813 nM) and lebrikizumab (5 fold serial dilutions, from final concentration of 0.5 μg/mL=3.333 nM). Negative control wells containing either no IL13 or IL13 and an isotype-matched irrelevant mouse MAb.

The mixtures are incubated at 37° C. under 5% CO2 for 10 min. The plates are then centrifuged at 300×g for 3 minutes at 4° C. After discarding the supernatant, the cell pellets are resuspended in 100 μL of Laemmli non-reducing sample buffer (SDS-PAGE loading buffer, BioRad, CA) and then transferred to microcentrifuge tubes. The tubes are heated at 95° C. for 5 minutes and then centrifuged at 10,000×g for 10 minutes at room temperature. The supernatants are collected and analyzed by 4-20% gradient SDS-PAGE. The separated proteins are transferred to PVDF membrane which is then incubated with diluted mouse anti-human Stat6 (Y641, phospho-specific) MAb (BD Biosciences Pharmingen).

The bound antibody is detected by HRP conjugated goat anti-mouse IgG (Fc) antibodies (Jackson ImmunoResearch Laboratories). The immunoreactive proteins are identified on film, using enhanced chemiluminescence detection (Supersignal West Pico Chemiluminescent Substrate, Pierce). Stat6 is phosphorylated in THP-1 cells treated with 0.813 nM human IL13. Dose-dependent inhibition of Stat6 phosphorylation is found when the cells are treated with potent neutralizing lebrikizumab.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A pharmaceutical composition product comprising:
    pertuzumab, tocilizumab, trastuzumab emtansine, MetMAb (onartuzumab), obinutuzumab, ocrelizumab or lebrikizumab and a pharmaceutically acceptable excipient;
    contained within a glass pharmaceutical container a glass composition comprising:
    $SiO_2$ in a an amount greater than or equal to about 72 mol. % and less than or equal to about 78 mol. %;
    alkaline earth oxide comprising both MgO and CaO, wherein CaO is present in an amount up to about 1.0 mol. %, and a ratio (CaO (mol. %)/(CaO (mol. %)+MgO (mol. %))) is less than or equal to 0.5;
    X mol. % $Al_2O_3$, wherein X is greater than or equal to about 5 mol. % and less than or equal to about 7 mol. %;
    Y mol. % alkali oxide, wherein the alkali oxide comprises $Na_2O$ in an amount greater than about 8 mol. %; and,
    a ratio of a concentration of $B_2O_3$ (mol. %) in the glass container to (Y mol. %–X mol. %) is less than or equal to 0.3.

2. The pharmaceutical product of claim 1, wherein the pharmaceutical container comprises a compressive stress greater than or equal to 150 MPa.

3. The pharmaceutical product of claim 1, wherein the pharmaceutical container comprises a compressive stress greater than or equal to 250 MPa.

4. The pharmaceutical product of claim 1, wherein the pharmaceutical container comprises a depth of layer greater than 30 μm.

5. The pharmaceutical product of claim 1, wherein the pharmaceutical product has increased stability, product integrity, or efficacy.

6. The pharmaceutical product of claim 1:
    wherein the glass pharmaceutical container has a compressive stress greater than or equal to 150 MPa and a depth of layer greater than 10 μm, and wherein the pharmaceutical product comprises increased stability, product integrity, or efficacy.

7. The pharmaceutical product of claim 1:
    wherein the glass pharmaceutical container is substantially free of boron, and wherein the pharmaceutical product comprises increased stability, product integrity, or efficacy.

8. The pharmaceutical product of claim 7, wherein the glass pharmaceutical container comprises a compressive stress greater than or equal to 150 MPa and a depth of layer greater than 25 μm.

9. The pharmaceutical product of claim 8, wherein the glass pharmaceutical container comprises a compressive stress greater than or equal to 300 MPa and a depth of layer greater than 35 μm.

10. The pharmaceutical product of claim 7, wherein said glass pharmaceutical container comprises a substantially homogeneous inner layer.

11. The pharmaceutical product of claim 10, wherein said glass pharmaceutical container comprises a compressive stress greater than or equal to 150 MPa and a depth of layer greater than 25 μm.

12. The pharmaceutical product of claim 1, wherein the pharmaceutical container comprises an internal homogeneous layer.

* * * * *

UNITED STATES PATENT AND TRADEMARK OFFICE
CERTIFICATE OF CORRECTION

PATENT NO. : 9,713,572 B2  
APPLICATION NO. : 14/259255  
DATED : July 25, 2017  
INVENTOR(S) : Wendell P. Weeks et al.

Page 1 of 1

It is certified that error appears in the above-identified patent and that said Letters Patent is hereby corrected as shown below:

On the Title Page

Item (*), in Column 1, below "U.S.C. 154 by 180 days." insert -- This patent is subject to a terminal disclaimer. --.

In Column 2, item (45), Date of Patent, Line 1, before "Jul. 25, 2017" insert -- * --.

On page 4, in Column 2, item (56), Other Publications, Line 37, delete "Editro:" and insert -- Editor: --, therefor.

In the Claims

In Column 62, Line 4, Claim 1, after "pharmaceutical" delete "composition".

In Column 62, Line 12, Claim 1, after "$SiO_2$ in" delete "a".

In Column 62, Line 38, Claim 6, delete "claim 1:" and insert -- claim 1, --, therefor.

In Column 62, Line 44, Claim 7, delete "claim 1:" and insert -- claim 1, --, therefor.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*